(12) United States Patent
Khare

(10) Patent No.: US 7,928,074 B2
(45) Date of Patent: Apr. 19, 2011

(54) COMBINATION THERAPY WITH CO-STIMULATORY FACTORS

(75) Inventor: Sanjay D. Khare, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 307 days.

(21) Appl. No.: 12/143,693

(22) Filed: Jun. 20, 2008

(65) Prior Publication Data

US 2008/0279862 A1 Nov. 13, 2008

Related U.S. Application Data

(63) Continuation of application No. 10/748,112, filed on Dec. 29, 2003, now abandoned.

(60) Provisional application No. 60/437,405, filed on Dec. 30, 2002.

(51) Int. Cl.
*A61K 38/16* (2006.01)
*A61K 39/395* (2006.01)

(52) U.S. Cl. .................... 514/21.2; 424/130.1

(58) Field of Classification Search .................. None
See application file for complete search history.

(56) References Cited

U.S. PATENT DOCUMENTS

| | | | |
|---|---|---|---|
| 2,512,572 A | 6/1950 | Smith et al. |
| 3,773,919 A | 11/1973 | Boswell et al. |
| 3,892,801 A | 7/1975 | Kazan |
| 3,989,703 A | 11/1976 | Niculescu-Duvăz et al. |
| 4,057,548 A | 11/1977 | Wiecko |
| 4,067,867 A | 1/1978 | Wiecko |
| 4,079,056 A | 3/1978 | Piper et al. |
| 4,080,325 A | 3/1978 | Ellard |
| 4,136,101 A | 1/1979 | Kazan |
| 4,179,337 A | 12/1979 | Davis et al. |
| 4,224,446 A | 9/1980 | Catalucci |
| 4,289,872 A | 9/1981 | Denkewalter et al. |
| 4,306,064 A | 12/1981 | Ellard et al. |
| 4,374,987 A | 2/1983 | Singh et al. |
| 4,421,913 A | 12/1983 | Ellard et al. |
| 4,474,893 A | 10/1984 | Reading |
| 4,619,794 A | 10/1986 | Hauser |
| 4,699,880 A | 10/1987 | Goldstein |
| 4,767,859 A | 8/1988 | Zimmermann |
| 4,816,567 A | 3/1989 | Cabilly et al. |
| 4,935,343 A | 6/1990 | Allison et al. |
| 4,946,778 A | 8/1990 | Ladner et al. |
| 4,970,154 A | 11/1990 | Chang |
| 5,075,222 A | 12/1991 | Hannum et al. |
| 5,106,627 A | 4/1992 | Aebischer et al. |
| 5,136,021 A | 8/1992 | Dembinski et al. |
| 5,151,510 A | 9/1992 | Stec et al. |
| 5,180,812 A | 1/1993 | Dower et al. |
| 5,229,490 A | 7/1993 | Tam |
| 5,260,203 A | 11/1993 | Ladner et al. |
| 5,319,071 A | 6/1994 | Dower et al. |
| 5,344,915 A | 9/1994 | LeMaire et al. |
| 5,359,032 A | 10/1994 | Dayer et al. |
| 5,359,037 A | 10/1994 | Wallach et al. |
| 5,399,346 A | 3/1995 | Anderson et al. |
| 5,457,035 A | 10/1995 | Baum et al. |
| 5,464,937 A | 11/1995 | Sims et al. |
| 5,488,032 A | 1/1996 | Dower et al. |
| 5,492,888 A | 2/1996 | Dower et al. |
| 5,512,544 A | 4/1996 | Wallach et al. |
| 5,547,970 A | 8/1996 | Weithmann et al. |
| 5,593,875 A | 1/1997 | Wurm et al. |
| 5,608,035 A | 3/1997 | Yanofsky et al. |
| 5,633,145 A | 5/1997 | Feldmann et al. |
| 5,641,673 A | 6/1997 | Haseloff et al. |
| 5,672,344 A | 9/1997 | Kelley et al. |
| 5,674,704 A | 10/1997 | Goodwin et al. |
| 5,676,954 A | 10/1997 | Brigham |
| 5,679,559 A | 10/1997 | Kim et al. |
| 5,695,953 A | 12/1997 | Wallach et al. |
| 5,747,444 A | 5/1998 | Haskill et al. |
| 5,756,086 A | 5/1998 | McClelland et al. |
| 5,759,546 A | 6/1998 | Weinberg et al. |
| 5,770,197 A | 6/1998 | Linsley et al. |
| 5,773,253 A | 6/1998 | Linsley et al. |
| 5,783,665 A | 7/1998 | Baum et al. |
| 5,807,862 A | 9/1998 | Klein et al. |
| 5,808,029 A | 9/1998 | Brockhaus et al. |
| 5,811,261 A | 9/1998 | Wallach et al. |
| 5,817,822 A | 10/1998 | Nantermet et al. |
| 5,830,742 A | 11/1998 | Black et al. |
| 5,834,435 A | 11/1998 | Slesarev |
| 5,843,905 A | 12/1998 | Singh et al. |

(Continued)

FOREIGN PATENT DOCUMENTS

| | | |
|---|---|---|
| AU | A-73636/91 | 10/1991 |
| DE | 4219626 A1 | 12/1993 |
| EP | 0 036 676 B2 | 9/1981 |
| EP | 0 058 481 B2 | 8/1982 |
| EP | 0 133988 A2 | 3/1985 |
| EP | 0 143 949 B1 | 6/1985 |
| EP | 0 220 063 A2 | 4/1987 |
| EP | 0 267 611 B1 | 5/1988 |
| EP | 0 308 378 B1 | 3/1989 |
| EP | 0 364 778 B1 | 4/1990 |

(Continued)

OTHER PUBLICATIONS

Huang Z., Pharmacology and Therapeutics, 2000, 86: 201-215.*
Cohen et al., Arthritis and Rheumatism, 2002, 46: 614-624.*
Aguet et al., "Various human interferon αsubclasses cross-react with common receptors: their binding affinities correlate with their specific biological activities," *Virology*, 132:211-216 (1984).
Akiba et al., "CD28-independent costimulation of T cells by OX40 ligand and CD70 on activated B cells," *J. Immunol*, 162:7058-7066 (1999).

(Continued)

*Primary Examiner* — Ilia Ouspenski
(74) *Attorney, Agent, or Firm* — Patricia Anne Perkins

(57) ABSTRACT

Methods for treating an inflammatory or an immune condition are described. Methods for treating an inflammatory or an immune condition with IL-1 inhibitors and an inhibitor of B cell or T cell activation are described. Methods for treating an inflammatory or an immune condition with TNF inhibitors and an inhibitor of B cell or T cell activation are described.

15 Claims, 38 Drawing Sheets

U.S. PATENT DOCUMENTS

| | | | |
|---|---|---|---|
| 5,844,095 A | 12/1998 | Linsley et al. |
| 5,851,556 A | 12/1998 | Breton et al. |
| 5,851,795 A | 12/1998 | Linsley et al. |
| 5,853,977 A | 12/1998 | Dalie et al. |
| 5,854,003 A | 12/1998 | Rothe et al. |
| 5,856,161 A | 1/1999 | Aggarwal et al. |
| 5,859,207 A | 1/1999 | Johnson et al. |
| 5,863,926 A | 1/1999 | Christensen et al. |
| 5,866,576 A | 2/1999 | Underiner et al. |
| 5,866,616 A | 2/1999 | Christensen et al. |
| 5,869,315 A | 2/1999 | Talanian et al. |
| 5,869,511 A | 2/1999 | Cohan et al. |
| 5,869,660 A | 2/1999 | Adams et al. |
| 5,869,677 A | 2/1999 | Christensen et al. |
| 5,872,095 A | 2/1999 | Haskill et al. |
| 5,872,146 A | 2/1999 | Baxter et al. |
| 5,877,151 A | 3/1999 | Pereira |
| 5,877,180 A | 3/1999 | Linden et al. |
| 5,877,200 A | 3/1999 | Muller |
| 5,877,222 A | 3/1999 | McGrath |
| 5,886,010 A | 3/1999 | Mori et al. |
| 5,891,883 A | 4/1999 | Christensen et al. |
| 5,912,324 A | 6/1999 | Okamura et al. |
| 5,914,253 A | 6/1999 | Okamura et al. |
| 5,929,117 A | 7/1999 | Muller et al. |
| 5,932,208 A | 8/1999 | Chedid et al. |
| 5,942,607 A | 8/1999 | Freeman et al. |
| 5,948,638 A | 9/1999 | Lin et al. |
| 5,952,320 A | 9/1999 | Davidsen et al. |
| 5,955,435 A | 9/1999 | Baxter et al. |
| 5,955,476 A | 9/1999 | Muller et al. |
| 5,955,480 A | 9/1999 | Chang |
| 5,962,481 A | 10/1999 | Levin et al. |
| 5,965,564 A | 10/1999 | Bianco et al. |
| 5,981,724 A | 11/1999 | Armitage et al. |
| 5,990,119 A | 11/1999 | Christensen et al. |
| 5,994,351 A | 11/1999 | Robinson et al. |
| 6,025,376 A | 2/2000 | Laurent et al. |
| 6,040,327 A | 3/2000 | De Nanteuil et al. |
| 6,054,487 A | 4/2000 | Sekut et al. |
| 6,060,283 A | 5/2000 | Okura et al. |
| 6,090,382 A | 7/2000 | Salfeld et al. |
| 6,242,566 B1 | 6/2001 | Godfrey et al. |
| 6,258,562 B1 | 7/2001 | Salfeld et al. |
| 6,294,170 B1 | 9/2001 | Boone et al. |
| 6,312,700 B1 | 11/2001 | Weinberg et al. |
| 6,333,035 B1 | 12/2001 | Sugamura et al. |
| 6,344,457 B1 | 2/2002 | Jeanpetit et al. |
| 6,344,464 B1 | 2/2002 | Bourrie et al. |
| 6,355,779 B1 | 3/2002 | Goodwin et al. |
| 6,440,693 B1 | 8/2002 | Hauptmann et al. |
| 6,445,283 B1 | 9/2002 | Pang et al. |
| 6,492,370 B1 | 12/2002 | Mita et al. |
| 6,528,055 B2 | 3/2003 | Godfrey et al. |
| 6,528,623 B2 | 3/2003 | Godfrey et al. |
| 6,566,082 B1 | 5/2003 | Weinberg et al. |
| 7,098,184 B2 | 8/2006 | Godfrey et al. |
| 7,125,670 B2 | 10/2006 | Godfrey et al. |
| 7,148,061 B2 | 12/2006 | Lenardo et al. |
| 7,291,331 B1 | 11/2007 | Croft et al. |
| 2003/0064480 A1 | 4/2003 | Lauffer et al. |
| 2004/0080919 A1 | 4/2004 | Behammer |

FOREIGN PATENT DOCUMENTS

| | | |
|---|---|---|
| EP | 0 398 327 B1 | 11/1990 |
| EP | 0 412 486 B1 | 2/1991 |
| EP | 0 418 014 B1 | 3/1991 |
| EP | 0 422 339 B1 | 4/1991 |
| EP | 0 433 900 B1 | 6/1991 |
| EP | 0 445 228 B1 | 9/1991 |
| EP | 0 512 528 B1 | 11/1992 |
| EP | 0 526 905 A2 | 2/1993 |
| EP | 0 526 905 A3 | 2/1993 |
| EP | 0 534 978 B1 | 4/1993 |
| EP | 0 542 795 B1 | 5/1993 |
| EP | 0 550 376 A1 | 7/1993 |
| EP | 0 568 928 B1 | 11/1993 |
| EP | 0 614 984 B1 | 9/1994 |
| EP | 0 623 674 A1 | 11/1994 |
| EP | 0 648 783 B1 | 4/1995 |
| EP | 0 663 210 A2 | 7/1995 |
| EP | 0 663 210 A3 | 7/1995 |
| EP | 0 664 128 A1 | 7/1995 |
| EP | 0 712 931 B1 | 5/1996 |
| EP | 0 731 791 B1 | 9/1996 |
| EP | 0 741 707 B1 | 11/1996 |
| EP | 0 818 439 B1 | 1/1998 |
| EP | 0 850 952 A1 | 7/1998 |
| EP | 0 853 083 B1 | 7/1998 |
| EP | 0 855 404 A1 | 7/1998 |
| EP | 0 864 585 A1 | 9/1998 |
| EP | 0 880 970 A1 | 12/1998 |
| EP | 0 882 714 A1 | 12/1998 |
| EP | 0 895 988 B1 | 2/1999 |
| EP | 0 939 121 B1 | 9/1999 |
| EP | 0 943 616 A1 | 9/1999 |
| EP | 0 962 531 A2 | 12/1999 |
| EP | 0 962 531 A3 | 12/1999 |
| EP | 0 974 600 A2 | 1/2000 |
| EP | 0 974 600 A3 | 1/2000 |
| EP | 1 008 346 A1 | 6/2000 |
| EP | 1 110 969 A1 | 6/2001 |
| FR | 2706772 | 12/1994 |
| GB | 2 218 101 A | 11/1989 |
| GB | 2 246 569 A | 2/1992 |
| GB | 2 326 881 A | 1/1999 |
| JP | 10130149 A2 | 5/1998 |
| JP | 10147531 A2 | 6/1998 |
| JP | 10231285 A2 | 9/1998 |
| JP | 10259140 A2 | 9/1998 |
| JP | 10316570 A2 | 12/1998 |
| JP | 11001481 A | 1/1999 |
| WO | WO 88/01649 | 3/1988 |
| WO | WO 90/05541 | 5/1990 |
| WO | WO 90/06371 | 6/1990 |
| WO | WO 91/03553 | 3/1991 |
| WO | WO 91/08285 | 6/1991 |
| WO | WO 91/17184 | 11/1991 |
| WO | WO 91/17249 | 11/1991 |
| WO | WO 92/00092 | 1/1992 |
| WO | WO 92/01002 | 1/1992 |
| WO | WO 92/13095 | 8/1992 |
| WO | WO 92/16221 | 10/1992 |
| WO | WO 93/00431 | 1/1993 |
| WO | WO 93/07863 | 4/1993 |
| WO | WO 93/08207 | 4/1993 |
| WO | WO 93/15722 | 8/1993 |
| WO | WO 93/19767 | 10/1993 |
| WO | WO 93/19777 | 10/1993 |
| WO | WO 93/21259 | 10/1993 |
| WO | WO 93/21946 | 11/1993 |
| WO | WO 93/24135 | 12/1993 |
| WO | WO 94/02627 | 2/1994 |
| WO | WO 94/05691 | 3/1994 |
| WO | WO 94/06457 | 3/1994 |
| WO | WO 94/20069 | 9/1994 |
| WO | WO 94/20517 | 9/1994 |
| WO | WO 94/21235 | 9/1994 |
| WO | WO 94/26290 | 11/1994 |
| WO | WO 94/28912 | 12/1994 |
| WO | WO 95/01997 | 1/1995 |
| WO | WO 95/04045 | 2/1995 |
| WO | WO 95/09653 | 4/1995 |
| WO | WO 95/34326 | 12/1995 |
| WO | WO 96/09323 | 3/1996 |
| WO | WO 96/11209 | 4/1996 |
| WO | WO 96/12735 | 5/1996 |
| WO | WO 96/20926 | 7/1996 |
| WO | WO 96/22793 | 8/1996 |
| WO | WO 96/23067 | 8/1996 |
| WO | WO 96/25861 | 8/1996 |
| WO | WO 96/28546 | 9/1996 |
| WO | WO 96/32478 | 10/1996 |
| WO | WO 96/33172 | 10/1996 |
| WO | WO 96/35711 | 11/1996 |
| WO | WO 96/38150 | 12/1996 |

| | | |
|---|---|---|
| WO | WO 96/40907 | 12/1996 |
| WO | WO 96/40918 | 12/1996 |
| WO | WO 96/40958 | 12/1996 |
| WO | WO 97/08174 | 3/1997 |
| WO | WO 97/11668 | 4/1997 |
| WO | WO 97/12244 | 4/1997 |
| WO | WO 97/12902 | 4/1997 |
| WO | WO 97/18207 | 5/1997 |
| WO | WO 97/23457 | 7/1997 |
| WO | WO 97/24441 | 7/1997 |
| WO | WO 97/28267 | 8/1997 |
| WO | WO 97/28828 | 8/1997 |
| WO | WO 97/34631 | 9/1997 |
| WO | WO 97/37973 | 10/1997 |
| WO | WO 97/37974 | 10/1997 |
| WO | WO 97/43250 | 11/1997 |
| WO | WO 97/47599 | 12/1997 |
| WO | WO 98/01555 | 1/1998 |
| WO | WO 98/17661 | 4/1998 |
| WO | WO 98/21957 | 5/1998 |
| WO | WO 98/24463 | 6/1998 |
| WO | WO 98/30541 | 7/1998 |
| WO | WO 98/32733 | 7/1998 |
| WO | WO 98/33513 | 8/1998 |
| WO | WO 98/38859 | 9/1998 |
| WO | WO 98/39315 | 9/1998 |
| WO | WO 98/39316 | 9/1998 |
| WO | WO 98/39326 | 9/1998 |
| WO | WO 98/39329 | 9/1998 |
| WO | WO 98/39361 | 9/1998 |
| WO | WO 98/41232 | 9/1998 |
| WO | WO 98/42325 | 10/1998 |
| WO | WO 98/42659 | 10/1998 |
| WO | WO 98/43946 | 10/1998 |
| WO | WO 98/43959 | 10/1998 |
| WO | WO 98/44940 | 10/1998 |
| WO | WO 98/45268 | 10/1998 |
| WO | WO 98/47892 | 10/1998 |
| WO | WO 98/51665 | 11/1998 |
| WO | WO 98/52937 | 11/1998 |
| WO | WO 98/52948 | 11/1998 |
| WO | WO 98/53842 | 12/1998 |
| WO | WO 98/56377 | 12/1998 |
| WO | WO 98/56756 | 12/1998 |
| WO | WO 98/56788 | 12/1998 |
| WO | WO 98/57936 | 12/1998 |
| WO | WO 98/58965 | 12/1998 |
| WO | WO 99/00363 | 1/1999 |
| WO | WO 99/00364 | 1/1999 |
| WO | WO 99/01139 | 1/1999 |
| WO | WO 99/01449 | 1/1999 |
| WO | WO 99/02510 | 1/1999 |
| WO | WO 99/03837 | 1/1999 |
| WO | WO 99/04793 | 2/1999 |
| WO | WO 99/06041 | 2/1999 |
| WO | WO 99/06042 | 2/1999 |
| WO | WO 99/06410 | 2/1999 |
| WO | WO 99/06426 | 2/1999 |
| WO | WO 99/07679 | 2/1999 |
| WO | WO 99/07704 | 2/1999 |
| WO | WO 99/08688 | 2/1999 |
| WO | WO 99/09022 | 2/1999 |
| WO | WO 99/09063 | 2/1999 |
| WO | WO 99/09965 | 3/1999 |
| WO | WO 99/22760 | 5/1999 |
| WO | WO 99/36415 | 7/1999 |
| WO | WO 99/36426 | 7/1999 |
| WO | WO 99/36541 | 7/1999 |
| WO | WO 99/37625 | 7/1999 |
| WO | WO 99/37772 | 7/1999 |
| WO | WO 99/37773 | 7/1999 |
| WO | WO 99/37818 | 7/1999 |
| WO | WO 99/46248 | 9/1999 |
| WO | WO 99/47154 | 9/1999 |
| WO | WO 99/47545 | 9/1999 |
| WO | WO 99/47672 | 9/1999 |
| WO | WO 99/58674 | 11/1999 |
| WO | WO 00/24782 | 5/2000 |
| WO | WO 00/47740 | 8/2000 |
| WO | WO 00/67034 | 11/2000 |
| WO | WO 01/39722 A2 | 6/2001 |
| WO | WO 01/85782 A2 | 11/2001 |
| WO | WO 01/87977 A2 | 11/2001 |
| WO | WO 01/92337 A2 | 12/2001 |
| WO | WO 02/02638 A2 | 1/2002 |
| WO | WO 02/02638 A3 | 1/2002 |
| WO | WO 02/092620 A2 | 11/2002 |
| WO | WO 02/096461 A1 | 12/2002 |

OTHER PUBLICATIONS

Al-Janadi et al., "Cytokine profile in systemic lupus erythematosus, rheumatoid arthritis, and other rheumatic diseases," *J. Clin. Immunology*, 13:58-67 (1993).

Aruffo et al., "Molecular cloning of a CD28 cDNA by a high-efficiency COS cell expression system," *Proc. Natl. Acac. Sci. USA*, 84:8573-8579 (1987).

Auricchio et al., "Isolation of highly infectious and pure adeno-associated virus type 2 vectors with a single-step gravity-flow column," *Human Gene Therapy*, 12:71-76 (2001).

Ausubel et al., eds., *Current Protocols in Molecular Biology*, vols. 1, 2, 3 and 4, John Wiley & Sons, Inc. (1999) Table of Contents.

Bach et al., "The IFNγreceptor: a paradigm for cytokine receptor signaling," *Annu. Rev. Immunol.*, 15:563-591 (1997).

Barrera et al., "Effects of antiheumatic agents on cytokines," *Seminars in Arthritis and Rheumatism*, 25:234-253 (1996).

Bendele et al., "Combination benefit of treatment with the cytokine inhibitors interleukin-1 receptor antagonist and PEGylated soluble tumor necrosis factor receptor type I in animal models of rheumatoid arthritis," *Arthritis & Rheumatism*, 43:2648-2659 (2000).

Bischoff et al., "Preliminary model for methotrexate pharmacokinetics," *J. Pharm. Sci.*, 59(2):149-154 (1970).

Blazar et al., "Infusion of Anti-B7.1 (CD80) and Anti-B7.2 (CD86) Monoclonal Antibodies Inhibits Murine Graft-Versus-Host Disease Lethality in Part Via Direct Effects on $CD4^+$ and $CD8^+T$ Cells," *J. Immunol.*, 157: 3250-3259 (1996).

Boulianne et al., "Production of functional chimaeric mouse/human antibody," *Nature*, 312: 643-646 (1984).

Bowie et al., "A method to identify protein sequences that fold into a known three-dimensional structure," *Science*, 253:164-170 (1991).

Brenner et al., "Population statistics of protein structures: lessons from structural classifications," *Curr. Opn. Struct. Biol.*, 7:369-376 (1997).

Brodeur et al., "Mouse-human myeloma partners for the production of heterohybridmas," *Production of Heterohybridomas*, Ch. 4, pp. 51-63, Marcel Dekker, Inc., (1987).

Brody et al., "Mechanism of action of methotrexate: experimental evidence that methotrexate blocks the binding of interleukin-1β to the interleukin-1 receptor on target cells," *Eur. J. Clini. Chem. Clin. Biochem.*, 31:667-674 (1993).

Brüggemann et al., "Designer mice: the production of human antibody repertoires in transgenic animals," *Year in Immunol.*, 7:33-40 (1993).

Brunet et al., "A new member of the immunoglobulin superfamily—CTLA-4," *Nature*, 328:267-270 (1987).

Buschle et al., "Interferon αinhibits apoptotic cell death in B cell chronic lymphocytic leukemia," *J. Exp. Med.*, 177:213-218 (1993).

Cabilly et al., "Generation of antibody activity from immunoglobulin polypeptide chains produced in *Escherichia coli*," *Proc. Natl. Acad. Sci. USA*, 81:3273-3277 (1984).

Camerini et al., "The T cell activation antigen CD27 is a member of the nerve growth factor/tumor necrosis factor receptor gene family," *J. Immunol.*, 147:3165-3169 (1991).

Chothia et al., "Canonical structures for the hypervariable regions of immunoglobulins," *J. Mol. Biol.*, 196:901-917 (1987).

Chothia et al., "Conformations of immunoglobulin hypervariable regions," *Nature*, 342:877-883 (1989).

Chou et al., "Conformational parameters for amino acids in helical, β-Sheet, and random coil regions calculated from proteins," *Biochemistry*, 13:211-222 (1974).

Chou et al., "Prediction of protein confirmation," *Biochemistry*, 13:222-245 (1974).

Coligan et al., eds., *Current Protocols in Immunology*, vols. 1, 2, and 3, John Wiley & Sons, Inc., (1997) Table of Contents.
Condit et al., "Studies on the folic acid vitamins," *Cancer*, 13:222-249 (1960).
Dinarello et al., "Overview of interleukin-18: more than an interferon-γ inducing factor," *J. Leukocyte Biol.*, 63:658-664 (1998).
Dürkop et al., "Molecular cloning and expression of a new member of the nerve growth factor receptor family that is characteristic for Hodgkin's disease," *Cell*, 68:421-427 (1992).
Du Pasquier, "Evolution of the Immune System," *Fundamental Immunology*, Second Edition, Paul, ed., Raven Press, Ch. 7, p. 139-165 (1989).
Ellison et al., "The nucleotide sequence of a human immunoglobulin $C_{\gamma 1}$ gene," *Nucl. Acids Res.*, 10:4071-9 (1982).
Emery et al., "Improvement in health-related quality of life in patients with active rheumatoid arthritis: CTLA4Ig combined with etanercept compared to etanercept plus placebo," *Arthritis Rheum.*, 46:S514, 1376, Abstract (2002).
Eppstein et al., "Biological activity of liposome-encapsulated murine interferon γis mediated by a cell membrane receptor," *Proc. Natl. Acad. Sci. USA*, 82:3688-3692 (1985).
Evans et al., "Design of nonpeptidal ligands for a peptide receptor: cholecystokinin antagonists," *J. Med. Chem.*, 30:1229-1239 (1987).
Evans, "Methotrexate," *Applied Pharmacokinetics*, Evans, ed., Ch. 16 pp. 518-548 (1980).
Faggioni et al., "Leptin-deficient (*ob/ob*) mice are protected from T cell-mediated hepatotoxicity: role of tumor necrosis factor α and IL-18," *Proc. Natl. Acad. Sci. USA*, 97:2367-2372 (2000).
Farrar et al., "The molecular cell biology of interferon-γand its receptor," *Annu. Rev. Immunol.*, 11:571-611 (1993).
Fauchère, "Elements for the rational design of peptide drugs," *Adv. Drug Res.*, 15:29-69 (1986).
Feldmann et al., "Anti-TNFα therapy of rheumatoid arthritis: What have we learned?," *Annu. Rev. Immunol.*, 19:163-196 (2001).
Freeman, "The flourometric measurement of the absorption, distribution and excretion of single does of 4-amino-10-methly pteroylglutamic acid (amethopterin) in man," J. Pharmacol. Exp. Ther., 122:154-162 (1958).
Freeman et al., "B7, a new member of the Ig superfamily with unique expression on activated and neoplastic B cells," *J. Immunol.*, 143:2714-2722 (1989).
Freeman et al., "Cloning of B7-2: A CTLA-4 counter-receptor that costimulates human T cell proliferation," *Science*, 262:909-911 (1993).
Funauchi et al., "Serum level of interferon-γin autoimmune disease," *Tohoku J. Exp. Med.*, 164:259-267 (1991).
Furst, "Clinical pharmacology of very low dose methotrexate for use in rheumatoid arthritis," *J. Rheumatol. Suppl.*, 12:11-14 (1985).
Gennaro, ed., *Remington's Pharmaceutical Sciences*, 18th Edition, Mack Publishing Company (1990) Table of Contents.
Gómez-Foix et al., "Adenovirus-mediated transfer of the muscle glycogen phosphorylase gene into hepatocytes confers altered regulation of glycogen metabolism," *J. Biol. Chem.* 267:25129-25134 (1992).
Grawunder et al., "Interferon-γarrests proliferation and causes apoptosis in stromal cell/interleukin-7-dependent normal murine pre-B cell lines and clones in vitro, but does not induce differentiation to surface immunoglobulin-positive B cells," *Eur. J. Immunol.*, 23:544-551 (1993).
Gribskov et al., "Profile analysis: detection of distantly related proteins," *Proc. Nat. Acad. Sci. USA*, 84:4355-4358 (1987).
Gribskov et al., "Profile analysis," *Meth. Enzym.*, 183:146-159 (1990).
Grosschedl et al., "Introduction of a μ immunoglobulin gene into the mouse germ line: specific expression in lymphoid cells and synthesis of functional antibody," *Cell*, 38: 647-658 (1984).
Hanahan, "Heritable formation of pancreatic β-cell tumours in transgenic mice expressing recombinant insulin/simian virus 40 oncogenes," *Nature*, 315:115-122 (1985).
Harlow et al., *Antibodies: A Laboratory Manual*, Cold Spring Harbor Laboratory Press (1988) Table of Contents.
Hague et al., "Signal transduction in the interferon system," *Semin. Oncol.*, 25(suppl 1):14-22 (1998).
Haraoui et al., "Biologic agents in the treatment of rheumatoid arthritis," *Current Pharmaceutical Biotechnology*, 1:217-233 (2000).
Henderson et al., "The metabolic fate of tritiated methotrexate," *Cancer Res.*, 25:1008-1017 (1965).
Herz et al., "Adenovirus-mediated transfer of low density lipoprotein receptor gene acutely accelerates cholesterol clearance in normal mice," *Proc. Natl. Acad. Sci.* 90:2812-2816 (1993).
Hoffmeister, "Methotrexate therapy in rhematoid arthritis: 15 years experience," *Am. J. Med.*, 30:69-73 (1993).
Holm et al., "Protein folds and families: sequence and structure alignments," *Nucl. Acid. Res.*, 27:244-247 (1999).
Hoogenboom et al., "By-passing immunization: Human antibodies from synthetic repertoires of germline $V_H$ gene segments rearranged in vitro," *J. Mol. Biol.*, 227:381-388 (1992).
Huang, Z., "Structural chemistry and therapeutic intervention of protein-protein interactions in immune response, human immunodeficiency virus entry, and apoptosis," *Pharmacology & Therapeutics*, 86:201-215 (2000).
Isaacs et al., "Virus interference. I. The interferon," *Proc. R. Soc.*, 147:258-267 (1957).
Jaffe, "On the treatment of rheumatoid arthritis with M&Ms (Motrin & methotrexate)," *Arthritis and Rheumatism*, 31:299 (1988).
Jakobovits et al., "Analysis of homozygous mutant chimeric mice: deletion of the immunoglobulin heavy-chain joining region blocks B-cell development and antibody production," *Proc. Natl. Acad. Sci.*, 90:2551-2555 (1993).
Jakobovits et al., "Germ-line transmission and expression of a human-derived yeast artificial chromosome," *Nature*, 362:255-258 (1993).
Jolivet et al., "The pharmacology and clinical use of methotrexate," *N. Eng. J. Med.*, 309:1094-1104 (1983).
Jonasch et al. "Interferon in oncological practice: review of interferon biology, clinical applications, and toxicities," *Oncologist*, 6:34-55 (2001).
Jones et al., "Replacing the complementarity-determining regions in a human antibody with those from a mouse," *Nature*, 321:522-525 (1986).
Jones, "Progress in protein structure prediction," *Curr. Opin. Struct. Biol.*, 7:377-387 (1997).
Kabat et al., *Sequences of Proteins of Immunological Interest*, Fifth Edition, U.S. Department of Health and Human Services, (1991) Table of Contents.
Khare et al., "Oral administration of an immunodominant human collagen peptide modulates collagen-induced arthritis," *J. Immunol.*, 155:3653-3659 (1995).
Khare et al., "Spontaneous inflammatory disease in HLA-B27 transgenic mice is independent of MHC class II molecules: a direct role for B27 heavy chains and not B27-derived peptides," *J. Immunol.*, 160:101-106 (1998).
Khare et al., "Severe B cell hyperplasia and autoimmune disease in TALL-1 transgenic mice," *Proc. Natl. Acad. Sci. USA*, 97:3370-3375 (2000).
Kranz et al., "Restricted reassociation of heavy and light chains from hapten-specific monoclonal antibodies," *Proc. Natl. Acad. Sci. USA*, 78:5807-5811 (1981).
Langer et al., "Biocompatibility of polymeric delivery systems for macromolecules," *J. Biomed. Mater. Res.*, 15:267-277 (1981).
Langer, "Controlled release of macromolecules," *ChemTech*, 12:98-105 (1982).
Laughlin et al., "Cloning of infectious adeno-associated virus genomes in bacterial plasmids," *Gene*, 23:65-73 (1983).
LaPlanche et al., "Phosphorothioate-modified oligdeoxyribonucleotides. III. NMR and UV spectroscopic studies of the $R_p$-$R_p$, $S_p$-$S_p$ and $R_p$-$S_p$ duplexes, [d (GG$_s$ AATTCC]$_2$ derived from diastereomeric O-ethyl phosphorothioates," *Nucl. Acids Res.*, 14:9081-9093 (1986).
Lesk, ed., *Computational Molecular Biology*, Oxford University Press (1988) Table of Contents.
Lewis et al., "Use of a novel mutagenesis strategy, optimized residue substitution, to decrease the off-rate of an anti-gp120 antibody," *Mol. Immunol.*, 32:1065-1072 (1995).
Lim et al., "Urine neopterin as a parameter of disease activity in patients with systemic lupus erythematosus: comparisons with serum sIL-2R and antibodies to dsDNA, erythrocyte sedimentation rate, and plasma C3, C4, and C3 degradation products," *Ann. Rheum. Dis.*, 52:429-435 (1993).
Linsley et al., "Binding of the B cell activation antigen B7 to CD28 costimulates T cell proliferation and interleukin 2 mRNA accumulation," *J Exp. Med.*, 173:721-730 (1991).
Liu et al., "Chimeric mouse-human IgG1 antibody that can mediate lysis of cancer cells," *Proc. Natl. Acad. Sci. USA*, 84:3439-3443 (1987).
Lorenz et al., "Biological agents: a novel approach to the therapy of rheumatoid arthritis," *Exp. Opin. Invest. Drugs*, 9:1479-1490 (2000).
Lu et al., "Effects of virus expressing CTLA4-IG and IL1-RA on islet Xenografts," *Transplantation Proceedings*, 33:713-714 (2001).
MacLennan et al., "Structure-function relationships in the $Ca^{2+}$-binding and translocation domain of SERCA1: physiological correlates in Brody disease," *Acta Physiol. Scand. Suppl.*, 643:55-67 (1998).
Marks et al., "By-passing immunization: building high affinity human antibodies by chain shuffling," *Biotechnology*, 10:779-783 (1992).
Marks et al., "By-passing immunization: human antibodies from V-gene libraries displayed on phage," *J. Mol. Biol.*, 222:581-597 (1991).
Marston et al., "Solubilization of protein aggregates," *Meth. Enz.*, 182:264-276 (1990).
Masutani et al., "Predominance of Th1 immune response in diffuse proliferative lupus nephritis," *Arthritis & Rheumatism*, 44:2097-2106 (2001).
Merlin et al., "$^{125}$I-labelled human interferons alpha, beta and gamma: comparative receptor-binding data," *J. Gen. Virol.*, 66:1149-1152 (1985).
Miura et al., "Molecular cloning and characterization of a novel glycoprotein, gp34, that is specifically induced by the human T-cell leukemia virus type I transactivator $p40^{tax}$," *Mol. Cell Biol.* 11:1313:1325 (1991).
Moreland et al., "Biological agents for treating rheumatoid arthritis," *Arthritis & Rheumatism*, 40:397-409 (1997).
Morgan et al., "Folate status of rheumatoid arthritis patients receiving long-term, low dose methotrexate therapy," *Arthritis & Rheumatism*, 30:1348-1356 (1987).
Morrison et al., "Chimeric human antibody molecules: mouse antigen-binding domains with human constant region domains," *Proc. Natl. Acad. Sci. USA*, 81:6851-6855 (1984).
Moult, "The current state of art in protein structure prediction," *Curr. Opin. Biotech.*, 7:422-427 (1996).
Müller, "Determination of affinity and specificity of anti-hapten antibodies by competitive radioimmunoassay," *Meth. Enzymol.*, 92:589-601 (1983).
Nabozny et al., "Identification of a cyanogen bromide fragment of porcine type II collagen capable of modulating collagen arthritis in B10.RIII(H-$2^r$) mice," *Autoimmunity*, 20:39-49 (1995).
Nakashima et al., "The combination of polymorhisms within interferon-γreceptor 1 and receptor 2 associated with the risk of systemic lupus erythematosus," *FEBS Lett.*, 453:187-190 (1999).
Narumi et al., "Serum levels of INF-inducible protein-10 relating to the activity of systemic lupus erythematosus," *Cytokine*, 12:1561-1565 (2000).
Neuberger et al., "Recombinant antibodies possessing novel effector functions," *Nature*, 312:604-608 (1984).
Neuberger et al., "A hapten-specific chimaeric IgE antibody with human physiological effector function," *Nature*, 314:268-270 (1985).
Novelli et al., "Environmental signals influencing expression of the IFN-γreceptor on human T cells control whether IFN-γpromotes proliferation or apoptosis," *J. Immunol.* 152:496-504 (1994).
Perhala et al., "Local infectious complications following large joint replacement in rheumatoid arthritis patients treated with methotrexate versus those not treated with methotrexate," *Arthritis and Rheumatism*, 34:146-152 (1991).
Pestka, "The human interferon-alpha species and hybrid proteins," *Seminars Oncol.*, 24:S9-4-S9-17 (1997).
Pfeffer et al., "Biological properties of recombinant α-interferons: $40^{th}$ anniversary of the discovery of interferons," *Cancer Res.*, 58: 2489-2499 (1998).
Readhead et al., "Expression of a myelin basic protein gene in transgenic shiverer mice: correction of the dysmyelinating phenotype," *Cell*, 48:703-712 (1987).
Riechmann et al., "Reshaping human antibodies for therapy," *Nature*, 332:323-327 (1988).
Rodenhuis et al., "Increase of dihydrofolate reductase in peripheral blood lymphocytes of rheumatoid arthritis patients treated with low-dose oral methotrexate," *Arthritis and Rheumatism*, 30:369-374 (1987).
Rojas et al., "Inhibition of apoptotic cell death in B-CLL by interferon gamma correlates with clinical stage," *Leukemia*, 10:1782-1788 (1996).
Rozzo et al., "Evidence for an interferon-inducible gene, Ifi202, in the susceptibility to systemic lupus," *Immunity*, 15:435-443 (2001).
Sambrook et al., *Molecular Cloning: A Laboratory Manual*, Cold Spring Harbor Laboratory Press (1989) Table of Contents.
Samsonov et al., "Serum soluble markers of immune activation and disease activity in systemic lupus erythematosus," *Lupus*, 4:29-32 (1995).
Sasaki et al., "Structure-mutation analysis of the ATPase site of *Dictyostelium discoideum* myosin II," *Adv. Biophys*, 35:1-24 (1998).
Schindler et al., "Transcriptional responses to polypeptide ligands: the JAK-STAT pathway," *Annu. Rev. Biochem*, 64:621-651 (1995).
Seeger et al., "Analogs of pteroylglutamic acid. III. 4-Amino derivatives," *J. Am. Chem. Soc.*, 71: 1753-1755 (1949).
Segal et al., "Methotrexate: mechanism of action in rheumatoid arthritis," *Seminars in Arthritis and Rheumatism*, 20:190-198 (1990).
Seitz et al., "Methotrexate action in rheumatoid arthritis: stimulation of cytokine inhibitor and inhibition of chemokine production by peripheral blood mononuclear cells," *Br. J. Rheumatology*, 34:602-609 (1995).
Sidman et al., "Controlled release of macromolecules and pharmaceuticals from synthetic polypeptides based on glutamic acid," *Biopolymers*, 22:547-556 (1983).
Smith et al., "A receptor for tumor necrosis factor defines an unusual family of cellular and viral proteins," *Science*, 248:1019-1023 (1990).
Smith, ed., *Biocomputing: Informatics and Genome Projects*, Academic Press (1994) Table of Contents.
Sperling et al., "Acute and chronic suppression of leukotriene $B_4$ synthesis ex vivo in neutrophils from patients with rheumatoid arthritis beginning treatment with methotrexate," *Arthritis and Rheumatism*, 35:376-384 (1992).
Stamenkovic et al., "A B-lymphocyte activation molecule related to the nerve growth factor receptor and induced by cytokines in carcinomas," *EMBO J.*, 8:1403-1410 (1989).
Stuart et al., "Monkeying Around with Collagen Autoimmunity and Arthritis," *Laboratory Investigation*, 54(1):1-3 (1986).
Ternowitz et al., "Methotrexate inhibits the human C5a-induced skin response in patients with psoriasis," *J. Inv. Derm.*, 89:192-196 (1987).
Theofilopoulos et al., "Murine models of systemic lupus erythematosus," *Adv. Immunol.*, 37:269-390 (1985).
Theofilopoulos et al., "The role of IFN-γin systemic lupus erythematosus: a challenge to the Th1/Th2 paradigm in autoimmunity," *Arthritis Res.* 3:136-141 (2001).
Totsuka et al., "Therapeutic effect of anti-OX40L and anti-TNF-α MAbs in a murine model of chronic colitis," *Am. J. Physiol. Gastrointest. Liver Physiol.*, 284:G595-G603 (2003).
Uhlmann et al., "Antisense oligonucleotides: a new therapeutic principle," *Chemical Reviews*, 90: 543-584 (1990).
Van de Kerkhof et al., "Methotrexate inhibits the leukotriene $B_4$ induced intraepidermal accumulation of polymorphonuclear leukocytes," *Brit. J. Derm.*, 113:251a-255a (1985).
Veber et al., "The design of metabolically-stable peptide analogs," *TINS*, 8: 392-396 (1985).
Verhoeyen et al., "Reshaping human antibodies: grafting an antilysozyme activity," *Science*, 239: 1534-1536 (1988).
von Büow et al., "NF-AT activation induced by a CAML-interacting member of the tumor necrosis factor receptor superfamily," *Science*, 278:138-140 (1997).
Vyse et al., "Genetic susceptibility to systemic lupus erythematosus," *Ann. Rev. Immunol.*, 16:261-292 (1998).

Wahl et al., "Improved radioimaging and tumor localization with monoclonal F(ab')₂," *J. Nucl. Med.*, 24:316-325 (1983).

Weinberg et al., "Antibodies to OX-40 (CD134) can identify and eliminate autoreactive T cells: implications for human autoimmune disease," *Molecular Medicine Today*, 4:76-83 (1998).

Weinblatt et al., "Efficacy of low-dose methotrexate in rheumatoid arthritis," *N. Eng. J. Med.*, 312:818-822 (1985).

Weinblatt et al., "A pilot, multi-center, randomized, double-blind, placebo controlled of a co-stimulation blocker CTLA4-Ig (2 mg/kg) given monthly in combination with etanercept in active rheumatoid arthritis," *Arthritis Rheum.*, 46:S204, 464, Abstract (2002).

Williams et al., "Comparison of low-dose oral pulse methotrexate and placebo in the treatment of rheumatoid arthritis," *Arthritis Rheum.*, 28:721-730 (1985).

Williams et al., "Synergy between anti-CD4 and anti-tumor necrosis factor in the amelioration of established collagen-induced arthritis," *Proc. Natl. Acad. Sci. USA*, 91:2762-2766 (1994).

Yokoyama et al., "Up-regulated MHC-class II expression and γ-IFN and solule IL-2R in lupus nephritis," *Kidney Int.*, 42:755-763 (1992).

Yoshioka et al., "Contribution of OX40/OX40 ligand interaction to the pathogenesis of rheumatoid arthritis," *Eur. J. Immunol.*, 30:2815-2823 (2000).

Zon et al., "Phosphorothioate oligonucleotides," *Oligonucleotides and Analogues: A Practical Approach*, Eckstein, ed., Oxford University Press, Ch. 4, p. 87-108 (1991).

Notification of Transmittal of International Preliminary Examination Report dated Apr. 21, 2006 for Application No. PCT/US03/41378.

International Search Report dated Jul. 18, 2005, for Application No. PCT/US03/41378.

Supplementary Partial European Search Report dated Aug. 13, 2007, in European Patent Application No. 03800236.6-2406.

Sequence Listing ABJ38344, (2003).

Office Action (Restriction Requirement) mailed Sep. 26, 2006, in U.S. Appl. No. 10/748,112.

Response to Office Action (Restriction Requirement) filed in the U.S. Patent Office on Dec. 26, 2006, in U.S. Appl. No. 10/748,112.

Office Action (Restriction Requirement) mailed Mar. 1, 2007, in U.S. Appl. No. 10/748,112.

Response to Office Action (Restriction Requirement) filed in the U.S. Patent Office on Jun. 1, 2007, in U.S. Appl. No. 10/748,112.

Office Action (Restriction Requirement) mailed Jul. 5, 2007, in U.S. Appl. No. 10/748,112.

Response to Office Action (Restriction Requirement) filed in the U.S. Patent Office on Nov. 5, 2007, in U.S. Appl. No. 10/748,112.

Office Action mailed Feb. 20, 2008, in U.S. Appl. No. 10/748,112.

* cited by examiner

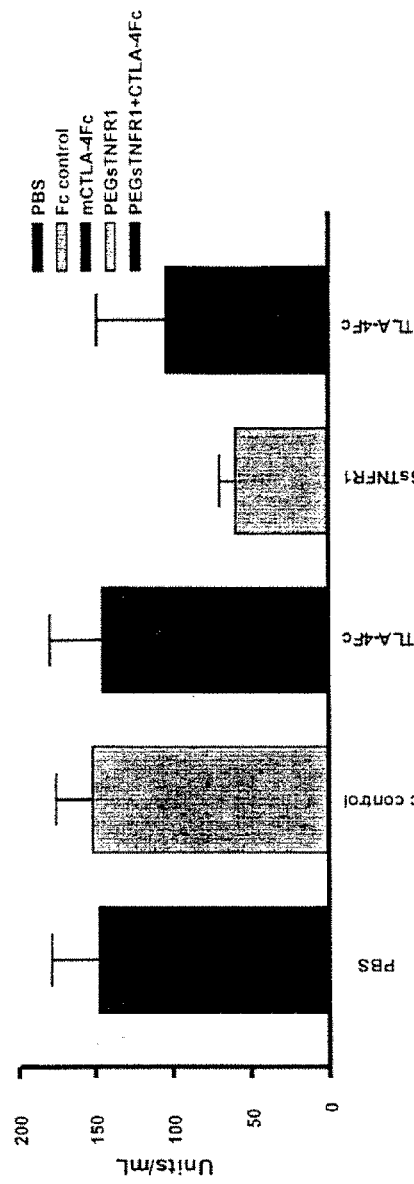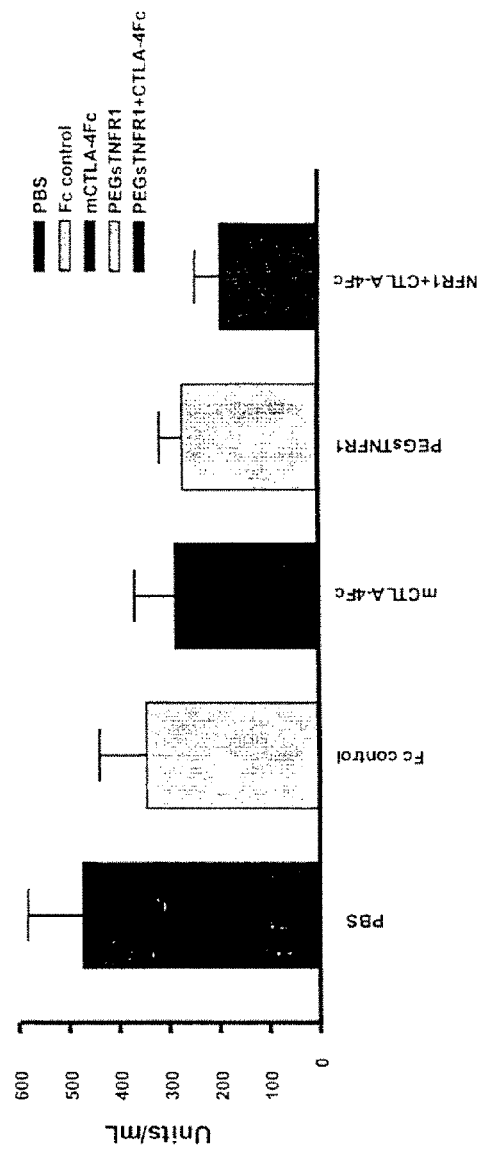

Figure 19
AGP-3 Peptibody Sequence

```
MLPGCKWDLL IKQWVCDPLG SGSATGGSGS TASSGSGSAT HMLPGCKWDL
LIKQWVCDPL GGGGGVDKTH TCPPCPAPEL LGGPSVFLFP PKPKDTLMIS
RTPEVTCVVV DVSHEDPEVK FNWYVDGVEV HNAKTKPREE QYNSTYRVVS
VLTVLHQDWL NGKEYKCKVS NKALPAPIEK TISKAKGQPR EPQVYTLPPS
RDELTKNQVS LTCLVKGFYP SDIAVEWESN GQPENNYKTT PPVLDSDGSF
FLYSKLTVDK SRWQQGNVFS CSVMHEALHN HYTQKSLSLS PGK (SEQ ID NO. 1)
```

Figure 20
CTLA4 amino acid sequence

MHVAQPAVV LASSRGIASF VCEYASPGKA TEVRVTVLRQ ADSQVTEVCA

ATYMMGNELT FLDDSICTGT SSGNQVNLTI QGLRAMDTGL YICKVELMYP

PPYYLGIGNG TQIYVIDPEP CPDSDFLLWI LAAVSSGLFF YSFLLTAVSL

SKMLKKRSPL TTGVYVKMPP TEPECEKQFQ PYFIPIN (SEQ ID NO. 2)

FIGURE 21
KIN2 Sequence

```
    ATGCGACCGTCCGGCCGTAAGAGCTCCAAAATGCAGGCTTTCCGTATCTGGGACGTTAAC
1   ------------------------------------------------------------+ 60
    M  R  P  S  G  R  K  S  S  K  M  Q  A  F  R  I  W  D  V  N

CAGAAAACCTTCTACCTGCGCAACAACCAGCTGGTTGCTGGCTACCTGCAGGGTCCGAAC
61  ------------------------------------------------------------+ 120
    Q  K  T  F  Y  L  R  N  N  Q  L  V  A  G  Y  L  Q  G  P  N

GTTAACCTGGAAGAAAAAATCGACGTTGTACCGATCGAACCGCACGCTCTGTTCCTGGGT
121 ------------------------------------------------------------+ 180
    V  N  L  E  E  K  I  D  V  V  P  I  E  P  H  A  L  F  L  G

ATCCACGGTGGTAAAATGTGCCTGAGCTGCGTGAAATCTGGTGACGAAACTCGTCTGCAG
181 ------------------------------------------------------------+ 240
    I  H  G  G  K  M  C  L  S  C  V  K  S  G  D  E  T  R  L  Q

CTGGAAGCAGTTAACATCACTGACCTGAGCGAAAACCGCAAACAGGACAAACGTTTCGCA
241 ------------------------------------------------------------+ 300
    L  E  A  V  N  I  T  D  L  S  E  N  R  K  Q  D  K  R  F  A

TTCATCCGCTCTGACAGCGGCCCGACCACCAGCTTCGAATCTGCTGCTTGCCCGGGTTGG
301 ------------------------------------------------------------+ 360
    F  I  R  S  D  S  G  P  T  T  S  F  E  S  A  A  C  P  G  W

TTCCTGTGCACTGCTATGGAAGCTGACCAGCCGGTAAGCCTGACCAACATGCCGGACGAA
361 ------------------------------------------------------------+ 420
    F  L  C  T  A  M  E  A  D  Q  P  V  S  L  T  N  M  P  D  E

GGCGTGATGGTAACCAAATTCTACTTCCAGGAAGACGAAGCTGCAGCTGAACCAAAATCT
421 ------------------------------------------------------------+ 480
    G  V  M  V  T  K  F  Y  F  Q  E  D  E  A  A  A  E  P  K  S

TCCGACAAAACTCACACATGCCCACCGTGCCCAGCACCTGAACTCCTGGGGGGACCGTCA
481 ------------------------------------------------------------+ 540
    S  D  K  T  H  T  C  P  P  C  P  A  P  E  L  L  G  G  P  S

GTCTTCCTCTTCCCCCCAAAACCCAAGGACACCCTCATGATCTCCCGGACCCCTGAGGTC
541 ------------------------------------------------------------+ 600
    V  F  L  F  P  P  K  P  K  D  T  L  M  I  S  R  T  P  E  V

ACATGCGTGGTGGTGGACGTGAGCCACGAAGACCCTGAGGTCAAGTTCAACTGGTACGTG
601 ------------------------------------------------------------+ 660
    T  C  V  V  V  D  V  S  H  E  D  P  E  V  K  F  N  W  Y  V

GACGGCGTGGAGGTGCATAATGCCAAGACAAAGCCGCGGGAGGAGCAGTACAACAGCACG
661 ------------------------------------------------------------+ 720
    D  G  V  E  V  H  N  A  K  T  K  P  R  E  E  Q  Y  N  S  T

TACCGTGTGGTCAGCGTCCTCACCGTCCTGCACCAGGACTGGCTGAATGGCAAGGAGTAC
721 ------------------------------------------------------------+ 780
    Y  R  V  V  S  V  L  T  V  L  H  Q  D  W  L  N  G  K  E  Y
```

FIGURE 21 (cont.)

```
     AAGTGCAAGGTCTCCAACAAAGCCCTCCCAGCCCCCATCGAGAAAACCATCTCCAAAGCC
781  ---------+---------+---------+---------+---------+---------+ 840
      K  C  K  V  S  N  K  A  L  P  A  P  I  E  K  T  I  S  K  A

AAAGGGCAGCCCCGAGAACCACAGGTGTACACCCTGCCCCCATCCCGGGATGAGCTGACC
841  ---------+---------+---------+---------+---------+---------+ 900
      K  G  Q  P  R  E  P  Q  V  Y  T  L  P  P  S  R  D  E  L  T

AAGAACCAGGTCAGCCTGACCTGCCTGGTCAAAGGCTTCTATCCCAGCGACATCGCCGTG
901  ---------+---------+---------+---------+---------+---------+ 960
      K  N  Q  V  S  L  T  C  L  V  K  G  F  Y  P  S  D  I  A  V

GAGTGGGAGAGCAATGGGCAGCCGGAGAACAACTACAAGACCACGCCTCCCGTGCTGGAC
961  ---------+---------+---------+---------+---------+---------+ 1020
      E  W  E  S  N  G  Q  P  E  N  N  Y  K  T  T  P  P  V  L  D

TCCGACGGCTCCTTCTTCCTCTACAGCAAGCTCACCGTGGACAAGAGCAGGTGGCAGCAG
1021 ---------+---------+---------+---------+---------+---------+ 1080
      S  D  G  S  F  F  L  Y  S  K  L  T  V  D  K  S  R  W  Q  Q

GGGAACGTCTTCTCATGCTCCGTGATGCATGAGGCTCTGCACAACCACTACACGCAGAAG
1081 ---------+---------+---------+---------+---------+---------+ 1140
      G  N  V  F  S  C  S  V  M  H  E  A  L  H  N  H  Y  T  Q  K

AGCCTCTCGCTCAGCCCGGGTAAATAA          (SEQ ID NO. 5)
1141 ---------+---------+------- 1167
      S  L  S  L  S  P  G  K  *          (SEQ ID NO. 3)
```

Figure 22
sTNF-RI Sequence
2.6D/N105

```
5'-CATATGGACAGCGTTTGCCCCCAAGGAAAATATATCCACCCTCAAAATAATTCGATTTGC-
   +---------+---------+---------+---------+---------+---------+
    M  D  S  V  C  P  Q  G  K  Y  I  H  P  Q  N  N  S  I  C  C -

-TGTACCAAGTGCCACAAAGGAACCTACTTGTACAATGACTGTCCAGGCCCGGGGCAGGAT-
  +---------+---------+---------+---------+---------+---------+
    T  K  C  H  K  G  T  Y  L  Y  N  D  C  P  G  P  G  Q  D  T -

-ACGGACTGCAGGGAGTGTGAGAGCGGCTCCTTCACCGCTTCAGAAAACCACCTCAGACAC-
  +---------+---------+---------+---------+---------+---------+
    D  C  R  E  C  E  S  G  S  F  T  A  S  E  N  H  L  R  H  C -

-TGCCTCAGCTGCTCCAAATGCCGAAAGGAAATGGGTCAGGTGGAGATCTCTTCTTGCACA-
  +---------+---------+---------+---------+---------+---------+
    L  S  C  S  K  C  R  K  E  M  G  Q  V  E  I  S  S  C  T  V -

-GTGGACCGGGACACCGTGTGTGGTTGCAGGAAGAACCAGTACCGGCATTATTGGAGTGAA-
  +---------+---------+---------+---------+---------+---------+
    D  R  D  T  V  C  G  C  R  K  N  Q  Y  R  H  Y  W  S  E  N -

-AACCTTTTCCAGTGCTTCAATTAATAGGGATCC-3'   (SEQ ID NO. 6)
  +---------+---------+---------+---------+---------+---------+
    L  F  Q  C  F  N  *                  (SEQ ID NO. 4)
```

Figure 23
IL-1 RECEPTOR AMINO ACID SEQUENCE

```
  1 mkvllrlicf iallisslea dkckereeki ilvssaneid vrpcplnpne hkgtitwykd
 61 dsktpvsteq asrihqhkek lwfvpakved sghyycvvrn ssyclrikis akfvenepnl
121 cynaqaifkq klpvagdggl vcpymeffkn ennelpklqw ykdckpllld nihfsgvkdr
181 livmnvaekh rgnytchasy tylgkqypit rviefitlee nkptrpvivs panetmevdl
241 gsqiqlicnv tgqlsdiayw kwngsvided dpvlgedyys venpankrrs tlitvlnise
301 iesrfykhpf tcfaknthgi daayiqliyp vtnfqkhmig icvtltviiv csvfiykifk
361 idivlwyrds cydflpikas dgktydayil ypktvgegst sdcdifvfkv lpevlekqcg
421 yklfiygrdd yvgedivevi nenvkksrrl iiilvretsg fswlggssee qiamynalvq
481 dgikvvllel ekiqdyekmp esikfikqkh gairwsgdft qgpqsaktrf wknvryhmpv
541 qrrspsskhq llspatkekl qreahvplg    (SEQ ID NO. 7)
```

Figure 24
TNF RECEPTOR TYPE I AMINO ACID SEQUENCE

```
  1 mglstvpdll lplvllellv giypsgvigl vphlgdrekr dsvcpqgkyi hpqnnsicct
 61 kchkgtylyn dcpgpgqdtd crecesgsft asenhlrhcl scskcrkemg qveissctvd
121 rdtvcgcrkn qyrhywsenl fqcfncslcl ngtvhlscqe kqntvctcha gfflrenecv
181 scsnckksle ctklclpqie nvkgtedsgt tvllplviff glcllsllfi glmyryqrwk
241 sklysivcgk stpekegele gtttkplapn psfsptpgft ptlgfspvps stftssstyt
301 pgdcpnfaap rrevappyqg adpilatala sdpipnplqk wedsahkpqs ldtddpatly
361 avvenvpplr wkefvrrlgl sdheidrlel qngrclreaq ysmlatwrrr tprreatlel
421 lgrvlrdmdl lgcledieea lcgpaalppa psllr    (SEQ ID NO. 8)
```

FIGURE 25
TNF RECEPTOR TYPE II AMINO ACID SEQUENCE

```
  1 mapvavwaal avglelwaaa halpaqvaft pyapepgstc rlreyydqta qmccskcspg
 61 qhakvfctkt sdtvcdsced stytqlwnwv peclscgsrc ssdqvetqac treqnrictc
121 rpgwycalsk qegcrlcapl rkcrpgfgva rpgtetsdvv ckpcapgtfs nttsstdicr
181 phqicnvvai pgnasmdavc tstsptrsma pgavhlpqpv strsqhtqpt pepstapsts
241 fllpmgpspp aegstgdfal pvglivgvta lglliigvvn cvimtqvkkk plclqreakv
301 phlpadkarg tqgpeqqhll itapssssss lessasaldr raptrnqpqa pgveasgage
361 arastgssds spgghgtqvn vtcivnvcss sdhssqcssq asstmgdtds spsespkdeq
421 vpfskeecaf rsqletpetl lgsteekplp lgvpdagmkp s    (SEQ ID NO. 9)
```

FIGURE 26
CD40 AMINO ACID SEQUENCE

```
  1 mvrlplqcvl wgclltavhp epptacrekq ylinsqccsl cqpgqklvsd cteftetecl
 61 pcgesefldt wnrethchqh kycdpnlglr vqqkgtsetd tictceegwh ctseacescv
121 lhrscspgfg vkqiatgvsd ticepcpvgf fsnvssafek chpwtscetk dlvvqqagtn
181 ktdvvcgpqd rlralvvipi ifgilfaill vlvfikkvak kptnkaphpk qepqeinfpd
241 dlpgsntaap vqetlhgcqp vtqedgkesr isvqerq      (SEQ ID NO. 10)
```

FIGURE 27
CD30 AMINO ACID SEQUENCE

```
  1 mrvllaalgl lflgalrafp qdrpfedtch gnpshyydka vrrccyrcpm glfptqqcpq
 61 rptdcrkqce pdyyldeadr ctacvtcsrd dlvektpcaw nssrvcecrp gmfcstsavn
121 scarcffhsv cpagmivkfp gtaqkntvce paspgvspac aspenckeps sgtipqakpt
181 pvspatssas tmpvrggtrl aqeaaskltr apdspssvgr pssdpglspt qpcpegsgdc
241 rkqcepdyyl deagrctacv scsrddlvek tpcawnssrt cecrpgmica tsatnscarc
301 vpypicaaet vtkpqdmaek dttfeapplg tqpdcnptpe ngeapastsp tqsllvdsqa
361 sktlpiptsa pvalsstgkp vldagpvlfw vilvlvvvvg ssafllchrr acrkrirqkl
421 hlcypvqtsq pklelvdsrp rrsstqlrsg asvtepvaee rglmsqplme tchsvgaayl
481 eslplqdasp aggpssprdl peprvsteht nnkiekiyim kadtvivgtv kaelpegrgl
541 agpaepelee eleadhtphy peqetepplg scsdvmlsve eegkedplpt aasgk
```
(SEQ ID NO. 11)

FIGURE 28
ICOS AMINO ACID SEQUENCE

```
  1 mksglwyffl fclrikvltg eingsanyem fifhnggvqi lckypdivqq fkmqllkggq
 61 ilcdltktkg sgntvsiksl kfchsqlsnn svsfflynld hshanyyfcn lsifdpppfk
121 vtltggylhi yesqlccqlk fwlpigcaaf vvvcilgcil icwltkkkys ssvhdpngey
181 mfmravntak ksrltdvtl  (SEQ ID NO. 12)
```

FIGURE 29
CD28 AMINO ACID SEQUENCE

```
  1 mlrlllalnl fpsiqvtgnk ilvkqspmlv aydnavnlsc kysynlfsre fraslhkgld
 61 savevcvvyg nysqqlqvys ktgfncdgkl gnesvtfylq nlyvnqtdiy fckievmypp
121 pyldneksng tiihvkgkhl cpsplfpgps kpfwvlvvvg gvlacysllv tvafiifwvr
181 skrsrllhsd ymnmtprrpg ptrkhyqpya pprdfaayrs   (SEQ ID NO. 13)
```

FIGURE 30
OX40 AMINO ACID SEQUENCE

```
  1 mcvgarrlgr gpcaallllg lglstvtglh cvgdtypsnd rcchecrpgn gmvsrcsrsq
 61 ntvcrpcgpg fyndvvsskp ckpctwcnlr sgserkqlct atqdtvcrcr agtqpldsyk
121 pgvdcapcpp ghfspgdnqa ckpwtnctla gkhtlqpasn ssdaicedrd ppatqpqetq
181 gpparpitvq pteawprtsq gpstrpvevp ggravaailg lglvlgllgp laillalyll
241 rrdqrlppda hkppgggsfr tpiqeeqada hstlaki  (SEQ ID NO. 14)
```

Figure 31
4-1-BB Amino Acid Sequence

```
  1 mgnscyniva tlllvlnfer trslqdpcsn cpagtfcdnn rnqicspcpp nsfssaggqr
 61 tcdicrqckg vfrtrkecss tsnaecdctp gfhclgagcs mceqdckqgq eltkkgckdc
121 cfgtfndqkr gicrpwtncs ldgksvlvng tkerdvvcgp spadlspgas svtppapare
181 pghspqiisf flaltstall fllffltlrf svvkrgrkkl lyifkqpfmr pvqttqeedg
241 cscrfpeeee ggcel   (SEQ ID NO. 15)
```

FIGURE 32
CD27 AMINO ACID SEQUENCE

```
  1 marphpwwlc vlgtlvglsa tpapkscper hywaqgklcc qmcepgtflv kdcdqhrkaa
 61 qcdpcipgvs fspdhhtrph cescrhcnsg llvrnctita naecacrngw qcrdkectec
121 dplpnpslta rssqalsphp qpthlpyvse mleartaghm qtladfrqlp artlsthwpp
181 qrslcssdfi rilvifsgmf lvftlagalf lhqrrkyrsn kgespvepae pcryscpree
241 egstipiqed yrkpepacsp  (SEQ ID NO. 16)
```

FIGURE 33
IL-18 RECEPTOR AMINO ACID SEQUENCE

```
  1 mncrelpltl wvlisvstae sctsrphitv vegepfylkh cscslaheie tttkswykss
 61 gsqehvelnp rsssrialhd cvlefwpvel ndtgsyffqm knytqkwkln virrnkhscf
121 terqvtskiv evkkffqitc ensyyqtlvn stslyknckk lllennknpt ikknaefedq
181 gyyscvhflh hngklfnitk tfnitivedr snivpvllgp klnhvavelg knvrlncsal
241 lneedviywm fgeengsdpn iheekemrim tpegkwhask vlrieniges nlnvlynctv
301 astggtdtks filvrkadma dipghvftrg miiavlilva vvclvtvcvi yrvdlvlfyr
361 hltrrdetlt dgktydafvs ylkecrpeng eehtfaveil prvlekhfgy klciferdvv
421 pggavvdeih slieksrrli ivlsksymsn evryelesgl healverkik iilieftpvt
481 dftflpqslk llkshrvlkw kadkslsyns rfwknllylm paktvkpgrd epevlpvlse
541 s  (SEQ ID NO. 17)
```

FIGURE 34
PD-1 AMINO ACID SEQUENCE

```
  1 mqipqapwpv vwavlqlgwr pgwfldspdr pwnpptfspa llvvtegdna tftcsfsnts
 61 esfvlnwyrm spsnqtdkla afpedrsqpg qdcrfrvtql pngrdfhmsv vrarrndsgt
121 ylcgaislap kaqikeslra elrvterrae vptahpspsp rsagqfqtlv vgvvggllgs
181 lvllvwvlav icsraargti garrtgqplk edpsavpvfs vdygeldfqw rektpeppvp
241 cvpeqteyat ivfpsgmgts sparrgsadg prsaqplrpe dghcswpl(SEQ ID NO. 18)
```

FIGURE 35
RAT TNF RECEPTOR 1 AMINO ACID SEQUENCE

```
  1 mglpivpgll lslvllallm gihpsgvtgl vpslgdrekr dnlcpqgkya hpknnsicct
 61 kchkgtylvs dcpspgqetv cevcdkgtft asqnhvrqcl scktcrkemf qveispckad
121 mdtvcgckkn qfqrylseth fqcvdcspcf ngtvtipcke kqntvncha  gfflsgnect
181 pcshckknqe cmklclppva nvtnpqdsgt avllplvifl glcllffici sllcrypqwr
241 prvysiicrd sapvkevege givtkpltpa sipafspnpg fnptlgfstt prfshpvsst
301 pispvfgpsn whnfvppvre vvptqgadpl lygslnpvpi papvrkwedv vaaqpqrldt
361 adpamlyavv dgvpptrwke fmrllglseh eierlelqng rclreahysm leawrrrtpr
421 heatldvvgr vlcdmnlrgc leniretles pahsstthlp r   (SEQ ID NO. 21)
```

FIGURE 36
MURINE CTLA4 AMINO ACID SEQUENCE

```
  1 maclglrryk aqlqlpsrtw pfvalltllf ipvfseaiqv tqpsvvlass hgvasfpcey
 61 spshntdevr vtvlrqtndq mtevcattft ekntvgfldy pfcsgtfnes rvnltiqglr
121 avdtglylck velmypppyf vgmgngtqiy vidpepcpds dfllwilvav slglffysfl
181 vsavslskml kkrsplttgv yvkmpptepe cekqfqpyfi pin   (SEQ ID NO. 19)
```

FIGURE 37
TACI AMINO ACID SEQUENCE

```
  1 msglgrsrrg grsrvdqeer fpqglwtgva mrscpeeqyw dpllgtcmsc kticnhqsqr
 61 tcaafcrsls crkeqgkfyd hllrdcisca sicgqhpkqc ayfcenklrs pvnlppelrr
121 qrsgevenns dnsgryqgle hrgseaspal pglklsadqv alvystlglc lcavlccflv
181 avacflkkrg dpcscqprsr prqspakssq dhameagspv stspepvetc sfcfpecrap
241 tqesavtpgt pdptcagrwg chtrttvlqp cphipdsglg ivcvpaqegg pga
    (SEQ ID NO. 27)
```

COMBINATION THERAPY WITH CO-STIMULATORY FACTORS

PRIORITY INFORMATION

This application is a continuation of U.S. patent application Ser. No. 10/748,112, filed Dec. 29, 2003 now abandoned, which claims priority benefit of U.S. Patent Application No. 60/437,405, filed Dec. 30, 2002. The entire contents of U.S. patent application Ser. Nos. 10/748,112 and 60/437,405 is are incorporated herein by reference in its their entirety.

FIELD OF THE INVENTION

The present invention relates to polypeptides involved in the regulation of inflammation and immune response. The invention also relates to combination therapy using molecules involved in B-cell and T-cell stimulation with cytokine antagonists.

BACKGROUND OF THE INVENTION

Inflammatory autoimmune diseases typically involve a complex dysregulation of the biological system. In ongoing autoimmune diseases, in certain instances, certain proinflammatory cytokines such as TNF and IL-1 are elevated. In addition, in certain instances, immune T cells and B cells may also play a role by producing cytokines, chemokines and autoantibodies.

Activation of the immune system to the body's self molecules leads to autoimmunity. Certain inflammatory autoimmune diseases are the outcome of interactions that occur between antigen presenting cells (APC) and T cells, and between T and B cells. Certain inflammatory autoimmune disease are also the result of activation of B cells—in addition to the proinflammatory cytokine cascade. During an immune response, antigenic peptides are presented by major histocompatibility complex (MHC) molecules expressed on antigen presenting cells (APCs) to the T cell receptor expressed on T cells.

This recognition event may not fully activate T cells. In certain instances, a CD4 interaction to the MHC molecule and 'a second or co-stimulatory' signal (during cognate interaction of APC and T cell) may be required for T cell proliferation, cytokine production and intracellular signaling events. Interaction of CD28 and B7 molecules was identified as a second signal to activate T cells. This pathway of immune co-stimulation has a negative regulator, CTLA4, expressed on activated T cells. Treatment with a soluble receptor recombinant protein of CTLA-4 leads to inactivation of immune T and B cells.

In recent years, many other co-stimulatory molecules expressed on APC or T cells (CD40:CD40L, B7:CD28 and CTLA-4,4-IBB:4-1BBL, OX40L:OX40, B7RP1:ICOS etc.) have been shown to be involved in the activation of T cells. Some of these co-stimulatory molecules are also involved in B cell activation and antibody production.

SUMMARY OF THE INVENTION

In certain embodiments, a method for treating an IL-1 mediated disease is provided, comprising administering a therapeutically effective amount of an IL-1 inhibitor and at least one of a B7 inhibitor and a CD28 inhibitor.

In certain embodiments, a method for treating a TNF-α mediated disease is provided, comprising administering a therapeutically effective amount of a TNF-α inhibitor and at least one of a B7 inhibitor and a CD28 inhibitor.

In certain embodiments, a method for treating an inflammatory or an autoimmune condition is provided, comprising administering a therapeutically effective amount of an IL-1 inhibitor and at least one of a B7 inhibitor and a CD28 inhibitor.

In certain embodiments, a method for treating an inflammatory or an autoimmune condition is provided, comprising administering a therapeutically effective amount of a TNF-α inhibitor and at least one of a B7 inhibitor and a CD28 inhibitor.

In certain embodiments, a method for treating an inflammatory or an autoimmune condition is provided, comprising administering a therapeutically effective amount of (i) at least one of an AGP3 inhibitor, a BAFFR inhibitor, and a TACI inhibitor, and (ii) at least one of a B7 inhibitor and a CD28 inhibitor.

In certain embodiments, a method for treating an inflammatory or an autoimmune condition is provided, comprising administering a therapeutically effective amount of an IL-1 inhibitor, a therapeutically effective amount of a TNF-α inhibitor, and at least one of a B7 inhibitor and a CD28 inhibitor.

BRIEF DESCRIPTION OF THE FIGURES

FIGS. 3A and 3B show levels of type II collagen (CII) specific antibodies present in serum samples taken ten days after the conclusion of the experiment shown in FIG. 2. (A) Levels of IgG1 antibodies; (B) Levels of IgG2b antibodies. Antibodies were assayed as described in Example 2.

FIG. 19 shows the AGP-3 Peptibody amino acid sequence (SEQ ID NO. 1).

FIG. 20 shows human CTLA4 amino acid sequence (SEQ ID NO. 2).

FIG. 21 shows the KIN2 (FcIL-1ra) nucleotide (SEQ ID NO. 5) and corresponding amino acid sequence (SEQ ID NO. 3).

FIG. 22 shows sTNFR-I nucleotide (SEQ ID NO. 6) and corresponding amino acid sequence (SEQ ID NO. 4).

FIG. 23 shows the IL-1 Receptor amino acid sequence (SEQ ID NO. 7).

FIG. 24 shows the TNFR-I amino acid sequence (SEQ ID NO. 8).

FIG. 25 shows the TNFR-II amino acid sequence (SEQ ID NO. 9).

FIG. 26 shows the CD40 amino acid sequence (SEQ ID NO. 10).

FIG. 27 shows the CD30 amino acid sequence (SEQ ID NO. 11).

FIG. 28 shows the ICOS amino acid sequence (SEQ ID NO. 12).

FIG. 29 shows the CD28 amino acid sequence (SEQ ID NO. 13).

FIG. 30 shows the OX40 amino acid sequence (SEQ ID NO. 14).

FIG. 31 shows the 4-1-BB amino acid sequence (SEQ ID NO. 15).

FIG. 32 shows the CD27 amino acid sequence (SEQ ID NO. 16).

FIG. 33 shows the IL-18 Receptor amino acid sequence (SEQ ID NO. 17).

FIG. 34 shows the PD-1 amino acid sequence (SEQ ID NO. 18).

FIG. 35 shows the rat TNFR-I amino acid sequence (SEQ ID NO. 21).

FIG. 36 shows the murine CTLA4 amino acid sequence (SEQ ID NO. 19).

FIG. 37 shows the TACI amino acid sequence (SEQ ID NO. 27)

DETAILED DESCRIPTION OF CERTAIN PREFERRED EMBODIMENTS

Figure 1:
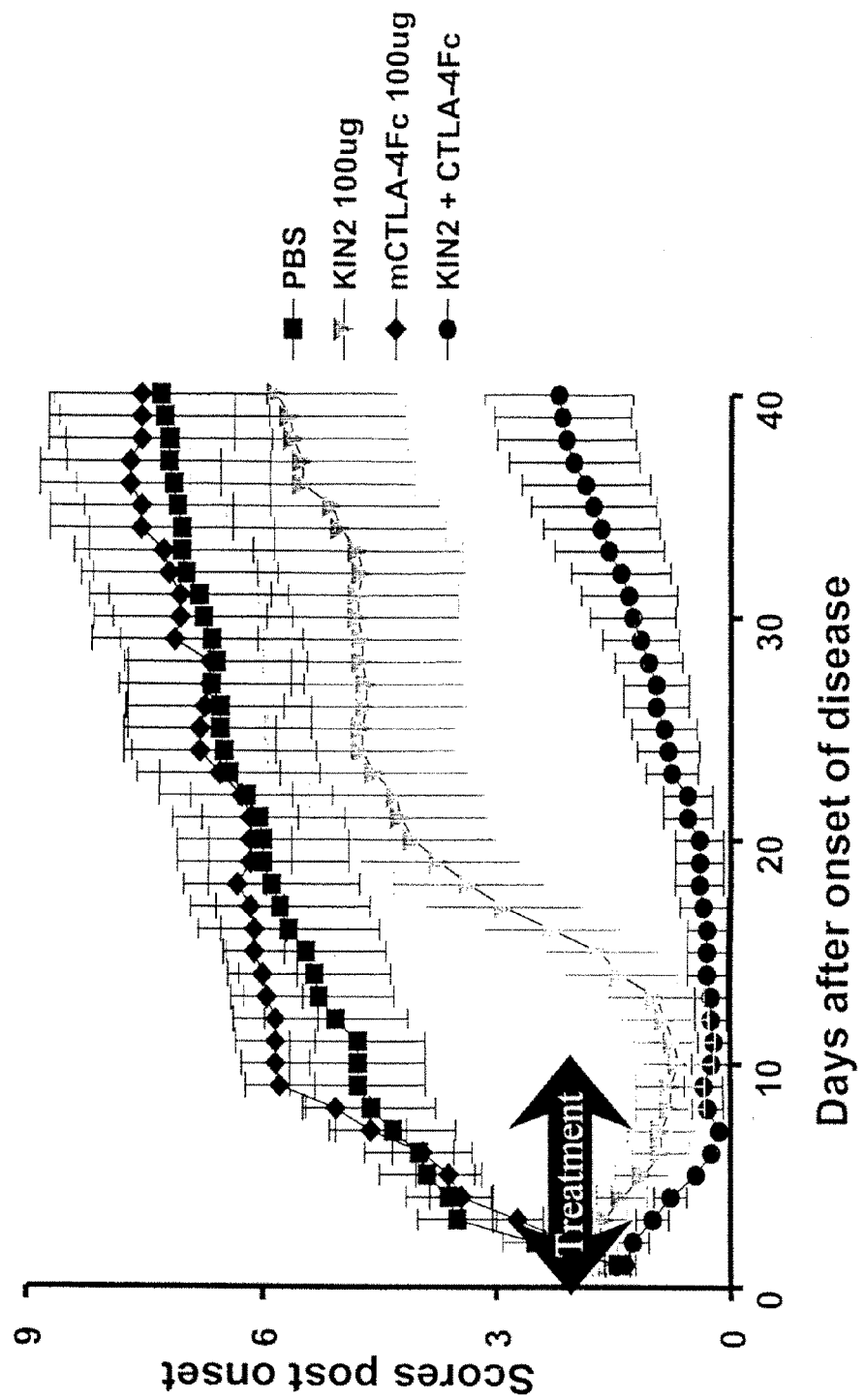
FIG. 1 shows mean arthritis scores in collagen-induced arthritis (CIA) animals during and after treatment with an IL-1 inhibitor (KIN2) (SEQ ID NO. 3), murine CTLA4-Fc fusion protein, and a combination thereof. The arrow indicates that animals were administered by injection 100 µg of KIN2, 100 µg murine CTLA4-Fc, or 100 µg each of KIN2 and murine CTLA4-Fc at day 0, +1, +2, +4, +6, +8 and +10 post onset of disease. 100 µg is equivalent to 5 mg of therapeutic per Kg weight of animal (5 mg/Kg). Phosphate buffered saline (PBS) was used as a control. Error bars indicate standard error from the mean.

The section headings used herein are for organizational purposes only and are not to be construed as limiting the subject matter described. All references or portions of references cited in this application are expressly incorporated by reference herein for any purpose.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is linked to a polynucleotide which it is not linked to in nature, or (3) does not occur in nature as part of a larger sequence.

The term "isolated protein" referred to herein means a protein encoded by cDNA, recombinant RNA, or synthetic origin or some combination thereof, which (1) is free of at least some proteins with which it would normally be found, (2) is essentially free of other proteins from the same source, e.g., from the same species, (3) is expressed by a cell from a different species, or (4) does not occur in nature.

The term "polypeptide" is used herein as a generic term to refer to native proteins, or sequences that have deletions, additions, and/or substitutions of one or more amino acids of the native sequence.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to components that are in a relationship permitting them to function in their intended manner. For example, a control sequence "operably linked" to a coding sequence is ligated in such a way that expression of the coding sequence is achieved under conditions compatible with the control sequences.

The term "control sequence" as used herein refers to polynucleotide sequences which may effect the expression and processing of coding sequences to which they are ligated. The nature of such control sequences may differ depending upon the host organism. According to certain embodiments, control sequences for prokaryotes may include promoter, ribosomal binding site, and transcription termination sequence. According to certain embodiments, control sequences for eukaryotes may include promoters and transcription termination sequence. In certain embodiments, "control sequences" can include leader sequences and/or fusion partner sequences.

The term "soluble receptor molecule" refers to a molecule comprising a fragment of a receptor that remains capable of binding to one or more ligands associated with the receptor. In certain embodiments, a fragment may comprise the entire extracellular domain of a receptor or a subfragment thereof. In certain embodiments, the soluble receptor molecules may be linked to other groups.

In certain embodiments, the fragment may be linked to additional amino acids from the receptor, as in splice variants. In certain embodiments, splice variants may comprise amino acids from the intracellular domain or transmembrane domain, or even from another natural protein.

In certain embodiments, the fragment may be linked to another protein or protein fragment sequence, forming a fusion protein. In certain embodiments, the fusion partner protein or fragment may provide greater half-life to the molecule (e.g., an Fc domain, albumin, or a leucine zipper domain). In certain embodiments, the fusion partner protein or fragment may also provide a different functionality (e.g., capable of binding to the same or a different ligand), forming a bifunctional molecule. In certain embodiments, this functional fusion partner may be another fragment of the same receptor, thus forming a ligand binding dimer.

In certain embodiments, the fragment may be linked to an N-terminal methionine, which may be useful to allow expression in prokaryotic cells such as E. coli.

In certain embodiments, the fragment may be linked to non-proteinaceous groups. Such groups include, but are not limited to, N-linked or O-linked carbohydrate chains, water-soluble polymers such as polyethylene glycol (PEG) and derivatives thereof (see for example U.S. Pat. No. 4,179,337). Other chemical modifications within the meaning of this term include, but are not limited to, ethylene glycol/propylene glycol copolymers, carboxymethylcellulose, dextran, polyvinyl alcohol and related molecules. In certain embodiments, the polypeptides may be modified at random positions within the molecule, or at predetermined positions within the molecule and may include one, two, three or more attached chemical moieties. In certain embodiments, polypeptides may also be modified at pre-determined positions in the polypeptide, such as at the amino terminus, or at a selected lysine or arginine residue within the polypeptide. Other chemical modifications include, but are not limited to, a detectable label, such as an enzymatic, fluorescent, isotopic or affinity label to allow for detection and isolation of the protein.

The term "protein" refers to polypeptides regardless of length or origin, comprising molecules that are recombinantly produced or naturally occurring, full length or truncated, having a natural sequence or mutated sequence, with or without post-translational modification, whether produced in mammalian cells, bacterial cells, or any other expression system.

The term "specific binding partner" refers to any molecule that preferentially binds to a protein of interest, regardless of the antagonistic or agonistic activity of the molecule toward the protein of interest. Exemplary, specific binding partners include, but are not limited to, antibodies, solubilized receptors, peptides, modified peptides, and related molecules.

The term "vehicle" refers to a molecule that prevents degradation and/or increases half-life, reduces toxicity, reduces immunogenicity, or increases biological activity of a therapeutic protein. In certain embodiments, vehicles include an Fc domain, as well as a linear polymer (e.g., polyethylene glycol (PEG), polylysine, dextran, etc.); a branched-chain polymer (see, for example, U.S. Pat. Nos. 4,289,872 to Denkenwalter et al., issued Sep. 15, 1981; 5,229,490 to Tam, issued Jul. 20, 1993; WO 93/21259 by Frechet et al., published 28 Oct. 1993); a lipid; a cholesterol group (such as a steroid); a carbohydrate or oligosaccharide; and any natural or synthetic protein, polypeptide or peptide that binds to a salvage receptor.

The term "native Fc" refers to a molecule or sequence comprising the sequence of a non-antigen-binding fragment resulting from digestion of whole antibody, whether in monomeric or multimeric form. In certain embodiments, the original immunoglobulin source of the native Fc is of human origin and may be any of the immunoglobulins, including, but not limited to, IgG1 and IgG2. Native Fc's typically are made up of monomeric polypeptides that may be linked into dimeric or multimeric forms by covalent (i.e., disulfide bonds) and non-covalent association. In certain embodiments, the number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). In certain embodiments, a native Fc is a disulfide-bonded dimer resulting from papain digestion of an IgG (see, e.g., Ellison et al. (1982), *Nucleic Acids Res.* 10: 4071-9). The term "native Fc" as used herein is generic to the monomeric, dimeric, and multimeric forms.

The term "Fc variant" refers to a molecule or sequence that is modified from a native Fc but still comprises a binding site for the salvage receptor, FcRn. International applications WO 97/34631 (published 25 Sep. 1997) and WO 96/32478 describe exemplary Fc variants, as well as interaction with the salvage receptor, and are hereby incorporated by reference in their entirety for any purpose. In certain embodiments, the term "Fc variant" comprises a molecule or sequence that is humanized from a non-human native Fc. In certain embodiments, a native Fc comprises sites that may be removed because they provide structural features or biological activity that are not required for the fusion molecules of the present invention. In certain embodiments, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Certain Fc variants are described in further detail in WO 00/24782, published May 4, 2000, which is hereby incorporated by reference in its entirety for any purpose.

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by other means.

The term "multimer" as applied to Fc domains or molecules comprising Fc domains refers to molecules having two or more polypeptide chains associated covalently, noncovalently, or by both covalent and non-covalent interactions. IgG molecules typically form dimers; IgM, pentamers; IgD, dimers; and IgA, monomers, dimers, trimers, or tetramers. In certain embodiments, multimers may be formed by exploiting the sequence and resulting activity of the native Ig source of the Fc or by derivatizing (as defined below) such a native Fc.

The term "dimer" as applied to Fc domains or molecules comprising Fc domains refers to molecules having two polypeptide chains associated covalently or non-covalently.

The terms "derivatizing" and "derivative" or "derivatized" comprise processes and resulting compounds respectively in which at least one of the following is present: (1) the compound has a cyclic portion; for example, cross-linking between cysteinyl residues within the compound; (2) the compound is cross-linked or has a cross-linking site; for example, the compound has a cysteinyl residue and thus forms cross-linked dimers in culture or in vivo; (3) one or more peptidyl linkage is replaced by a non-peptidyl linkage; (4) the N-terminus is replaced by $—NRR^1$, $NRC(O)R^1$, $—NRC(O)OR^1$, $—NRS(O)_2R^1$, $—NHC(O)NHR$, a succinimide group, or substituted or unsubstituted benzyloxycarbonyl-NH—, wherein R and $R^1$ and the ring substituents are as defined hereinafter; (5) the C-terminus is replaced by $—C(O)R^2$ or $—NR^3R^4$ wherein $R^2$, $R^3$ and $R^4$ are as defined hereinafter; and (6) a compound in which individual amino acid moieties are modified through treatment with agents capable of reacting with selected side chains or terminal residues.

The term "peptide" refers to molecules of 2 to 40 amino acids, including, but not limited to, molecules of 3 to 20 amino acids and molecules of 6 to 15 amino acids. In certain embodiments, peptides may be randomly generated by any of the methods cited herein, carried in a peptide library (e.g., a phage display library), or derived by digestion of proteins.

The term "randomized", as used to refer to peptide sequences, refers to fully random sequences (e.g., selected by phage display methods) and sequences in which one or more residues of a naturally occurring molecule is replaced by an amino acid residue not appearing in that position in the naturally occurring molecule. Exemplary methods for identifying peptide sequences include, but are not limited to, phage display, *E. coli* display, ribosome display, yeast-based screening, RNA-peptide screening, chemical screening, rational design, protein structural analysis, and the like. Certain randomized peptides and certain methods of generating them appear in, e.g., WO 00/24782, published May 4, 2000, which is hereby incorporated by reference in its entirety for any purpose.

The term "pharmacologically active" means that a substance so described is determined to have activity that affects a medical parameter (e.g., T cell proliferation) or disease state (e.g., cancer, autoimmune disorders). In certain embodiments, pharmacologically active compounds comprise agonistic or mimetic and antagonistic compounds as defined below.

The term "pharmaceutical agent or drug" as used herein refers to a chemical compound or composition capable of inducing a desired therapeutic effect when properly administered to a patient.

The term "biological sample", as used herein, includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph nodes, and skin.

As used herein, "substantially pure" means an object species is the predominant species present (i.e., on a molar basis it is more abundant than any other individual species in the composition). In certain embodiments, a substantially purified fraction is a composition wherein the object species comprises at least about 50 percent (on a molar basis) of all macromolecular species present. In certain embodiments, a substantially pure composition will comprise more than about 80%, 85%, 90%, 95%, or 99% of all macromolar species present in the composition. In certain embodiments, the object species is purified to essential homogeneity (contaminant species cannot be detected in the composition by conventional detection methods) wherein the composition consists essentially of a single macromolecular species.

The term "patient" includes human and animal subjects.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotin moieties that can be detected by marked avidin (e.g., streptavidin containing a fluorescent marker or enzymatic activity that can be detected by optical or colorimetric methods). In certain embodiments, the label or marker can also be therapeutic. Various methods of labeling polypeptides and glycoproteins are known in the art and may be used. Examples of labels for polypeptides include, but are not limited to, the following: radioisotopes or radionuclides (e.g., 3 H, 14 C, 15 N, 35 S, 90 Y, 99 Tc, 111 In, 125 I, 131 I), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce potential steric hindrance.

The terms "antagonist" or "inhibitor" refer to a molecule that blocks or in some way interferes with the biological activity of the associated protein of interest, or has biological activity comparable to a known antagonist or inhibitor of the associated protein of interest.

Additionally, physiologically acceptable salts of the compounds of this invention are also encompassed herein. By "physiologically acceptable salts" is meant any salts that are known or later discovered to be pharmaceutically acceptable. Certain examples include, but are not limited to, acetate; trifluoroacetate; hydrohalides, such as hydrochloride and hydrobromide; sulfate; citrate; tartrate; glycolate; and oxalate.

The term "polynucleotide" as referred to herein means a polymeric form of nucleotides of at least 10 bases in length. In certain embodiments, the bases may be ribonucleotides or deoxyribonucleotides or a modified form of either type of nucleotide. The term includes single and double stranded forms of DNA.

The term "oligonucleotide" as referred to herein includes naturally occurring, and modified nucleotides linked together by naturally occurring, and/or non-naturally occurring oligonucleotide linkages. Oligonucleotides are a polynucleotide subset generally comprising a length of 200 bases or fewer. In certain embodiments, oligonucleotides are 10 to 60 bases in length. In certain embodiments, oligonucleotides are 12, 13, 14, 15, 16, 17, 18, 19, or 20 to 40 bases in length. Oligonucleotides may be single stranded or double stranded, e.g. for use in the construction of a gene mutant. Oligonucleotides of the invention may be sense or antisense oligonucleotides.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotides linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. Anti-Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990), the disclosures of which are hereby incorporated by reference for any purpose. An oligonucleotide can include a label for detection.

Identity and similarity of related and polypeptides can be readily calculated by known methods. Such methods include, but are not limited to, those described in Computational Molecular Biology, Lesk, A. M., ed., Oxford University Press, New York (1988); Biocomputing: Informatics and Genome Projects, Smith, D. W., ed., Academic Press, New York (1993); Computer Analysis of Sequence Data, Part 1, Griffin, A. M., and Griffin, H. G., eds., Humana Press, New Jersey (1994); Sequence Analysis in Molecular Biology, von Heinje, G., Academic Press (1987); Sequence Analysis Primer, Gribskov, M. and Devereux, J., eds., M. Stockton Press, New York (1991); and Carillo et al., *SIAM J. Applied Math.*, 48:1073 (1988).

Certain preferred methods to determine identity are designed to give the largest match between the sequences tested. Methods to determine identity are described in publicly available computer programs. Certain computer program methods to determine identity between two sequences include, but are not limited to, the GCG program package, including GAP (Devereux et al., *Nucl. Acid. Res.*, 12:387 (1984); Genetics Computer Group, University of Wisconsin, Madison, Wis., BLASTP, BLASTN, and FASTA (Altschul et al., *J. Mol. Blot,* 215:403-410 (1990)). The BLASTX program is publicly available from the National Center for Biotechnology Information (NCBI) and other sources (*BLAST Manual*, Altschul et al. NCB/NLM/NIH Bethesda, Md. 20894; Altschul et al., supra (1990)). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in certain embodiments, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see Dayhoff et al., *Atlas of Protein Sequence and Structure*, 5(3)(1978) for the PAM 250 comparison matrix; Henikoff et al., *Proc. Natl. Acad. Sci. USA*, 89:10915-10919 (1992) for the BLOSUM 62 comparison matrix) is also used by the algorithm.

In certain embodiments, the parameters for a polypeptide sequence comparison include the following:

Algorithm: Needleman et al., *J. Mol. Biol.*, 48:443-453 (1970);

Comparison matrix: BLOSUM 62 from Henikoff et al., supra (1992);

Gap Penalty: 12

Gap Length Penalty: 4

Threshold of Similarity: 0

The GAP program may be useful with the above parameters. In certain embodiments, the aforementioned parameters are the default parameters for polypeptide comparisons (along with no penalty for end gaps) using the GAP algorithm.

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference for any purpose. Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "modulator," as used herein, is a compound that changes or alters the activity or function of a molecule. For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Certain exemplary activities and functions of a molecule include, but are not limited to, binding affinity, enzymatic activity, and signal transduction. Certain exemplary inhibitors include, but are not limited to, proteins, peptides, antibodies, peptibodies, carbohydrates or small organic molecules. Peptibodies are described, e.g., in WO01/83525.

Any number of molecules may serve as specific binding partners within the present invention. Exemplary molecules include, but are not limited to, antibodies, peptides, and Fc-peptide fusion molecules.

"Antibody" or "antibody peptide(s)" refer to an intact antibody, or a binding fragment thereof that competes with the intact antibody for specific binding. In certain embodiments, binding fragments are produced by recombinant DNA techniques. In certain embodiments, binding fragments are produced by enzymatic or chemical cleavage of intact antibodies. Binding fragments include, but are not limited to, Fab, Fab', F(ab')2, Fv, and single-chain antibodies.

In certain embodiments, the invention provides for an antibody or antigen binding domain thereof, or a fragment, variant, or derivative thereof, which binds to an epitope on any of the target molecules and has partial or complete antagonist activity. In certain embodiments, the target molecule is mammalian, such as human, and may be in soluble or cell surface associated forms, or fragments, derivatives and variants thereof.

A number of methods for antibody generation are known in the art. Such methods are useful in generating molecules useful in accordance with certain embodiments of the present invention. In certain embodiments, an antibody may be prepared by immunizing an animal with the target molecule (e.g., murine or human BCMA or TACI) or with an immunogenic fragment, derivative or variant thereof. In certain embodiments, an animal may be immunized with cells transfected with a vector containing a nucleic acid molecule encoding the target molecule such that the target molecule is expressed and associated with the surface of the transfected cells. In certain embodiments, specific binding partners that are antibodies may be obtained by screening a library comprising antibody or antigen binding domain sequences for binding to the target molecule. In certain embodiments, a library may be prepared in bacteriophage as protein or peptide fusions to a bacteriophage coat protein which are expressed on the surface of assembled phage particles and the encoding DNA sequences contained within the phage particles (so-called "phage display library"). In certain embodiments, a phage display library contains DNA sequences encoding human antibodies, such as variable light and heavy chains. In certain embodiments, sequences binding to the target molecule may be further evolved by multiple rounds of mutagenesis and screening.

In certain embodiments, specific binding partners that are antibodies or antigen binding domains may be tetrameric glycoproteins similar to native antibodies, or they may be single chain antibodies; for example, Fv, Fab, Fab' or F(ab)° fragments, bispecific antibodies, heteroantibodies, or other fragments, variants, or derivatives thereof, which are capable of binding the target molecule and partially or completely neutralizing the target molecule activity. In certain embodiments, antibodies or antigen binding domains may be produced in hybridoma cell lines (antibody-producing cells such as spleen cells fused to mouse myeloma cells, for example) or may be produced in heterologous cell lines transfected with nucleic acid molecules encoding said antibody or antigen binding domain.

Exemplary antibodies include, but are not limited to, polyclonal monospecific polyclonal, monoclonal, recombinant, chimeric, humanized, fully human, single chain and/or bispecific antibodies. In certain embodiments, antibody fragments include those portions of an antibody that bind to an epitope on a target molecule. Examples of such fragments include, but are not limited to, Fab F(ab'), F(ab)', Fv, and sFv fragments. In certain embodiments, antibodies may be generated by enzymatic cleavage of full-length antibodies or by recombinant DNA techniques, such as expression of recombinant plasmids containing nucleic acid sequences encoding antibody variable regions.

Polyclonal antibodies are heterogeneous populations of antibody molecules derived from the sera of animals immunized with an antigen. In certain embodiments, an antigen is a molecule or a portion of a molecule capable of being bound by an antibody which is additionally capable of inducing an animal to produce antibody capable of binding to an epitope of that antigen. An antigen can have one or more epitope. A specific reaction involving an antigen means that an antigen will react, in a selective manner, with its corresponding antibody and not with a multitude of other antibodies which can be evoked by other antigens.

In certain embodiments, polyclonal antibodies directed toward a target molecule generally are raised in animals (e.g., rabbits or mice) by multiple subcutaneous or intraperitoneal injections of the target molecule and an adjuvant. In certain embodiments, the target molecule, or a variant, fragment, or derivative thereof is conjugated to a carrier protein that is immunogenic in the species to be immunized, such as, in certain embodiments, keyhole limpet heocyanin, serum, albumin, bovine thyroglobulin, or soybean trypsin inhibitor. In certain embodiments, aggregating agents such as alum may be used to enhance the immune response. In certain embodiments, after immunization, the animals may be bled and the serum assayed for anti-target antibody titer.

Monoclonal antibodies (mAbs) contain a substantially homogeneous population of antibodies containing substantially similar epitope binding sites. Such antibodies may be of any immunoglobulin class, including, but not limited to, IgG, IgM, IgE, IgA, IgD and any subclass thereof. In certain embodiments, a hybridoma producing a monoclonal antibody of the present invention may be cultivated in vitro, in situ, or in vivo. In certain embodiments, one produces high titers in vivo or in situ.

Monoclonal antibodies directed toward the target molecule are typically produced using any method which provides for the production of antibody molecules by continuous cell lines in culture. Exemplary methods for preparing monoclonal antibodies include, but are not limited to, the hybridoma methods of Kohler et al., *Nature* 256, 495-497 (1975), and the human B-cell hybridoma method, Kozbor, *J. Immunol.* 133, 3001 (1984); Brodeur et al., Monoclonal Antibody Production Techniques and Applications, pp. 51-63 (Marcel Dekker, Inc., New York, 1987); and Harlow and Lane, Antibodies: A Laboratory Manual, Cold Spring Harbor Laboratory (1988); the contents of which are incorporated herein by reference in their entirety for any purpose.

In certain embodiments, specific binding partners include monoclonal antibodies which will inhibit partially or completely the binding of the human target molecule to its cognate ligand or receptor or an antibody having substantially the same specific binding characteristics, as well as fragments and regions thereof. Certain methods for determining monoclonal antibody specificity and affinity by competitive inhibition can be found, e.g., in Harlow et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), and Muller, *Meth. Enzymol.*, 92:589-601 (1983). Each of these references is incorporated herein by reference in its entirety for any purpose.

In certain embodiments, hybridoma cell lines produce monoclonal antibodies reactive with target polypeptides.

Chimeric antibodies are molecules in which different portions are derived from different animal species, such as those having a variable region derived from a murine monoclonal antibody and a human immunoglobulin constant region. In certain embodiments, chimeric antibodies may be used to reduce immunogenicity in application and to increase yields in production. In certain embodiments, murine monoclonal antibodies have higher yields from hybridomas but higher immunogenicity in humans, such that human/murine chimeric monoclonal antibodies may be used.

Certain chimeric antibodies and certain methods for their production are known in the art. See, e.g., Cabilly et al., *Proc. Natl. Acad. Sci. USA*, 81:3273-3277 (1984); Morrison et al., *Proc. Natl. Acad. Sci. USA*, 81:6851-6855 (1984); Boulianne et al., *Nature*, 312:643-646 (1984); Neuberger et al., *Nature*, 314:268-270 (1985); Liu et al., *Proc. Natl. Acad. Sci. USA*, 84:3439-3443 (1987); and Harlow and Lane Antibodies: A Laboratory Manual, Cold Spring Harbor Laboratory (1988). These references are incorporated herein by reference in their entirety for any purpose.

In certain embodiments, a chimeric monoclonal antibody may be used as a therapeutic agent. In certain embodiments, a portion of the heavy and/or light chain may be identical with or homologous to corresponding sequences in antibodies derived from a particular species or belonging to one particular antibody class or subclass, while the remainder of the chain(s) is identical with or homologous to corresponding sequence in antibodies derived from another species or belonging to another antibody class or subclass, as well as fragments of such antibodies, so long as they exhibit the desired biological activity (see, e.g., U.S. Pat. No. 4,816,567; Morrison et al., *Proc. Natl. Acad. Sci.*, 81, 6851-6855 (1985).

As used herein, the term "chimeric antibody" includes monovalent, divalent or polyvalent immunoglobulins. A monovalent chimeric antibody is a dimer (HL) formed by a chimeric H chain associated through disulfide bridges with a chimeric L chain. A divalent chimeric antibody is a tetramer ($H_2L_2$) formed by two HL dimers associated through at least one disulfide bridge. In certain embodiments, a polyvalent chimeric antibody may be produced, for example, by employing a $C_H$ region that aggregates (e.g., from an IgM H chain, or μ chain).

In certain embodiments, murine and chimeric antibodies, fragments and regions may comprise individual heavy (H) and/or light (L) immunoglobulin chains. In certain embodiments, a chimeric H chain comprises an antigen binding region derived from the H chain of a non-human antibody specific for the target molecule, which is linked to at least a portion of a human H chain C region ($C_H$), such as $CH_1$ or $CH_2$.

In certain embodiments, a chimeric L chain comprises an antigen binding region derived from the L chain of a non-human antibody specific for the target molecule, linked to at least a portion of a human L chain C region ($C_L$).

In certain embodiments, specific binding partners, such as antibodies, fragments, or derivatives, having chimeric H chains and L chains of the same or different variable region binding specificity, can also be prepared by appropriate association of the individual polypeptide chains, according to known method steps, e.g., according to Ausubel et al., eds. *Current Protocols in Molecular Biology*, Wiley Interscience, N.Y. (1993), and Harlow et al., Antibodies: A Laboratory Manual, Cold Spring Harbor Laboratory Press, Cold Spring Harbor, N.Y. (1988). The contents of these references are incorporated herein by reference in their entirety for any purpose. In certain embodiments, hosts expressing chimeric H chains (or their derivatives) are separately cultured from hosts expressing chimeric L chains (or their derivatives), and the immunoglobulin chains are separately recovered and then associated. In certain embodiments, the hosts can be co-cultured and the chains allowed to associate spontaneously in the culture medium, followed by recovery of the assembled immunoglobulin, fragment or derivative.

In certain embodiments, the antigen binding region of the specific binding partner (such as a chimeric antibody) of the present invention may be derived from a non-human antibody specific for the human analog of the target molecule. In certain embodiments, the sources for the DNA encoding a non-human antibody include cell lines which produce antibodies, such as hybrid cell lines commonly known as hybridomas.

In certain embodiments, the invention also provides for fragments, variants and derivatives, and fusions of anti-target antibodies, wherein the terms "fragments", "variants", "derivatives" and "fusions" are defined herein. In certain embodiments, the invention encompasses fragments, variants, derivatives, and fusions of anti-target antibodies which are functionally similar to the unmodified antibody, that is, they retain at least one of the activities of the unmodified antibody. In certain embodiments, modifications include the addition of genetic sequences coding for cytotoxic proteins such as plant and bacterial toxins. In certain embodiments, the fragments, variants, derivatives and fusions of the antibodies can be produced from any host.

The term "fragment" refers to a peptide or polypeptide that comprises less than the full length amino acid sequence of a protein. Such a fragment may arise, for example, from a truncation at the amino terminus, a truncation at the carboxy terminus, and/or an internal deletion of a residue(s) from the amino acid sequence. Fragments may result from alternative RNA splicing or from in vivo protease activity.

The term "variant" refers to a peptide or polypeptide comprising one or more amino acid sequence substitutions, deletions, and/or additions as compared to a native or unmodified sequence. Variants may be naturally occurring, such as allelic or splice variants, or may be artificially constructed. Polypeptide variants may be prepared from the corresponding nucleic acid molecules encoding said variants.

The term "derivative" refers to a polypeptide or peptide, or a variant or fragment thereof, which has been chemically modified. Examples include, but are not limited to, covalent attachment of one or more polymers, such as water soluble polymers, N-linked, or O-linked carbohydrates, sugars, phosphates, and/or other such molecules. In certain embodiments, derivatives are modified in a manner that is different from naturally occurring or starting peptide or polypeptides, either in the type or location of the molecules attached. Exemplary derivatives include, but are not limited to, deletion of one or more chemical groups which are naturally present on the peptide or polypeptide.

The term "fusion" refers to the joining of a peptide or polypeptide, or fragment, variant and/or derivative thereof, with a heterologous peptide or polypeptide.

Suitable fragments include, but are not limited to, for example, Fab, Fab', F(ab')$_2$, Fv and scFv. These fragments lack the Fc fragment of an intact antibody, clear more rapidly from the circulation, and can have less non-specific tissue binding than an intact antibody. See Wahl et al., *J. Nucl. Med.*, 24:316-325 (1983). In certain embodiments, fragments are produced from intact antibodies using methods well known in the art. In certain embodiments, fragments are produced from intact antibodies by proteolytic cleavage with enzymes such as papain (to produce Fab fragments) or pepsin (to produce F(ab')$_2$ fragments). The identification of these antigen binding regions and/or epitopes recognized by monoclonal antibodies of the present invention in certain instances provides information necessary to generate additional monoclonal antibodies with similar binding characteristics and therapeutic or diagnostic utility that parallel certain embodiments of this invention.

In certain embodiments, variants of specific binding partners are also provided. In certain embodiments, variants of antibodies and antigen binding domains comprise changes in light and/or heavy chain amino acid sequences that are naturally occurring or are introduced by in vitro engineering of native sequences using recombinant DNA techniques. In certain embodiments, naturally occurring variants include "somatic" variants which are generated in vivo in the corresponding germ line nucleotide sequences during the generation of an antibody response to a foreign antigen.

In certain embodiments, variants of antibodies and antigen binding domains may be prepared by mutagenesis techniques known in the art. In certain embodiments, amino acid changes may be introduced at random throughout an antibody coding region and the resulting variants may be screened for a desired activity, such as binding affinity for the target molecule. In certain embodiments, amino acid changes may be introduced in selected regions of an antibody, such as in the light and/or heavy chain CDRs, and framework regions, and the resulting antibodies may be screened for binding to the target molecule or some other activity. Amino acid changes encompass one or more amino acid substitutions in a CDR, ranging from a single amino acid difference to the introduction of all possible permutations of amino acids within a given CDR, such as CDR3. In certain embodiments, the contribution of each residue within a CDR to target binding may be assessed by substituting at least one residue within the CDR with alanine (Lewis et al. (1995), *Mol. Immunol.* 32: 1065-72). In certain embodiments, residues which are not optimal for binding to the target molecule may then be changed in order to determine a more optimum sequence. In certain embodiments, variants may be generated by insertion of amino acids to increase the size of a CDR, such as CDR3. For example, most light chain CDR3 sequences are nine amino acids in length. In certain embodiments, light chain CDR3 sequences in an antibody which are shorter than nine residues may be optimized for binding to the target molecule by insertion of appropriate amino acids to increase the length of the CDR.

In certain embodiments, antibody or antigen binding domain variants comprise one or more amino acid changes in one or more of the heavy or light chain CDR1, CDR2 or CDR3 and optionally one or more of the heavy or light chain framework regions FR1, FR2 or FR3. In certain embodiments, amino acid changes comprise substitutions, deletions and/or insertions of amino acid residues.

In certain embodiments, variants may be prepared by "chain shuffling" of either light or heavy chains. Marks et al., (1992), *Biotechnology* 10: 779-83. In certain embodiments, a single light (or heavy) chain is combined with a library having a repertoire of heavy (or light) chains and the resulting population is screened for a desired activity, such as binding to the target molecule. This technique may permit screening of a greater sample of different heavy (or light) chains in combination with a single light (or heavy) chain than is possible with libraries comprising repertoires of both heavy and light chains.

In certain embodiments, the specific binding partners of the invention may be bispecific. Bispecific specific binding partners can be of several configurations. In certain embodiments, bispecific antibodies resemble single antibodies (or antibody fragments) but have two different antigen binding sites (variable regions). In certain embodiments, bispecific antibodies can be produced by chemical techniques (see e.g., Kranz et al., *Proc. Natl. Acad. Sci. USA,* 78:5807 (1981)), by "polydoma" techniques (see U.S. Pat. No. 4,474,893 to Reading) or by recombinant DNA techniques.

In certain embodiments, the specific binding partners of the invention may also be heteroantibodies. Heteroantibodies are two or more antibodies, or antibody binding fragments (Fab) linked together, each antibody or fragment having a different specificity.

In certain embodiments, "humanized" antibodies are provided. Methods for humanizing non-human antibodies are well known in the art. Generally, a humanized antibody has one or more amino acid residues introduced into a human antibody from a source which is non-human. In general, non-human residues will be present in CDRs. In certain embodiments, humanization can be performed following methods known in the art (See, e.g., Jones et al., *Nature* 321, 522-525 (1986); Riechmann et al., *Nature,* 332, 323-327 (1988), Verhoeyen et al., *Science* 239, 1534-1536 (1988)), by substituting rodent complementarily-determining regions (CDRs) for the corresponding regions of a human antibody.

The ability to clone and reconstruct megabase-sized human loci in yeast artificial chromosomes (YACs) and to introduce them into the mouse germline provides an approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy could provide a source for production of fully human monoclonal antibodies (MAbs). In certain embodiments, fully human antibodies are expected to minimize the immunogenic and allergic responses intrinsic to mouse or mouse-derivatized Mabs, and thus, in certain embodiments, increase the efficacy and safety of the administered antibodies. In certain embodiments, fully human antibodies may be used in the treatment of chronic and recurring human diseases, such as osteoporosis, inflammation, autoimmunity, and cancer, which may involve repeated antibody administrations.

One can engineer mouse strains deficient in mouse antibody production with large fragments of the human Ig loci in anticipation that such mice would produce human antibodies in the absence of mouse antibodies. Large human Ig fragments may preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains may yield high affinity antibodies against any antigen of interest, including human antigens. Using the hybridoma technology, antigen-specific human MAbs with the desired specificity may be produced and selected.

In certain embodiments, specific binding partners, including chimeric, CDR-grafted, and humanized antibodies, can be produced by recombinant methods known in the art. In certain embodiments, nucleic acids encoding the antibodies are introduced into host cells and expressed using materials and procedures described herein and known in the art. In certain embodiments, the antibodies are produced in mammalian host cells, such as CHO cells. In certain embodiments, fully human antibodies may be produced by expression of recombinant DNA transfected into host cells or by expression in hybridoma cells as described above.

In certain embodiments, techniques for creating recombinant DNA versions of the antigen-binding regions of antibody molecules which bypass the generation of monoclonal antibodies are provided. In certain embodiments, antibody-specific messenger RNA molecules are extracted from immune system cells taken from an immunized animal, and transcribed into complementary DNA (cDNA). In certain embodiments, the cDNA is then cloned into a bacterial expression system. In certain embodiments, a bacteriophage lambda vector system having a leader sequence that causes the expressed Fab protein to migrate to the periplasmic space (between the bacterial cell membrane and the cell wall) or to be secreted may be used. In certain embodiments, one can rapidly generate and screen great numbers of functional Fab fragments for those which bind the antigen. Such target molecule specific binding partners (Fab fragments with specificity for the target molecule) are specifically encompassed within the term "antibody" as it is defined, discussed, and claimed herein.

In certain embodiments, chimeric antibodies may be produced by splicing the genes from a mouse antibody molecule of appropriate antigen-specificity together with genes from a human antibody molecule of appropriate biological activity, such as the ability to activate human complement and mediate ADCC. (Morrison et al., *Proc. Natl. Acad. Sci.,* 81:6851 (1984); Neuberger et al., *Nature,* 312:604 (1984)). In certain embodiments, a Fc region may be replaced with that of a different isotype. Specific binding partners such as antibodies produced by this technique are within the scope of certain embodiments of the invention.

In certain embodiments, the antibodies are fully human antibodies. In certain embodiments, the antibodies that bind target molecules are encoded by nucleic acid sequences which are naturally occurring somatic variants of human germline immunoglobulin nucleic acid sequence, and fragments, synthetic variants, derivatives and fusions thereof.

Such antibodies may be produced by any method known in the art. In certain embodiments, antibodies may be produced by immunization with a target antigen (any target polypeptide capable of eliciting an immune response, and optionally conjugated to a carrier) of transgenic animals (e.g., mice) that are capable of producing a repertoire of human antibodies in the absence of endogenous immunoglobulin production. See, for example, Jakobovits et al., *Proc. Natl. Acad. Sci.*, 90, 2551-2555 (1993); Jakobovits et al., *Nature*, 362, 255-258 (1993); Bruggermann et al., *Year in Immunol.*, 7, 33 (1993).

In certain embodiments, human antibodies may be generated through the in vitro screening of phage display antibody libraries. See Hoogenboom et al., *J. Mol. Biol.*, 227, 381 (1991); Marks et al., *J. Mol. Biol.*, 222, 581 (1991), incorporated herein by reference. Various antibody-containing phage display libraries have been described and may be readily prepared by one skilled in the art. In certain embodiments, libraries may contain a diversity of human antibody sequences, such as human Fab, Fv, and scFv fragments, that may be screened against an appropriate target. In certain embodiments, phage display libraries may comprise peptides or proteins other than antibodies which may be screened to identify specific binding partners of the target molecule.

An anti-idiotypic (anti-id) antibody is an antibody which recognizes unique determinants generally associated with the antigen-binding site of an antibody. An Id antibody may be prepared by immunizing an animal of the same species and genetic type (e.g., mouse strain) as the source of the monoclonal antibody with the monoclonal antibody to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein incorporated by reference in its entirety for any purpose. In certain embodiments, the anti-Id antibody may also be used as an "immunogen" to induce an immune response in yet another animal, producing a so-called anti-anti-Id antibody. In certain embodiments, the anti-anti-Id may be epitopically identical to the original monoclonal antibody which induced the anti-Id. Thus, in certain embodiments, by using antibodies to the idiotypic determinants of a mAb, it is possible to identify other clones expressing antibodies of identical specificity.

Naturally occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that may be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., Fundamental Immunology Ch. 7 (Paul, W., ed., 2nd ed. Raven Press, N.Y. (1989)) (incorporated by reference in its entirety for all purposes). The variable regions of each light/heavy chain pair typically form the antigen binding site.

The variable regions typically exhibit the same general structure of relatively conserved framework regions (FR) joined by three hyper variable regions, also called complementarity determining regions or CDRs. The CDRs from the two chains of each pair typically are aligned by the framework regions, which may enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987); Chothia et al. Nature 342:878-883 (1989).

The term "heavy chain" includes any polypeptide having sufficient variable region sequence to confer specificity for an antigen. The term "light chain" includes any polypeptide having sufficient variable region sequence to confer specificity for an antigen. A full-length heavy chain includes a variable region domain, $V_H$, and three constant region domains, $C_H1$, $C_H2$, and $C_H3$. The $V_H$ domain is at the amino-terminus of the polypeptide, and the $C_H3$ domain is at the carboxy-terminus. The term "heavy chain", as used herein, encompasses a full-length heavy chain and fragments thereof. A full-length light chain includes a variable region domain, $V_L$, and a constant region domain, $C_L$. Like the heavy chain, the variable region domain of the light chain is at the amino-terminus of the polypeptide. The term "light chain", as used herein, encompasses a full-length light chain and fragments thereof. A Fab fragment is comprised of one light chain and the $C_H1$ and variable regions of one heavy chain. The heavy chain of a Fab molecule cannot form a disulfide bond with another heavy chain molecule. A Fab' fragment contains one light chain and one heavy chain that contains more of the constant region, between the $C_H1$ and $C_H2$ domains, such that an interchain disulfide bond can be formed between two heavy chains to form a F(ab')2 molecule. The Fv region comprises the variable regions from both the heavy and light chains, but lacks the constant regions. Single-chain antibodies are Fv molecules in which the heavy and light chain variable regions have been connected by a flexible linker to form a single polypeptide chain which forms an antigen-binding region. Single chain antibodies are discussed in detail in WO 88/01649 and U.S. Pat. Nos. 4,946,778 and 5,260,203.

A bivalent antibody other than a "multispecific" or "multifunctional" antibody, in certain embodiments, typically is understood to have each of its binding sites identical.

An antibody substantially inhibits adhesion of a ligand to a receptor when an excess of antibody reduces the quantity of receptor bound to counterreceptor by at least about 20%, 40%, 60%, 80%, 85%, or more (as measured in an in vitro competitive binding assay).

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. In certain embodiments, an antibody is said to specifically bind an antigen when the dissociation constant is $\leq 1$ µM, in certain embodiments, when the dissociation constant is ≦100 nM, and in certain embodiments, when the dissociation constant is ≦10 nM.

The patent application WO 00/24782, published May 4, 2000, describes in detail various peptide generation techniques. That patent application further describes various derivatives and fusion molecules.

In certain embodiments, a peptide used as a specific binding partner may be comprised within a molecule of the formula $$(X^1)_a\text{—}F^1\text{—}(X^2)_b$$

wherein:
$F^1$ is a vehicle;
$X^1$ and $X^2$ are each independently selected from $-(L^1)_c\text{-}P^1$, $-(L^1)_c\text{-}P^1\text{-}(L^2)_d\text{-}P^2$, $-(L^1)_c\text{-}P^1\text{-}(L^2)_d\text{-}P^2\text{-}(L^3)_e\text{-}P^3$, and $-(L^1)_c\text{-}P^1\text{-}(L^2)_d\text{-}P^2\text{-}(L^3)_e\text{-}P^3\text{-}(L^4)_f\text{-}P^4$
$P^1$, $P^2$, $P^3$, and $P^4$ are each independently peptide sequences, wherein at least one is a specific binding partner;
$L^1$, $L^2$, $L^3$, and $L^4$ are each independently linkers; and
a, b, c, d, e, and f are each independently 0 or 1, provided that at least one of a and b is 1.

In certain embodiments, a molecule comprises a structure of the formula $$X^1\text{—}F^1$$

or $$F^1\text{—}X^2.$$

In certain embodiments, a molecule comprises a structure of the formula $$F^1\text{-}(L^1)_c\text{-}P^1.$$

or a structure of the formula $$F^1\text{-}(L^1)_c\text{-}P^1\text{-}(L^2)_d\text{-}P^2$$

wherein $P^1$ and/or $P^2$ is a specific binding partner for a target molecule.

In certain embodiments, the vehicle is an Fc domain. In certain embodiments, the Fc domain may be IgG Fc. In certain embodiments, the IgG Fc domain may be IgG1.

Certain Fc domains, linkers, and processes of preparation of the foregoing molecules are described, e.g., in WO 00/24782, published May 4, 2000.

Another class of specific binding partners are soluble receptor fragments. Certain soluble receptor fragments are identified in the figures:

| a. | the IL-1 receptor. | (SEQ ID NO. 7) |
| b. | TNFRI. | (SEQ ID NO. 8) |
| c. | TNFRII. | (SEQ ID NO. 9) |
| d. | CD40. | (SEQ ID NO. 10) |
| e. | CD30. | (SEQ ID NO. 11) |
| f. | ICOS. | (SEQ ID NO. 12) |
| g. | CD28. | (SEQ ID NO. 13) |
| h. | OX40. | (SEQ ID NO. 14) |
| i. | 4-1-BB. | (SEQ ID NO. 15) |
| j. | CD27. | (SEQ ID NO. 16) |
| k. | the IL-18 receptor. | (SEQ ID NO. 17) |
| l. | PD-1. | (SEQ ID NO. 18) |

Like the aforementioned peptides, in certain embodiments, these specific binding partners may be covalently linked to a vehicle. In certain embodiments, these specific binding partners may be covalently linked to an Fc domain.

In certain embodiments, peptide and polypeptide sequences may be from conservative and/or non-conservative modifications of the amino acid sequences of certain native molecules.

In certain embodiments, conservative modifications may produce molecules having functional and chemical characteristics similar to those of the molecule from which such modifications are made. In contrast, in certain embodiments, substantial modifications in the functional and/or chemical characteristics of the molecules may be accomplished by selecting substitutions in the amino acid sequence that differ significantly in their effect on maintaining (a) the structure of the molecular backbone in the area of the substitution, for example, as a sheet or helical conformation, (b) the charge or hydrophobicity of the molecule at the target site, or (c) the size of the molecule.

For example, in certain embodiments, a "conservative amino acid substitution" may involve a substitution of a native amino acid residue with a normative residue such that there is little or no effect on the polarity or charge of the amino acid residue at that position. Furthermore, in certain embodiments, any native residue in the polypeptide may also be substituted with alanine, as has been previously described for "alanine scanning mutagenesis" (see, for example, MacLennan et al., 1998, *Acta Physiol. Scand. Suppl.* 643:55-67; Sasaki et al., 1998, *Adv. Biophys.* 35:1-24, which discuss alanine scanning mutagenesis).

Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Desired amino acid substitutions (whether conservative or non-conservative) can be determined by those skilled in the art at the time such substitutions are desired. For example, in certain embodiments, amino acid substitutions can be used to identify important residues of the molecule sequence, or to increase or decrease the affinity of the molecules described herein.

Naturally occurring residues may be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human antibody that are homologous with non-human antibodies, or into the non-homologous regions of the molecule.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.*, 157:105-131 (1982). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Gys | Thr |
| Thr | Ser | Ser |
| Trp | Tyr, Phe | Tyr |
| Tyr | Trp, Phe, Thr, Ser | The |
| Val | Ile, Met, Leu, Phe, Ala, Norleucine | Leu |

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., *Curr. Op. in Biotech.*, 7(4):422-427 (1996), Chou et al., *Biochemistry*, 13(2):222-245 (1974); Chou et al., *Biochemistry*, 113(2):211-222 (1974); Chou et al., *Adv. Enzymol Relat. Areas Mol. Biol.*, 47:45-148 (1978); Chou et al., *Ann. Rev. Biochem.*, 47:251-276 and Chou et al., *Biophys. J.*, 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., *Nucl. Acid. Res.*, 27(1):244-247 (1999). It has been suggested (Brenner et al., *Curr. Op. Struct. Biol.*, 7(3): 369-376 (1997)) that there are a limited number of folds in a given polypeptide or protein and that once a critical number of structures have been resolved, structural prediction will become dramatically more accurate.

Additional methods of predicting secondary structure include "threading" (Jones, D., *Curr. Opin. Struct. Biol.*, 7(3):

377-87 (1997); Sippl et al., *Structure,* 4(1):15-19 (1996)), "profile analysis" (Bowie et al., *Science,* 253:164-170 (1991); Gribskov et al., *Meth. Enzym.,* 183:146-159 (1990); Gribskov et al., *Proc. Nat. Acad. Sci.,* 84(13):4355-4358 (1987)), and "evolutionary linkage" (See Holm, supra (1999), and Brenner, supra (1997)).

In certain embodiments, antibody variants include glycosylation variants wherein the number and/or type of glycosylation site has been altered compared to the amino acid sequences of the parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physicochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. *Nature* 354:105 (1991), which are each incorporated herein by reference.

The term "polypeptide fragment" as used herein refers to a polypeptide that has an amino-terminal and/or carboxy-terminal deletion. In certain embodiments, fragments are at least 5 to 467 amino acids long. It will be appreciated that in certain embodiments, fragments are at least 5, 6, 8, 10, 14, 20, 50, 70, 100, 150, 200, 250, 300, 350, 400, or 450 amino acids long.

Peptide analogs are commonly used in the pharmaceutical industry as non-peptide drugs with properties analogous to those of the template peptide. These types of non-peptide compound are termed "peptide mimetics" or "peptidomimetics". Fauchere, *J. Adv. Drug Res.* 15:29 (1986); Veber and Freidinger TINS p. 392 (1985); and Evans et al. *J. Med. Chem.* 30:1229 (1987), which are incorporated herein by reference for any purpose. Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: $-CH_2NH-$, $-CH_2S-$, $-CH_2-CH_2-$, $-CH=CH$-(cis and trans), $-COCH_2-$, $-CH(OH)CH_2-$, and $-CH_2SO-$, by methods well known in the art. Systematic substitution of one or more amino acids of a consensus sequence with a D-amino acid of the same type (e.g., D-lysine in place of L-lysine) may be used in certain embodiments to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference for any purpose); for example, by adding internal cysteine residues capable of forming intramolecular disulfide bridges which cyclize the peptide.

Various biological or chemical methods for producing a proteinaceous specific binding partner are available.

In certain embodiments, biological methods are used for producing sufficient quantities of a specific binding partner. In certain embodiments, standard recombinant DNA techniques are useful for the production of antibodies and antigen binding domains. Certain expression vectors, host cells and methods for recovery of the expressed product are described below.

In certain embodiments, a nucleic acid molecule encoding an antibody or antigen binding domain is inserted into an appropriate expression vector using standard ligation techniques. In certain embodiments, the vector may be selected to be functional in the particular host cell employed (i.e., the vector is compatible with the host cell machinery such that amplification of the gene and/or expression of the gene can occur). In certain embodiments, a nucleic acid molecule encoding an antibody may be amplified/expressed in prokaryotic, yeast, insect (baculovirus systems) and/or eukaryotic host cells. In certain embodiments, selection of the host cell will take into account, in part, whether an antibody is to be post-translationally modified (e.g., glycosylated and/or phosphorylated). In certain embodiments, yeast, insect, or mammalian host cells are selected to facilitate post-translational modifications. For a review of expression vectors, see, e.g., Meth. Enz. v. 185, (D. V. Goeddel, ed.), Academic Press Inc., San Diego, Calif. (1990).

In certain embodiments, expression vectors used in any host cells will contain one or more of the following components: a promoter, one or more enhancer sequences, an origin of replication, a transcriptional termination sequence, a complete intron sequence containing a donor and acceptor splice site, a leader sequence for secretion, a ribosome binding site, a polyadenylation sequence, a polylinker region for inserting the nucleic acid encoding the polypeptide to be expressed, and a selectable marker element. Such sequences are discussed in more detail below.

Exemplary vector components include, but are not limited to, homologous (i.e., from the same species and/or strain as the host cell), heterologous (i.e., from a species other than the host cell species or strain), hybrid (i.e., a combination of different sequences from more than one source), synthetic, or native sequences which normally function to regulate immunoglobulin expression. In certain embodiments, a source of vector components may be any prokaryotic or eukaryotic organism, any vertebrate or invertebrate organism, or any plant, provided that the components are functional in, and can be activated by, the host cell machinery.

In certain embodiments, an origin of replication is selected based upon the type of host cell being used for expression. In certain embodiments, the origin of replication from the plasmid pBR322 (Product No. 303-3ss, New England Biolabs, Beverly, Mass.) is suitable for most Gram-negative bacteria while, in certain embodiments, various origins from SV40, polyoma, adenovirus, vesicular stomatitis virus (VSV) or papillomaviruses (such as HPV or BPV) are useful for cloning vectors in mammalian cells. In certain embodiments, the origin of replication component is not needed for mammalian expression vectors (for example, the SV40 origin is often used only because it contains the early promoter).

In certain embodiments, a transcription termination sequence may be located 3' of the end of a polypeptide coding regions and serves to terminate transcription. In certain embodiments, a transcription termination sequence in prokaryotic cells is a G-C rich fragment followed by a poly T sequence. While certain sequences may be easily cloned from a library or even purchased commercially as part of a vectors in certain embodiments, sequences can also be readily synthesized using methods for nucleic acid synthesis such as those described above.

In certain embodiments, a selectable marker gene element encodes a protein necessary for the survival and growth of a host cell grown in a selective culture medium. Exemplary, but nonlimiting, selection marker genes include those that encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Exemplary selectable markers include, but are not limited to, the kanamycin resistance gene, the ampicillin resistance gene, and the tetracycline resistance gene. In certain embodiments, a neomycin resistance gene may be used for selection in prokaryotic and eukaryotic host cells.

In certain embodiments, other selection genes may be used to amplify the gene which will be expressed. Amplification is the process wherein genes which are in greater demand for the production of a protein critical for growth are reiterated in tandem within the chromosomes of successive generations of recombinant cells. In certain embodiments, selectable markers for mammalian cells may be dihydrofolate reductase (DHFR) and thymidine kinase. In certain embodiments, the mammalian cell transformants are placed under selection pressure which only the transformants are uniquely adapted to survive by virtue of the marker present in the vector. Selection pressure is imposed by culturing the transformed cells under conditions in which the concentration of selection partner in the medium is successively changed, thereby leading to amplification of both the selection gene and the DNA that encodes an antibody. In certain embodiments, increased quantities of an antibody are synthesized from the amplified DNA.

A ribosome binding site is typically present for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

In certain embodiments, a leader or signal sequence may be used to direct secretion of a polypeptide. In certain embodiments, a signal sequence may be positioned within or directly at the 5' end of a polypeptide coding region. Many signal sequences have been identified and, in certain embodiments, may be selected based upon the host cell used for expression. In certain embodiments, a signal sequence may be homologous (naturally occurring) or heterologous to a nucleic acid sequence encoding an antibody or antigen binding domain. In certain embodiments, a heterologous signal sequence selected should be one that is recognized and processed, i.e., cleaved by a signal peptidase, by the host cell. In certain embodiments involving prokaryotic host cells that do not recognize and process a native immunoglobulin signal sequence, the signal sequence may be substituted with a prokaryotic signal sequence selected, e.g., from alkaline phosphatase, penicillinase, or heat-stable enterotoxin II leaders. In certain embodiments, for yeast secretion, a native immunoglobulin signal sequence may be substituted by a yeast leader sequence. Exemplary yeast leader sequences include, but are not limited to, yeast invertase, alpha factor, or acid phosphatase leaders. In certain embodiments, mammalian cell expression using the native signal sequence may be satisfactory. In certain embodiments, other mammalian signal sequences may be suitable.

In certain embodiments, secretion of an antibody or antigen binding domain from a host cell will result in the removal of the signal peptide from the antibody. Thus, in such embodiments, the mature antibody will lack any leader or signal sequence.

In certain embodiments, such as where glycosylation is desired in a eukaryotic host cell expression system, one may manipulate the various presequences to improve glycosylation or yield. In certain embodiments, one may alter the peptidase cleavage site of a particular signal peptide, or add presequences, which also may affect glycosylation. In certain embodiments, the final protein product may have, in the −1 position (relative to the first amino acid of the mature protein) one or more additional amino acids incident to expression, which may not have been totally removed. In certain embodiments, the final protein product may have one or two amino acids found in the peptidase cleavage site, attached to the N-terminus. In certain embodiments, use of some enzyme cleavage sites may result in a slightly truncated form of the desired polypeptide, if the enzyme cuts at such area within the mature polypeptide.

In certain embodiments, the expression vectors may contain a promoter that is recognized by the host organism and operably linked to a nucleic acid molecule encoding an antibody or antigen binding domain. In certain embodiments, a native or heterologous promoter may be used depending on the host cell used for expression and the yield of protein desired.

Exemplary promoters for use with prokaryotic hosts include, but are not limited to, beta-lactamase and lactose promoter systems; alkaline phosphatase; a tryptophan (trp) promoter system; and hybrid promoters such as the tac promoter. In certain embodiments, other known bacterial promoters may be used. The sequences of known bacterial promoters have been published, thereby enabling one skilled in the art to ligate them to the desired DNA sequence(s), using linkers or adapters as needed to supply any desired restriction sites.

Suitable promoters for use with yeast hosts are also well known in the art. In certain embodiments, yeast enhancers are advantageously used with yeast promoters. Suitable promoters for use with mammalian host cells are well known. Exemplary promoters for use with mammalian host cells include, but are not limited to, those obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40). Exemplary mammalian promoters include, but are not limited to, heterologous mammalian promoters. Exemplary heterologous mammalian promoters include, but are not limited to, heat-shock promoters and the actin promoter.

Exemplary promoters which may be used for expressing specific binding partners include, but are not limited to, the SV40 early promoter region (Benoist and Chambon (1981), Nature, 290:304-310); the CMV promoter; the promoter contained in the 3' long terminal repeat of Rous sarcoma virus (Yamamoto et al. (1980), Cell, 22: 787-97); the herpes thymidine kinase promoter (Wagner et al. (1981), Proc. Natl. Acad. Sci. U.S., 78: 1444-5); the regulatory sequences of the metallothionine gene (Brinster et al. (1982), Nature, 296: 39-42); prokaryotic expression vectors such as the beta-lactamase promoter (Villa-Kamaroff et al. (1978), Proc. Natl. Acad. Sci. U.S.A., 75: 3727-31); and the tac promoter (De-Boer, et al. (1983), Proc. Natl. Acad. Sci. U.S.A., 80: 21-25).

In certain embodiments, animal transcriptional control regions, which exhibit tissue specificity may be used in transgenic animals. Exemplary transcriptional control regions for use with tissue specific expression in transgenic animals include, but are not limited to, the elastase I gene control region which is active in pancreatic acinar cells (Swift et al. (1984), Cell, 38: 639-46; Ornitz et al. (1986), Cold Spring Harbor Symp. Quant. Biol. 50: 399-409; MacDonald (1987), Hepatology, 7: 425-515); the insulin gene control region which is active in pancreatic beta cells (Hanahan (1985), Nature, 315: 115-122); the immunoglobulin gene control region which is active in lymphoid cells (Grosschedl et al. (1984), Cell, 38: 647-58; Adames et al. (1985), Nature, 318: 533-8; Alexander et al. (1987), Mol. Cell. Biol., 7: 1436-44); the mouse mammary tumor virus control region which is active in testicular, breast, lymphoid and mast cells (Leder et al. (1986), Cell, 45: 485-95); albumin gene control region which is active in liver (Pinkert et al. (1987), Genes and Devel., 1: 268-76); the alphafetoprotein gene control region which is active in liver (Krumlauf et al. (1987), Mol. Cell. Biol., 5: 1639-48; Hammer et al. (1987), Science, 235: 53-58); the alpha 1-antitrypsin gene control region which is active in the liver (Kelsey et al. (1987), Genes and Devel., 1: 161-171); the beta-globin gene control region which is active in myeloid cells (Mogram et al. (1985), Nature, 315: 338-340; Kollias et al. (1986), Cell, 46: 89-94), the myelin basic protein gene control region which is active in oligodendrocyte cells in the brain (Readhead et al. (1987), Cell, 48: 703-712); the myosin light chain-2 gene control region which is active in skeletal muscle (Sani (1985), Nature, 314: 283-286); and the gonadotropic releasing hormone gene control region which is active in the hypothalamus (Mason et al. (1986), Science, 234: 1372-8).

In certain embodiments, an enhancer sequence may be inserted into the vector to increase transcription in eucaryotic host cells. Exemplary enhancer sequences from mammalian genes include, but are not limited to, globin, elastase, albumin, alpha-feto-protein, and insulin. In certain embodiments, an enhancer from a virus will be used. Exemplary enhancer sequences for the activation of eukaryotic promoters include, but are not limited to, the SV40 enhancer, the cytomegalovirus early promoter enhancer, the polyoma enhancer, and adenovirus enhancers are exemplary enhancing elements. In certain embodiments, an enhancer may be spliced into the vector at a position 5' or 3' to the polypeptide coding region. In certain embodiments, the enhancer is located at a site 5' from the promoter.

In certain embodiments, vectors are those which are compatible with at least one of bacterial, insect, and mammalian host cells. Exemplary vectors include, but are not limited to, pCRII, pCR3, and pcDNA3.1 (Invitrogen Company, San Diego, Calif.), pBSII (Stratagene Company, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII; Invitrogen), pDSR-alpha (PCT Publication No. WO90/14363) and pFastBacDual (Gibco/BRL, Grand Island, N.Y.).

Exemplary vectors include, but are not limited to, cosmids, plasmids and modified viruses compatible with the selected host cell. In certain embodiments, the vectors may include plasmids including, but not limited to, Bluescript® plasmid derivatives (a high copy number ColE1-based phagemid, Stratagene Cloning Systems Inc., La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), and mammalian, yeast or virus vectors such as a baculovirus expression system (pBacPAK plasmid derivatives, Clontech, Palo Alto, Calif.). In certain embodiments, the recombinant molecules may be introduced into host cells via transformation, transfection, infection, electroporation, or other known techniques.

In certain embodiments, host cells may be prokaryotic host cells (such as E. coli) or eukaryotic host cells (such as a yeast cell, an insect cell, or a vertebrate cell). In certain embodiments, prokaryotic host cells such as E. coli produce unglycosylated protein; for example, unglyclosylated shBCMA and unglycosylated shTACI, which may possess advantages over the glycosylated eukaryotic molecules. In certain embodiments, the host cell, when cultured under appropriate conditions, expresses an antibody or antigen binding domain of the invention which can subsequently be collected from the culture medium (if the host cell secretes it into the medium) or directly from the host cell producing it (if it is not secreted). In certain embodiments, selection of an appropriate host cell will take into account various factors, such as desired expression levels, polypeptide modifications that are desirable or necessary for activity, such as glycosylation or phosphorylation, and/or ease of folding into a biologically active molecule.

A number of suitable host cells are known in the art and many are available from the American Type Culture Collection (ATCC), Manassas, Va. Exemplary host cells include, but are not limited to, mammalian cells, such as Chinese hamster ovary cells (CHO) (ATCC No. CCL61) CHO DHFR-cells (Urlaub et al. (1980), Proc. Natl. Acad. Sci. USA 97, 4216-20), human embryonic kidney (HEK) 293 or 293T cells (ATCC No. CRL1573), and 3T3 cells (ATCC No. CCL92). The selection of suitable mammalian host cells and methods for transformation, culture, amplification, screening and product production and purification are known in the art. Exemplary host cells include, but are not limited to, the monkey COS-1 (ATCC No. CRL1650) and COS-7 cell lines (ATCC No. CRL1651), and the CV-1 cell line (ATCC No. CCL70). Exemplary mammalian host cells include, but are not limited to, primate cell lines and rodent cell lines, including transformed cell lines. Exemplary host cells include, but are not limited to, normal diploid cells, cell strains derived from in vitro culture of primary tissue, and primary explants. In certain embodiments, candidate cells may be genotypically deficient in the selection gene, or may contain a dominantly acting selection gene. Exemplary host cells include, but are not limited to, mouse neuroblastoma N2A cells, HeLa, mouse L-929 cells, 3T3 lines derived from Swiss, Balb-c or NIH mice, BHK or HaK hamster cell lines, which are available from the American Type Culture Collection, Manassas, Va.). Each of these cell lines is known by and available to those skilled in the art of protein expression.

In certain embodiments, the host cells may be bacterial cells. Exemplary bacterial host cells include, but are no limited to, various strains of E. coli (e.g., HB101, (ATCC No. 33694) DH5α, DH10, and MC1061 (ATCC No. 53338)). Exemplary host cells also include, but are not limited to, various strains of Pseudomonas spp., B. subtilis, other Bacillus spp., Streptomyces spp.

Many strains of yeast cells known to those skilled in the art are also available as host cells for expression of polypeptides. In certain embodiments, the host cell may be Saccharomyces cerivisae.

In certain embodiments, insect cell systems may be used. Certain such systems are described, for example, in Kitts et al. (1993), Biotechniques, 14: 810-7, Lucklow (1993), Curr. Opin. Biotechnol., 4: 564-72, and Lucklow et al. (1993), J. Virol., 67: 4566-79. Exemplary insect cells include, but are not limited to, Sf-9 and Hi5 (Invitrogen, Carlsbad, Calif.).

In certain embodiments, transformation or transfection of a nucleic acid molecule encoding a specific binding partner into a selected host cell may be accomplished by well known methods including methods such as calcium chloride, electroporation, microinjection, lipofection or the DEAE-dextran method. In certain embodiments, the method selected will in part be a function of the type of host cell to be used. These methods and other suitable methods are well known to the skilled artisan, and are set forth, for example, in Sambrook et al. Molecular Cloning: A Laboratory Manual (2d ed., Cold Spring Harbor Laboratory Press, Cold Spring Harbor, N.Y. (1989)).

In certain embodiments, transgenic animals may be used to express glycosylated specific binding partners, such as antibodies and antigen binding domain. In certain embodiments, one may use a transgenic milk-producing animal (a cow or goat, for example) and obtain glycosylated binding partners in the animal milk. In certain embodiments, one may use plants to produce glycosylated specific binding partners.

Host cells comprising (as by transformation or transfection) an expression vector encoding a specific binding partner of the target molecule may be cultured using standard media well known to the skilled artisan. In certain embodiments, the media may contain all nutrients necessary for the growth and survival of the cells. In certain embodiments, E. coli cells may be cultured in Luria Broth (LB) and/or Terrific Broth (TB). Exemplary media for culturing eukaryotic cells include, but are not limited to, RPMI 1640, MEM, DMEM, all of which may be supplemented with serum and/or growth factors according to the particular cell line being cultured. In certain embodiments, insect cells may be cultured in Grace's medium supplemented with yeastolate, lactalbumin hydrolysate, and/or fetal calf serum.

In certain embodiments, an antibiotic or other compound useful for selective growth of transfected or transformed cells is added as a supplement to the media. In certain embodiments, the compound to be used is chosen in view of the selectable marker element present on the plasmid with which the host cell was transformed. In certain embodiments, where the selectable marker element is kanamycin resistance, the compound added to the culture medium will be kanamycin. Exemplary compounds for selective growth include, but are not limited to, ampicillin, tetracycline and neomycin.

In certain embodiments, the amount of an antibody or antigen binding domain produced by a host cell can be evaluated using standard methods known in the art. Exemplary methods include, but are not limited to, Western blot analysis, SDS-polyacrylamide gel electrophoresis, non-denaturing gel electrophoresis, HPLC separation, immunoprecipitation, and activity assays.

In certain embodiments, purification of a specific binding partner that has been secreted into the cell media may be accomplished using a variety of techniques including affinity, immunoaffinity or ion exchange chromatography, molecular sieve chromatography, preparative gel electrophoresis or isoelectric focusing, chromatofocusing, and high pressure liquid chromatography. In certain embodiments, antibodies comprising a Fc region may be conveniently purified by affinity chromatography with Protein A, which selectively binds the Fc region. In certain embodiments, modified forms of an antibody or antigen binding domain may be prepared with affinity tags, such as hexahistidine or other small peptide such as FLAG (Eastman Kodak Co., New Haven, Conn.) or myc (Invitrogen) at either the carboxyl or amino terminus and purified by a one-step affinity column. In certain embodiments, polyhistidine binds with great affinity and specificity to nickel, thus an affinity column of nickel (such as the Qiagen® nickel columns) can be used for purification of polyhistidine-tagged specific binding partners. See for example, Ausubel et al., eds. (1993), Current Protocols in Molecular Biology, Section 10.11.8, John Wiley & Sons, New York. In certain embodiments, more than one purification step may be used.

In certain embodiments, specific binding partners which are expressed in procaryotic host cells may be present in soluble form either in the periplasmic space or in the cytoplasm or in an insoluble form as part of intracellular inclusion bodies. In certain embodiments, specific binding partners can be extracted from the host cell using any standard technique known to the skilled artisan. In certain embodiments, the host cells can be lysed to release the contents of the periplasm/cytoplasm by French press, homogenization, and/or sonication followed by centrifugation.

In certain embodiments, soluble forms of an antibody or antigen binding domain present either in the cytoplasm or released from the periplasmic space may be further purified using methods known in the art. In certain embodiments, Fab fragments are released from the bacterial periplasmic space by osmotic shock techniques.

If an antibody or antigen binding domain has formed inclusion bodies, they may often bind to the inner and/or outer cellular membranes and thus will be found primarily in the pellet material after centrifugation. In certain embodiments, the pellet material may then be treated at pH extremes or with a chaotropic partner such as a detergent, guanidine, guanidine derivatives, urea, or urea derivatives in the presence of a reducing partner such as dithiothreitol at alkaline pH or tris carboxyethyl phosphine at acid pH to release, break apart, and solubilize the inclusion bodies. In certain embodiments, the soluble specific binding partner may then be analyzed using gel electrophoresis, immunoprecipitation or the like. In certain embodiments, a solublized antibody or antigen binding domain may be isolated using standard methods such as those set forth below and in Marston et al. (1990), Meth. Enz., 182: 264-75.

In certain embodiments, an antibody or antigen binding domain may not be biologically active upon isolation. In certain embodiments, methods for "refolding" or converting the polypeptide to its tertiary structure and generating disulfide linkages, may be used to restore biological activity. In certain embodiments, the biological activity may be restored by exposing the solubilized polypeptide to a pH usually above 7 in the presence of a particular concentration of a chaotrope. The selection of chaotrope is very similar to the choices used for inclusion body solubilization, but, in certain embodiments, the chaotrope is used at a lower concentration and is not necessarily the same as chaotropes used for the solubilization. In certain embodiments, the refolding/oxidation solution will also contain a reducing partner or the reducing partner plus its oxidized form in a specific ratio to generate a particular redox potential allowing for disulfide shuffling to occur in the formation of the protein's cysteine bridge(s). Exemplary redox couples include, but are not limited to, cysteine/cystamine, glutathione (GSH)/dithiobis GSH, cupric chloride, dithiothreitol(DTT)/dithiane DTT, and 2-mercaptoethanol(bME)/dithio-b(ME). In certain embodiments, a cosolvent may be used or may be needed to increase the efficiency of the refolding and exemplary repartners used for this purpose include, but are not limited to, glycerol, polyethylene glycol of various molecular weights, arginine, and related molecules.

In certain embodiments, specific binding partners may be prepared by chemical synthesis methods. In certain embodiments, the chemical synthesis method may incorporate solid phase peptide synthesis. In certain embodiments, the chemical synthesis methods may use techniques known in the art such as those set forth by Merrifield et al. (1963), *J. Am. Chem. Soc.*, 85: 2149; Houghten et al. (1985), *Proc Natl Acad. Sci. USA*, 82: 5132; and Stewart and Young (1984), *Solid Phase Peptide Synthesis*, Pierce Chemical Co., Rockford, Ill. In certain embodiments, polypeptides may be synthesized with or without a methionine on the amino terminus. In certain embodiments, chemically synthesized antibodies and antigen binding domains may be oxidized using methods set forth in these references to form disulfide bridges. In certain embodiments, antibodies so prepared will retain at least one biological activity associated with a native or recombinantly produced antibody or antigen binding domain.

In certain instances, single anti-cytokine therapy or a combination of anti-cytokine therapies (inhibitors of TNF, IL-1 etc.) have been successfully used, but with some limitations because of activated immune T and B cells. In certain instances, these therapies also involve regular treatment during the course of chronic diseases.

For ongoing autoimmune responses, in certain instances, inhibitors blocking the T cell activation have been used in animals and human inflammatory diseases with limited success. One of the reasons for this limitation is the proinflammatory cytokine environment at the site of inflammation. A good example is CTLA-4 therapy, which modulates collagen-induced arthritis (CIA) when mice are treated from induction of arthritis. Such treatment may fail if started at the time of disease onset (or ongoing autoimmune response), suggesting that proinflammatory cytokines are more important than T cells at the time of inflammation. Alternatively, activation of T cells cannot be blocked at this time by CTLA-4.

Interleukin-1 (IL-1) is an anti-inflammatory cytokine. In certain instances, IL-1 is a mediator in many diseases and medical conditions. In certain instances, IL-1 is manufactured by cells of the macrophage/monocyte lineage. In certain instances, IL-1 is produced in two forms: IL-1 alpha (IL-1α) and IL-1 beta (IL-1β).

A disease or medical condition is considered to be an "interleukin-1 mediated disease" if the spontaneous or experimental disease or medical condition is associated with elevated levels of IL-1 in bodily fluids or tissue and/or if cells or tissues taken from the body produce elevated levels of IL-1 in culture. In certain embodiments, such interleukin-1 mediated diseases are also recognized by the following additional two conditions: (1) pathological findings associated with the disease or medical condition can be mimicked experimentally in animals by administration of IL-1 or upregulation of expression of IL-1; and (2) a pathology induced in experimental animal models of the disease or medical condition can be inhibited or abolished by treatment with agents that inhibit the action of IL-1. In certain embodiments, one or more of the above conditions are met in an IL-1-mediated disease. In certain embodiments, all three of the conditions are met in an IL-1-mediated disease.

Acute and chronic interleukin-1 (IL-1)-mediated diseases include, but are not limited to, the following: acute pancreatitis; amyotrophic lateral sclerosis (ALS, or Lou Gehrig's disease); Alzheimer's disease; cachexia/anorexia, including, but not limited to, AIDS-induced cachexia; asthma and other pulmonary diseases; atherosclerosis; autoimmune vasculitis; chronic fatigue syndrome; *Clostridium* associated illnesses, including, but not limited to, *Clostridium*-associated diarrhea; coronary conditions and indications, including, but not limited to, congestive heart failure, coronary restenosis, myocardial infarction, myocardial dysfunction (e.g., related to sepsis), and coronary artery bypass graft; cancer, including, but not limited to, leukemias, including, but not limited to, multiple myeloma leukemia and myelogenous (e.g., AML and CML), and tumor metastasis; diabetes (including, but not limited to, insulin-dependent diabetes); endometriosis; fever; fibromyalgia; glomerulonephritis; graft versus host disease and/or transplant rejection; hemohorragic shock; hyperalgesia; inflammatory bowel disease; inflammatory conditions of a joint, including, but not limited to, osteoarthritis, psoriatic arthritis, and rheumatoid arthritis; inflammatory eye disease, including, but not limited to, those associated with, for example, corneal transplant; ischemia, including, but not limited to, cerebral ischemia (including, but not limited to, brain injury as a result of, e.g., trauma, epilepsy, hemorrhage or stroke, each of which may lead to neurodegeneration); Kawasaki's disease; learning impairment; lung diseases (including, but not limited to, acute respiratory distress syndrome, or ARDS); multiple sclerosis; myopathies (e.g., muscle protein metabolism, including, but not limited to, muscle protein metabolism in sepsis); neurotoxicity (including, but not limited to, such condition induced by HIV); osteoporosis; pain, including, but not limited to, cancer-related pain; Parkinson's disease; periodontal disease; pre-term labor; psoriasis; reperfusion injury; septic shock; side effects from radiation therapy; temporal mandibular joint disease; sleep disturbance; uveitis; and an inflammatory condition resulting from, e.g., strain, sprain, cartilage damage, trauma, orthopedic surgery, infection, or other disease processes.

In certain embodiments, an IL-1 inhibitor may be any protein or molecule capable of specifically preventing activation of cellular receptors to IL-1, which may result from any number of mechanisms. Exemplary mechanisms include, but are not limited to, downregulating IL-1 production, binding free IL-1, interfering with IL-1 binding to its receptor, interfering with formation of the IL-1 receptor complex (i.e., association of IL-1 receptor with IL-1 receptor accessory protein), and interfering with modulation of IL-1 signaling after binding to its receptor.

Certain interleukin-1 inhibitors include, but are not limited to, IL-1 receptor antagonists, including, but not limited to, Kineret™, IL-1ra, IL-1ra variants, and IL-1ra derivatives, which are collectively termed "IL-1ra proteins;" anti-IL-1 receptor monoclonal antibodies (see, e.g., EP 623674, which is hereby incorporated by reference for any purpose); IL-1 binding proteins, including, but not limited to, soluble IL-1 receptors (see, e.g., U.S. Pat. No. 5,492,888, U.S. Pat. No. 5,488,032, and U.S. Pat. No. 5,464,937, U.S. Pat. No. 5,319,071, and U.S. Pat. No. 5,180,812, which are hereby incorporated by reference for any purpose); anti-IL-1 monoclonal antibodies (see, e.g., WO 9501997, WO 9402627, WO 9006371, U.S. Pat. No. 4,935,343, EP 364778, EP 267611 and EP 220063, which are hereby incorporated by reference for any purpose); IL-1 receptor accessory proteins and antibodies thereto (see, e.g., WO 96/23067 and WO 99/37773, which are hereby incorporated by reference for any purpose); inhibitors of interleukin-1 beta converting enzyme (ICE) or caspase I (see, e.g., WO 99/46248, WO 99/47545, and WO 99/47154, which are hereby incorporated by reference for any purpose), which may be used to inhibit IL-1 beta production and secretion; interleukin-1 beta protease inhibitors; IL-1 inhibitory peptides and such peptides linked to half-life extending vehicles; which are described in WO 99/25044; and other compounds and proteins that block in vivo synthesis or extracellular release of IL-1.

Exemplary IL-1 inhibitors are disclosed, e.g., in U.S. Pat. Nos. 5,747,444; 5,359,032; 5,608,035; 5,843,905; 5,359,032; 5,866,576; 5,869,660; 5,869,315; 5,872,095; 5,955,480; 5,965,564; International (WO) patent applications 98/21957, 96/09323, 91/17184, 96/40907, 98/32733, 98/42325, 98/44940, 98/47892, 98/56377, 99/03837, 99/06426, 99/06042, 91/17249, 98/32733, 98/17661, 97/08174, 95/34326, 99/36426, 99/36415; European (EP) patent applications 534978 and 894795; and French patent application FR 2762514. The disclosures of all of the aforementioned references are hereby incorporated by reference for any purpose.

Interleukin-1 receptor antagonist (IL-1ra) is a human protein that acts as a natural inhibitor of interleukin-1 and is a member of the IL-1 family, which includes IL-1α and IL-1β. Certain receptor antagonists, including IL-1ra and variants and derivatives thereof, as well as methods of making and using them, are described in U.S. Pat. No. 5,075,222; WO 91/08285; WO 91/17184; AU 9173636; WO 92/16221; WO 93/21946; WO 94/06457; WO 94/21275; FR 2706772; WO 94/21235; DE 4219626, WO 94/20517; WO 96/22793; WO 97/28828; and WO 99/36541, which are incorporated herein by reference for any purpose. In certain embodiments, an IL-1 receptor antagonist may be glycosylated. In certain embodiments, an IL-1 receptor antagonist may be non-glycosylated.

Three forms of IL-1ra and variants thereof are described in U.S. Pat. No. 5,075,222 (the '222 patent). The first form IL-1raα (called "IL-1i", in the '222 patent), is characterized as a 22-23 kD molecule on SDS-PAGE with an approximate isoelectric point of 4.8, which elutes from a Mono Q FPLC column at around 52 mM NaCl in Tris buffer, pH 7.6. The second form, IL-1raβ, is characterized as a 22-23 kD protein, which elutes from a Mono Q column at 48 mM NaCl. Both IL-1raα and IL-1raβ are glycosylated. The third form, IL-1rax, is characterized as a 20 kD protein, which elutes from a Mono Q column at 48 mM NaCl and is non-glycosylated. The '222 patent also describes certain methods for isolating genes that code for the inhibitors, cloning those genes in suitable vectors, transforming and transfecting those genes into certain cell types, and expressing those genes to produce the inhibitors.

KIN2 is a variant of IL-1ra fused to a Fc molecule. The sequence of KIN2 is disclosed in SEQ ID NO. 3. Further information on expression and purification of KIN2 is in U.S. Pat. No. 6,294,170.

In certain embodiments, deletions, insertions, and/or substitutions (individually or collectively referred to as "variant(s)") are made within the amino acid sequences of IL-1ra. In certain embodiments, an IL-1ra variant is biologically active (e.g., possesses the ability to inhibit IL-1).

Certain diseases and medical conditions are mediated by TNF and may be categorized as inflammatory conditions. As used herein, a "TNF-mediated disease" includes, but is not limited to, a disease or medical condition that is associated with elevated levels of TNF in bodily fluids or tissue and/or in which cells or tissues taken from the body produce elevated levels of TNF in culture. In certain embodiments, a disease is a TNF-mediated disease if (1) pathological findings associated with the disease or medical condition can be mimicked experimentally in animals by the administration or upregulation of expression of TNF and/or (2) a pathology induced in experimental animal models of the disease or medical condition can be inhibited or abolished by treatment with agents that inhibit the action of TNF.

Certain acute and chronic TNF-mediated diseases include, but are not limited to: cachexia and anorexia; cancer, including, but not limited to, leukemia; chronic fatigue syndrome; coronary conditions and/or indications, including, but not limited to, congestive heart failure, coronary restenosis, myocardial infarction, myocardial dysfunction (including but not limited to, such condition related to sepsis), and coronary artery bypass graft; depression; diabetes, including, but not limited to, juvenile onset Type 1 diabetes, diabetes mellitus, and insulin resistance (including, but not limited to, insulin resistance associated with obesity); endometriosis, endometritis, and related conditions; fibromyalgia and analgesia; graft versus host rejection; hyperalgesia; inflammatory bowel diseases, including, but not limited to, Crohn's disease and *Clostridium difficile*-associated diarrhea; ischemia, including, but not limited to, cerebral ischemia, which includes, but is not limited to, brain injury as a result of trauma, epilepsy, hemorrhage, and/or stroke; lung disease, including, but not limited to, adult respiratory distress syndrome, asthma, and pulmonary fibrosis; multiple sclerosis; neuroinflammatory diseases; ocular diseases and conditions, including, but not limited to, corneal transplant, ocular degeneration and uveitis; pain, including, but not limited to, cancer-related pain; pancreatitis; periodontal diseases; Pityriasis rubra pilaris (PRP); prostatitis, including bacterial and non-bacterial prostatitis, and related conditions; psoriasis and related conditions; pulmonary fibrosis; reperfusion injury; rheumatic diseases, including, but not limited to, rheumatoid arthritis, osteoarthritis, juvenile arthritis (including, but not limited to, juvenile rheumatoid arthritis), seronegative polyarthritis, ankylosing spondylitis, Reiter's syndrome and reactive arthritis, Still's disease, psoriatic arthritis, enteropathic arthritis, polymyositis, dermatomyositis, scleroderma, systemic sclerosis, vasculitis (e.g., Kawasaki's disease), cerebral vasculitis, Lyme disease, staphylococcal-induced ("septic") arthritis, Sjögren's syndrome, rheumatic fever, polychondritis and polymyalgia rheumatica and giant cell arteritis); septic shock; side effects from radiation therapy; systemic lupus erythematosus (SLE); temporal mandibular joint disease; thyroiditis; and tissue transplantation and/or an inflammatory condition, e.g., resulting from strain, sprain, cartilage damage, trauma, orthopedic surgery, infection (e.g., HIV, *Clostridium difficile* and related species) or other disease process.

In certain embodiments, TNF inhibitors may act by at least one of downregulating or inhibiting TNF production, binding free TNF, interfering with TNF binding to its receptor, and interfering with modulation of TNF signaling after binding to its receptor. The term "TNF inhibitor" includes, but is not limited to, solubilized TNF receptors, including, but not limited to, soluble tumor necrosis factor receptor type I (sTNFR-I; also called the p55 receptor), soluble tumor necrosis factor receptor type II (also called the p75 receptor), and Enbrel®; antibodies to TNF, including, but not limited to, Remicade™ and D2E7 (see, e.g., U.S. Pat. Nos. 6,090,382 and 6,258,562); antibodies to TNF receptor; sTNFR-I (see, e.g., WO 98/24463), etanercept (Enbrel®), Avakine™; inhibitors of TNF-α converting enzyme (TACE); and other molecules that affect TNF activity.

Exemplary TNF-α inhibitors are described, e.g., in European patent applications EP 308 378; EP 422 339; EP 393 438; EP 398 327; EP 412 486; EP 418 014, EP 417 563, EP 433 900; EP 464 533; EP 512 528; EP 526 905; EP 568 928; EP 607 776, which describes the use of leflunomide for inhibition of TNF-α; EP 663 210; EP 542 795; EP 818 439; EP 664 128; EP 542 795; EP 741 707; EP 874 819; EP 882 714; EP 880 970; EP 648 783; EP 731 791; EP 895 988; EP 550 376; EP 882 714; EP 853 083; EP 550 376; EP 943 616; EP 939 121; EP 614 984; EP 853 083; U.S. Pat. Nos. 5,136,021; 5,929,117; 5,948,638; 5,807,862; 5,695,953; 5,834,435; 5,817,822; 5,830,742; 5,834,435; 5,851,556; 5,853,977; 5,359,037; 5,512,544; 5,695,953; 5,811,261; 5,633,145; 5,863,926; 5,866,616; 5,641,673; 5,869,677; 5,869,511; 5,872,146; 5,854,003; 5,856,161; 5,877,222; 5,877,200; 5,877,151; 5,886,010; 5,869,660; 5,859,207; 5,891,883; 5,877,180; 5,955,480; 5,955,476; 5,955,435; 5,994,351; 5,990,119; 5,952,320; 5,962,481; International patent applications WO 90/13575, WO 91/03553, WO 92/01002, WO 92/13095, WO 92/16221, WO 93/07863, WO 93/21946, WO 93/19777, WO 95/34326, WO 96/28546, WO 98/27298, WO 98/30541, WO 96/38150, WO 96/38150, WO 97/18207, WO 97/15561, WO 97/12902, WO 96/25861, WO 96/12735, WO 96/11209, WO 98/39326, WO 98/39316, WO 98/38859, WO 98/39315, WO 98/42659, WO 98/39329, WO 98/43959, WO 98/45268, WO 98/47863, WO 96/33172, WO 96/20926, WO 97/37974, WO 97/37973, WO 97/47599, WO 96/35711, WO 98/51665, WO 98/43946, WO 95/04045, WO 98/56377, WO 97/12244, WO 99/00364, WO 99/00363, WO 98/57936, WO 99/01449, WO 99/01139, WO 98/56788, WO 98/56756, WO 98/53842, WO 98/52948, WO 98/52937, WO 99/02510, WO 97/43250, WO 99/06410, WO 99/06042, WO 99/09022, WO 99/08688, WO 99/07679, WO 99/09965, WO 99/07704, WO 99/06041, WO 99/37818, WO 99/37625, WO 97/11668, WO 99/50238, WO 99/47672, WO 99/48491; Japanese patent applications 10147531, 10231285, 10259140, and 10130149, 10316570, 11001481, and 127,800/1991; German application no. 19731521; and British application nos. 2 218 101, 2 326 881, 2 246 569. The disclosures of all of the aforementioned references are hereby incorporated by reference for any purpose.

EP 393 438 and EP 422 339 describe the amino acid and nucleic acid sequences of a soluble TNF receptor type I (also known as sTNFR-I or 30 kDa TNF inhibitor) and a soluble TNF receptor type II (also known as sTNFR-II or 40 kDa TNF inhibitor), which are collectively termed "sTNFRs". EP 393 438 and EP 422 339 also describe modified forms of sTNFR-I and sTNFR-II, including, but not limited to fragments, functional derivatives, and variants. Furthermore, EP 393 438 and EP 422 339 describe methods for isolating genes that code for the inhibitors, cloning the genes into suitable vectors, transforming or transfecting the genes into certain cell types, and expressing the genes to produce the inhibitors.

sTNFR-I and sTNFR-II are members of the nerve growth factor/TNF receptor superfamily of receptors, which includes the nerve growth factor receptor (NGF), the B cell antigen CD40, 4-1BB, the rat T-cell antigen MRC OX40, the fas antigen, and the CD27 and CD30 antigens (Smith et al. (1990) *Science*, 248:1019-1023). A conserved feature of that group of cell surface receptors is a cysteine-rich extracellular ligand binding domain, which can be divided into four repeated motifs of about forty amino acids that contain 4-6 cysteine residues at positions that are well conserved (Smith et al. (1990), supra).

EP 393 438 teaches a 40 kDa TNF inhibitor Δ51 and a 40 kDa TNF inhibitor Δ53, which are truncated versions of the full-length recombinant 40 kDa TNF inhibitor protein. Δ51 and Δ53 have 51 or 53 amino acids, respectively, deleted from the carboxyl terminus of the mature protein.

Published PCT Application No. WO 98/01555 describes truncated forms of sTNFR-I and sTNFR-II that do not contain the fourth domain (amino acid residues $Thr^{127}$-$Asn^{161}$ of sTNFR-I and amino acid residues $Pro^{141}$-$Thr^{179}$ of sTNFR-II); a portion of the third domain (amino acid residues $Asn^{111}$-$Cys^{126}$ of sTNFR-I and amino acid residues $Pro^{123}$-$Lys^{140}$ of sTNFR-II); and, optionally, do not contain a portion of the first domain (amino acid residues $Asp^1$-$Cys^{19}$ of sTNFR-I and amino acid residues $Leu^1$-$Cys^{32}$ of sTNFR-II). In certain embodiments, the truncated sTNFRs include the proteins represented by the formula $R_1$-$[Cys^{19}$-$Cys^{103}]$-$R_2$ and $R_4$-$[Cys^{32}$-$Cys^{115}]$-$R_5$. These proteins are truncated forms of sTNFR-I and sTNFR-II, respectively.

As used herein, "$R_1$-$[Cys^{19}$-$Cys^{113}]$-$R_2$" represents one or more proteins wherein $[Cys^{19}$-$Cys^{103}]$ is residues 19 through 103 of sTNFR-I, the sequence of which is provided in FIG. 1 of WO 98/01555; wherein $R_1$ represents a methionylated or nonmethionylated amine group of $Cys^{19}$ or one or more amino-terminal amino acid residues selected from $Cys^{18}$ to $Asp^1$; and wherein $R_2$ represents a carboxy group of $Cys^{103}$ or one or more carboxy-terminal amino acid residues selected from $Phe^{104}$ to $Leu^{110}$.

Exemplary truncated sTNFR-I's of the present invention include, but are not limited to, sTNFR-I 2.6D/C105, sTNFR-I 2.6D/C106, sTNFR-I 2.6D/N105, sTNFR-I 2.3D/d8, sTNFR-I 2.3D/d18, sTNFR-I 2.3D/d15, either methionylated or nonmethionylated, and variants and derivatives thereof. Certain exemplary truncated sTNFR-I's are described, e.g., in published PCT Application No. WO 98/01555.

Figure 8:
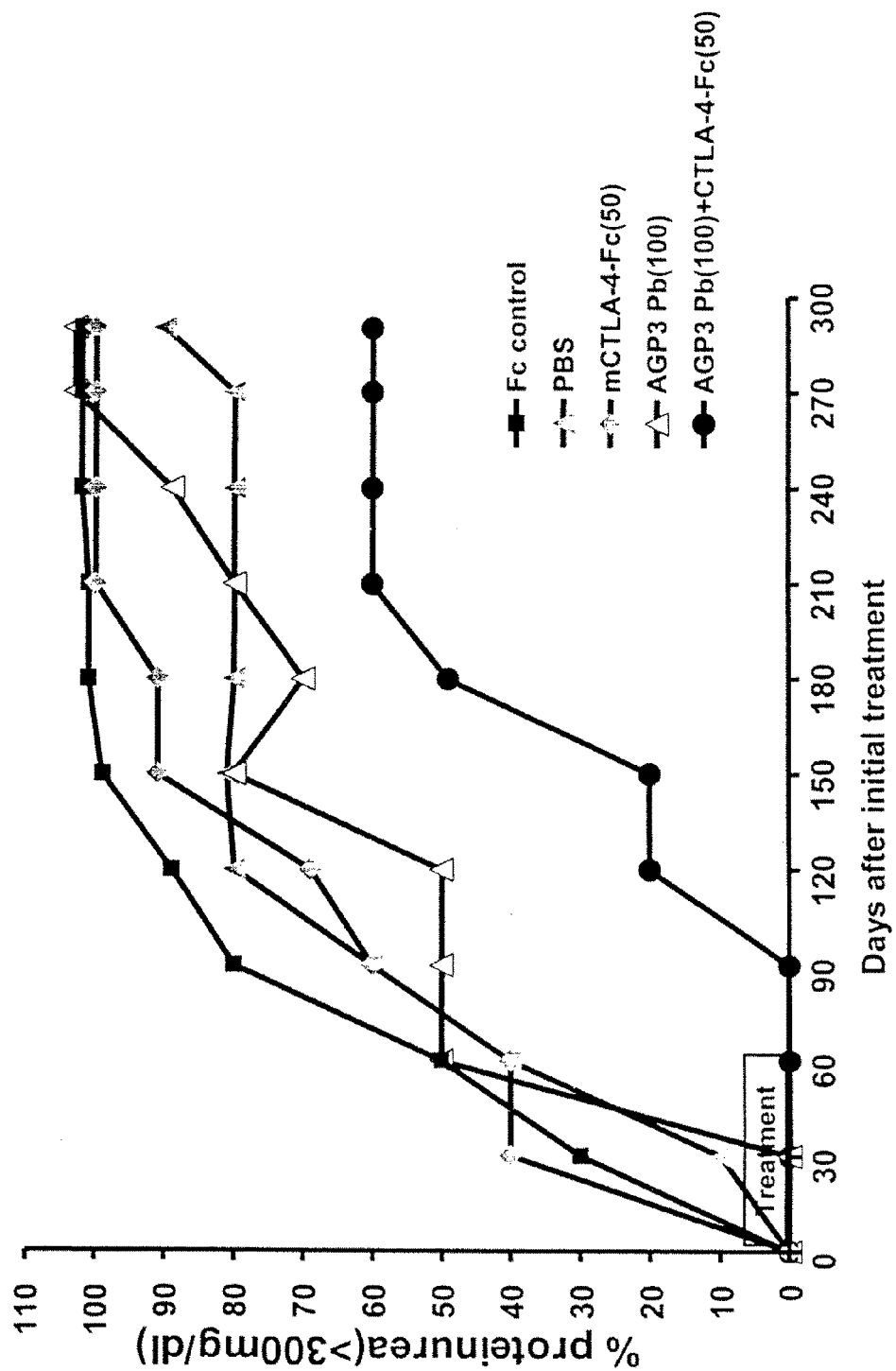
FIG. 8 shows the percent of mice in the treatment groups in FIG. 7 with levels of proteinuria exceeding 300 mg/dl. The lupus prone mice were tested for proteinuria every 30 days using Albustix® commercial assay (Bayer AG).

As used herein, "$R_3$-$[Cys^{32}$-$Cys^{115}]$-$R_4$" represents one or more proteins wherein $[Cys^{32}$-$Cys^{115}]$ is residues $Cys^{32}$ through $Cys^{115}$ of sTNFR-II, the sequence of which is provided in FIG. 8 of WO 98/01555; wherein $R_3$ represents a methionylated or nonmethionylated amine group of $Cys^{32}$ or one or more amino-terminal amino acid residues selected from $Cys^{31}$ to $Leu^1$; and wherein $R_4$ represents a carboxy group of $Cys^{115}$ or one or more carboxy-terminal amino acid residues selected from $Ala^{116}$ to $Arg^{122}$.

In certain embodiments, sTNFR-1 may be pegylated. Certain exemplary N-terminal pegylated forms of sTNFR-1 are described, e.g., in published PCT Application No. WO 98/01555.

Interferons (IFNs) were originally named for their ability to interfere with viral infection of host cells (Isaacs and Lindenman, 1957, *Proc. R. Soc.* 147:28-267). Since their discovery, a number of members of the interferon family have been identified with various biological roles in addition to antiviral defense, including cell growth and cell immunity. The members of the IFN family were originally classified into three groups from the cell or tissue of origin: leukocyte, fibroblast, and immune. Thereafter, these interferon species became known as IFN-α, IFN-β, and IFN-γ, respectively (Pestka et al., 1997, *Semin. Oncol.* 24(suppl 9):S9-4-S9-17). Additional IFN species have been discovered, and currently the interferons are divided into two classes based on common receptor types, type I IFN receptor or type II IFN receptor (Haque and Williams, 1998, *Semin. Oncol.* 25(suppl 1):14-22; Aguet et al., 1984, *Virology* 132:211-216; Merlin et al., 1985, *J. Gen. Virol.* 66:1149-1152). Interferon types IFN-α, IFN-β, and IFN-ω, and IFN-τ bind the type I IFN receptor, while IFN-γ binds the type II IFN receptor (Pfeffer et al., 1998, *Cancer Res.* 58:2489-2499). The type I IFNs are produced by virtually every cell type and can be induced upon exposure to viruses, double-stranded RNA, polypeptides, and cytokines (Jonasch and Haluska, 2001, *The Oncologist* 6:34-55). Type II IFN-γ is primarily produced in T lymphocytes and natural killer (NK) cells and can be induced by a number of immunological stimuli (Id.).

IFN-γ signaling depends on at least five distinct proteins: IFNGR1 and IFNGR2 (subunits of the IFN-γ receptor), Jak1, Jak2 and the transcription factor STAT1 (Schindler and Darnell, 1995, *Annu. Rev. Biochem.* 64:621-651; Bach et al., 1997, *Annu. Rev. Immunol.* 15:563-591). IFN-γ receptors are found on most cell types, except mature erythrocytes (Farrar and Schreiber, 1993, *Annu. Rev. Immunol.* 11:571-611). Jak1, Jak2, and STAT1 proteins mediate IFN-γ signaling.

IFN-γ regulates a variety of biological functions, such as antiviral responses, cell growth, and tumor suppression. Antiviral activity appears to affect all phases of viral infection, including entry, uncoating, transcription, RNA stability, translation, maturation, and assembly and release (Id.). IFN-γ regulates cell growth by inducing or inhibiting apoptosis, depending on the cell type. For example, IFN-γ induces apoptosis of murine pre-B cells but inhibits apoptosis of B chronic lymphocytic leukemia cells (Grawunder et al., 1993, *Eur. J. Immunol.* 23:544-551; Rojas et al., 1996, *Leukemia* 10:1782-1788; Buschle et al., 1993, *J. Exp. Med.* 177:213-218). Depending on growth and other conditions, IFN-γ also promotes either cell proliferation or apoptosis in malignant human T cells (Novelli et al., 1994, *J. Immunol.* 152:496-504).

A large and increasing body of literature supports the hypothesis that increased IFN-γ or its effector molecules contribute to pathology seen in human autoimmune disorders. For example, there is evidence that IFN-γ, or molecules whose expression is up-regulated by IFN-γ such as IP-10, HLA DQ, and neopterin are present at increased levels in systemic lupus erythematosus (SLE) patients, particularly those with lupus nephritis (Funauchi et al., 1991, *Tohoku J. Exp. Med.* 164:259-267; Yokoyama et al., 1992, *Kidney Int.* 42:755-763; Al-Janadi et al., 1993, *J. Clin. Immunology* 13:58-67; Narumi et al., 2000, *Cytokine* 12:1561-1565; Lim et al., 1993, *Ann. Rheum. Dis.* 52:429-435; Samsonov et al., 1995, *Lupus* 4:29-32). Further evidence comes from a histological analysis of tissues from lupus nephritis patients, in which a high Th1:Th2 ratio was detected in the peripheral blood, and greatly increased number of macrophages and IFN-γ-like immunoreactivity in renal biopsies from WHO Class IV patients as compared to healthy controls (Masutani et al., 2001, *Arthritis and Rheumatism* 44:2097-2106). Another link comes from the identification of polymorphisms in the IFN-γ receptor that are associated with a higher incidence of SLE (Nakashimi et al., 1999, *FEBS Letters* 453:187-190).

Several different animal models of lupus nephritis have been tested with reagents that block IFN-γ. A comprehensive description of these animal models can be found in Theofilopoulos and Dixon (1985, *Advances in Immunology* 37:269-). Two strains/models of mice considered relevant to human lupus nephritis have both shown beneficial effects of IFN-γ blockade. These two models are the NZB/NZW F1 (BWF1) mouse strain and the MRL-Fas$^{lpr}$ mouse strain. Both strains of mice spontaneously develop disease and a recent report has identified an interferon-inducible gene as a candidate gene involved in predisposition to disease in the NZB strain of mice (Rozzo et al., 2001, *Immunity* 15:435-43). In both mouse strains, IFN-γ modulation/blockade has been performed with a variety of reagents including antibodies to IFN-γ soluble receptor for IFN-γ (both protein and DNA constructs), and gene knockouts. Positive effects have been repeatedly documented as measured by auto-antibody production, proteinuria, histology, and survival (Theophilopoulos et al., 2001, *Arthritis Res.* 3:136-).

IFN-γ activity is essential for proper regulation of the immune response. However, increased IFN-γ activity can result in a pathological condition, such as inflammatory, infectious, and autoimmune disorders and diseases. Inhibition of excessive IFN-γ activity is a promising strategy for treating patients with IFN-γ mediated diseases.

IL-18 is a pro-inflammatory cytokine that was found to induce interferon-γ and was previously named interferon gamma inducing factor (IGIF). In certain instances, IL-1 has been shown to upregulate IL-18 production, and IL-18 induces production of a number of proinflammatory cytokines, including IL-6 and MMP-1. See, e.g., Dinarello et al. (1998), *J. Leukocyte Biol.* 63:658-64. In certain instances, caspase I is also important for IL-18 production. Experiments also suggest that TNF-α regulates IL-18 production, and that simultaneous inhibition of TNF-α and IL-18 protects against liver toxicity. See, e.g., Faggioni et al. (2000), *PNAS* 97: 2367-72.

IL-18 acts in vivo through a receptor system reminiscent of the IL-1 system. IL-18 interacts with a cell surface receptor (IL-18R), which interacts with an accessory protein (IL-18RAcP). IL-18-mediated signaling proceeds upon formation of the complex of IL-18, IL-18R, and IL-18RAcP. A natural inhibitor for IL-18 is IL-18 bp. In certain embodiments, IL-18 bp acts as a "decoy receptor" by binding to IL-18 molecules and preventing interaction with IL-18R.

In certain embodiments, the present invention is directed to therapies comprising at least one IL-18 inhibitor and a B7 inhibitor, a CD28 inhibitor, or both, and methods of treatment using such therapies. In certain embodiments, a therapy comprises an IL-18 inhibitor and at least one additional molecule described herein. Exemplary conditions that may be treated according to certain embodiments include, but are not limited to, inflammation, autoimmune diseases, IL-1 mediated diseases, and TNF-mediated diseases. Exemplary conditions that may be treated with at least one IL-18 inhibitor and at least one molecule described herein according to certain embodiments include, but are not limited to, arthritis, including, but not limited to rheumatoid arthritis; systemic lupus erythematosus (SLE); graft versus host disease (GvHD); hepatitis; sepsis; and the loss of bone and cartilage accompanying these diseases.

Exemplary IL-18 inhibitors include, but are not limited to, antibodies that bind to IL-18; antibodies that bind to IL-18R; antibodies that bind to IL-18RAcP; IL-18 bp; IL-18R fragments (e.g., a solubilized extracellular domain of the IL-18 receptor); peptides that bind to IL-18 and reduce or prevent its interaction with IL-18R; peptides that bind to IL-18R and reduce or prevent its interaction with IL-18 or with IL-18RAcP; peptides that bind to IL-18RAcP and reduce or prevent its interaction with IL-18R; and small molecules that reduce or prevent IL-18 production or the interaction between any of IL-18, IL-18R, and IL-18RAcP.

Certain IL-18 inhibitors are described, e.g., in U.S. Pat. No. 5,912,324, issued Jul. 14, 1994; EP 0 962 531, published Dec. 8, 1999; EP 712 931, published Nov. 15, 1994; U.S. Pat. No. 5,914,253, issued Jul. 14, 1994; WO 97/24441, published Jul. 10, 1997; U.S. Pat. No. 6,060,283, issued May 9, 2000; EP 850 952, published Dec. 26, 1996; EP 864 585, published Sep. 16, 1998; WO 98/41232, published Sep. 24, 1998; U.S. Pat. No. 6,054,487, issued Apr. 25, 2000, WO 99/09063, published Aug. 14, 1997; WO 99/22760, published Nov. 3, 1997; WO 99/37772, published Jan. 23, 1998; WO 99/37773, published Mar. 20, 1998; EP 0 974 600, published Jan. 26, 2000; WO 00/12555, published Mar. 9, 2000; Japanese patent application JP 111,399/94, published Oct. 31, 1997; Israel patent application IL 121554 A0, published Feb. 8, 1998; which are incorporated herein by reference for any purpose.

B7 is a receptor that mediates costimulation of T cells. B7 binds to two separate ligands, CD28 and CTLA4. Interaction of B7 and CD28 activates T cells. CTLA4 is a negative regulator of this activation. There are at least two B7 receptors, termed B7.1 and B7.2.

As used herein, the term "B7" refers to B7.1, B7.2, or both B7.1 and B7.2.

In certain embodiments, soluble B7 molecules may be used to modulate costimulatory pathways. In certain embodiments, soluble CTLA4 molecules may be used to modulate costimulatory pathways. Certain modulators of B cell-T cell costimulatory pathways include, but are not limited to, inhibitors of CD28, B7.1, and B7.2. Certain examples include, but are not limited to, soluble forms of B7.1 or B7.2 and CTLA4.

The B7.1 sequence and certain B7.1 derived inhibitors of B cell-T cell costimulatory pathways are described in Freeman et al. *J. Immunol.* 143, 2714-2722 (1989).

The B7.2 sequence and certain B7.2 derived inhibitors of B cell-T cell costimulatory pathways are described in U.S. Pat. No. 5,942,607.

B7 receptors are also described in WO 92/00092 and WO 98/58965.

The CD28 sequence is disclosed in Aruffo et al., *Proc. Natl. Acad. Sci. USA* 84, 8573-8579 (1987). CD28 molecules are also disclosed in WO 90/05541, WO 93/19767, WO 94/28912 and EP 0 445 228.

There has been an extensive body of literature relating to the B cell/T cell costimulatory pathway involving CD28 interaction with B7.1 (CD80) and B7.2 (CD86) and the regulation of this interaction by CTLA4. B7.1 and B7.2 are expressed on the surface of activated B lymphocytes (Linsley et al. J. Exp. Med. 173, 721-730 (1991); Freeman et al. Science 262, 909-911 (1993)) Both B7.1 and B7.2 are receptors for two ligands, CD28 and CTLA4, expressed on T lymphocytes. CD28 is constitutively expressed on resting T cells and increases after activation whereas CTLA4 is not expressed on resting T cells but appears after activation (Brunet et al. Nature 328, 267-270 (1987)). The interaction of CD28 with B7.1 and B7.2 provides a stimulatory signal for T cell activation whereas CTLA4 binding to B7.1 and B7.2 attenuates the response. CTLA4-Ig fusion proteins have been constructed and used to study the effects of CTLA4 binding to B7.1 and B7.2 (see for example WO93/00431 and WO97/28267). The B7:CD28/CTLA4 costimulatory pathway has been implicated in T cell mediated immune responses and manipulation of the pathway is useful in the prevention and treatment of a variety of disorders, including rheumatoid arthritis, graft versus host disease, graft rejection, lupus, multiple sclerosis, psoriasis and others, such as IL-1 and TNF-alpha mediated disorders mentioned herein.

Immune responses mediated by B cell/T cell costimulatory pathway may be modulated by inhibitors of the CD28/B7 pathway. As mentioned above, one such inhibitor is CTLA4. In certain embodiments, CTLA4 is fused to a human immunoglobulin region either directly or through one or more linker moieties. In certain embodiments, CTLA4 comprises an extracellular domain of CTLA4 which binds B7.1 and/or B7.2 and partially or completely inhibits immune responses mediated by the CD28/B7 pathway. In certain embodiments, a CTLA4 extracellular domain comprises about amino acid residues 1 (methionine) to 124 (aspartic acid) as shown in SEQ ID NO. 2. Other exemplary CTLA4 polypeptides include, but are not limited to, fragments which encompass at least a portion of a CTLA4 extracellular domain, which fragments bind B7.1 and/or B7.2 and partially or completely inhibit immune responses mediated by the CD28/B7 pathway. In certain embodiments, a CTLA4 extracellular domain may be fused to a human immunoglobulin region either directly or through one or more linker moieties.

In certain embodiments, CTLA4 polypeptides include variants having a substitution, deletion or insertion of one or more amino acids in the sequence shown in SEQ ID NO. 2. As nonlimiting examples, a CTLA4 variant may have a substitution of a different amino acid for serine at position 25, alanine at position 29, threonine at position 30, leucine at position 104 and/or glycine at position 105. Certain nonlimiting CTLA4 variants are as described in WO02/02638. In certain embodiments, a CLTA4 variant has a tyrosine substituted for an alanine at position 29 and a glutamic acid substituted for a leucine at position 104 of the sequences shown in SEQ ID NO. 2. In certain embodiments, the above-mentioned CTLA4 variants are in the extracellular domain of about residues 1-124 fused to a human immunoglobulin region.

Exemplary B7 and CD28 inhibitors include, but are not limited to, CTLA4, CTLA4-Fc, soluble forms of B7.1, soluble forms of B7.2, an antagonist CD28 antibody, and an antagonist B7 antibody.

In certain embodiments, therapies comprise at least one of ICOS and B7RP1. Certain examples include, but are not limited to, soluble forms of ICOS. B7RP1 and ICOS sequences are disclosed in PCT published Application No. WO 00/46240.

In certain embodiments, therapies comprise at least one of CD40 and CD40L. Certain examples include, but are not limited to, soluble forms of CD40. The CD40L sequence is disclosed in WO 93/08207 and U.S. Pat. No. 5,981,724. The CD40 sequence is disclosed in Stamenkovic et al. *EMBO J.* 8, 1403 (1989). CD40 Abs (including antagonist Abs) are disclosed in WO 95/09653. CD40 ligand Abs (including antagonist Abs) are disclosed in WO 96/40918.

In certain embodiments, therapies comprise at least one of CD30 and CD30L. The sequence of human CD30 is disclosed in Durkop et al. *Cell* 68, 421 (1992). The sequence of human CD30 ligand is disclosed in WO93/24135.

In certain embodiments, therapies comprise at least one of CD27 and CD27L. The sequence of human CD27 is disclosed in Camerini et al. *J. Immunol.* 147, 3165 (1991). The sequence of human CD27 ligand is disclosed in WO94/05691.

In certain embodiments, therapies comprise at least one of OX40 and OX40L. Certain examples include soluble forms of OX40. The sequence of human OX40 ligand is disclosed in Miura et al. *Mol Cell Biol.* 11, 1313 (1991).

In certain embodiments, therapies comprise at least one of 4-1-BB and 4-1-BB ligand. Certain examples include soluble forms of 4-1-BB. The structures of 4-1-BB and 4-1-BB ligand and certain inhibitors thereof, are disclosed in WO 94/26290 and U.S. Pat. Nos. 5,674,704 and 6,355,779.

In certain embodiments, therapies comprise at least one of TACI, BAFFR and AGP3. Certain examples include, but are not limited to, soluble forms of TACI, BAFFR, AGP3 peptibody (an AGP3 tandem dimer peptide-Fc fusion), and anti- BlyS antibody. AGP3 peptibody is disclosed in WO 02/92620. Information on AGP3, TACI and BAFFR is available in WO 01/87977. The sequence of human TACI is disclosed in WO98/39361. The ligand for TACI and methods for screening for inhibitors of the interaction of TACI with its ligand are disclosed in WO 00/67034. AGP-3, TACI, and BAFFR, and inhibitors thereof are described, e.g., in WO 00/47740, WO 01/85782, WO 02/115273, WO 98/39361, and von Bulow and Bram (1997) *Science* 278:138-140.

Exemplary TACI, BAFFR, and AGP3 inhibitors include, but are not limited to, soluble forms of TACI, soluble forms of BAFFR, AGP3 peptibody, anti-BlyS antibody, TACI-Fc, anti-BLIS antibody, BCMA-Fc, and BAFFR-Fc.

In certain embodiments, therapies comprise at least one of PD-1 and PD-1L. PD-1 is described in WO 93/08207. PD-1L is described in WO 01/39722.

In certain embodiments, therapies comprise an anti-CD20 antibody.

In certain embodiments, therapies comprise any of one or more slow-acting antirheumatic drugs (SAARDs) or disease modifying antirheumatic drugs (DMARDS), prodrug esters or pharmaceutically acceptable salts thereof for the treatment of an inflammatory or autoimmune condition, as defined above, including, but not limited to, acute and chronic inflammation such as rheumatic diseases (e.g., lyme disease, juvenile (rheumatoid) arthritis, osteoarthritis, psoriatic arthritis, rheumatoid arthritis and staphylococcal-induced ("septic") arthritis); and multiple sclerosis. Exemplary, SAARDs or DMARDS, prodrug esters and pharmaceutically acceptable salts thereof include, but are not limited to, allocupreide sodium, auranofin, aurothioglucose, aurothioglycanide, azathioprine, brequinar sodium, bucillamine, calcium 3-aurothio-2-propanol-1-sulfonate, chlorambucil, chloroquine, clobuzarit, cuproxoline, cyclophosphamide, cyclosporin, dapsone, 15-deoxyspergualin, diacerein, glucosamine, gold salts (e.g., cycloquine gold salt, gold sodium thiomalate, gold sodium thiosulfate), hydroxychloroquine, hydroxyurea, kebuzone, levamisole, lobenzarit, melittin, 6-mercaptopurine, methotrexate, mizoribine, mycophenolate mofetil, myoral, nitrogen mustard, D-penicillamine, pyridinol imidazoles such as SKNF86002 and SB203580, rapamycin, thiols, thymopoietin, and vincristine. In certain embodiments, structurally related SAARDs or DMARDs having similar analgesic and anti-inflammatory properties are also intended to be encompassed by this group.

Methotrexate is an anti-metabolite and immunosuppressive drug. In certain embodiments, methotrexate is an effective anti-inflammatory agent with utility in the treatment of severe and disabling psoriasis and rheumatoid arthritis (Hoffmeister (1983), *The American Journal of Medicine*, 30:69-73 and Jaffe (1988), *Arthritis and Rheumatism*, 31:299). Methotrexate is N-[4-[(2,4-diamino-6-pteridinyl) methylamino]benzoyl]-L-glutamic acid and has the structural formula:

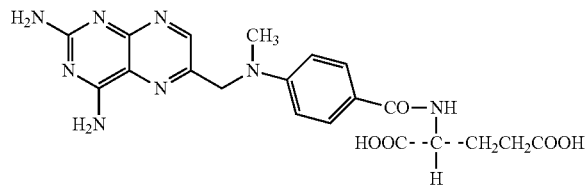

The following references describe: preparation of methotrexate (Seeger et al. (1949), *J. Am. Chem. Soc.*, 71:1753; metabolism of methotrexate (Freeman (1958), *J. Pharmacol. Exp. Ther*, 122:154 and Henderson et al. (1965), *Cancer Res.*, 25:1008); toxicity of methotrexate (Condit et al. (1960), *Cancer*, 13:222-249; pharmacokinetic models of methotrexate (Bischoff et al. (1970), *J. Pharm, Sci.*, 59:149); metabolism and pharmacokinetics of methotrexate (Evans (1980), *Appl. Pharmacokinet.*, Williams et al. (eds.), pp. 518-548 (Appl. Ther., Inc.); clinical pharmacology of methotrexate (Bertino (1981), *Cancer Chemother.*, 3.359-375 and Jolivet et al. (1983), *N. Eng. J. Med.*, 309:1094-1104); and clinical experience of methotrexate in rheumatoid arthritis (Weinblatt et al. (1985), *N. Eng. J. Med.*, 312:818-822; Furst (1985), *J. Rheumatol.*, 12(12):1-14; Williams et al. (1985), *Arthritis Rheum.*, 28:721-730 and Seitz et al. (1995), *British Journal of Rheumatology*, 34:602-609). Additionally, numerous patents have been issued disclosing active agent methotrexate and methods for synthesizing methotrexate or potential intermediates in the synthesis of methotrexate: U.S. Pat. Nos. 2,512, 572, 3,892,801, 3,989,703, 4,057,548, 4,067,867, 4,079,056, 4,080,325, 4,136,101, 4,224,446, 4,306,064, 4,374,987, 4,421,913 and 4,767,859.

Various activities of methotrexate have been demonstrated which likely contribute to its efficacy (Segal et al. (1990), *Seminars in Arthritis and Rheumatism*, 20:190-198). The following mechanisms of action for methotrexate have been postulated: inhibition of folate-dependent pathways and protein metabolism (Morgan et al. (1987), *Arthritis and Rheumatism*, 30:1348-1356); inhibition of neutrophil migration into arthritic joints (Van de Kerkhof et al. (1985), *British Journal of Dermatology*, 113:251-255; Ternowitz et al. (1987), *Journal of Investigative Dermatology*, 89:192-196 and Sperling (1992), *Arthritis and Rheumatism*, 35:376-384); IL-6 inhibitory activity (Segal (1991), *Arthritis and Rheumatism*, 34(2):146-152) and the local specific anti-proliferative effect on cells involved in arthritis (Rodenhuis et al., (1987), *Arthritis and Rheumatism*, 30:369-374). Methotrexate has been shown to block the interleukin-1 beta/interleukin-1 receptor pathway (Brody et al. (1993), *European Journal of Clinical Chemistry and Clinical Biochemistry*, 31(10):667-674); however, although methotrexate may inhibit the proliferative effects of IL-1 and decrease monocyte IL-1 production in the short term in certain patients, this effect is not sustained and is unlikely to explain the long-term efficacy of methotrexate (Barrera et al. (1996), *Seminars in Arthritis and Rheumatism*, 25(4:234-253).

In certain embodiments, methotrexate is administered in combination with one or more compounds, including, but not limited to, an IL-1 inhibitor, a TNF inhibitor, an IFN-γ inhibitor, an IL-18 inhibitor, an inhibitor of the B7/CD28 pathway, an inhibitor of the ICOS/B7RP1 pathway, an inhibitor of the CD40 pathway, an inhibitor of the CD30 pathway, an inhibitor of the CD27 pathway, an inhibitor of the OX40 pathway, an inhibitor of the 4-1-BB pathway, an inhibitor of the TACI, BAFFR, AGP3 pathway, an inhibitor of the PD-1 pathway, an inhibitor of the CD20 pathway, and other compounds that may be used to treat inflammation or an autoimmune condition.

In certain embodiments, methotrexate is administered orally, intraperitoneally, subcutaneously, or intravenously. For example, in certain embodiments, a human patient may be treated with a combination of methotrexate and CTLA4-Fc or other B7/CD28 pathway inhibitor. In certain embodiments, the patient takes a tablet or capsule of methotrexate three times a week, at a total weekly dose of 5 to 50 mg/week. In certain such embodiments, the patient is injected intravenously with CTLA4-Fc at a daily dose between 0.1 mg/kg and 100 mg/kg. In certain embodiments, the starting doses of the particular compounds used are reduced for a patient who exhibits an adverse reaction. In certain embodiments, one or more of the drugs used in the combination can be changed or reduced, e.g., depending on the different formulations, routes, dose schedules, or other variables known to those skilled in the art, including, but not limited to, the individual patient's tolerance of the drug, its efficacy, and toxicity.

In certain embodiments, the patient is treated with a weekly starting dose of methotrexate at between 5 mg and 7.5 mg (orally or intramuscularly), and a daily dose of CTLA4-Fc at between 0.1 mg/kg and 100 mg/kg intravenously. In certain embodiments, the dosage of methotrexate is increased by 5 mg every 2 to 3 weeks. In certain embodiments, the maximum dosage level is determined at a point at which the patient shows improvements, which is generally less than about 25 mg of methotrexate per week, and, in certain embodiments, between 5 to 25 mg of methotrexate per week. In certain embodiments, at the end of the five-day period the patient is evaluated. In certain embodiments, the evaluation includes physical examination and extensive laboratory testing. In certain embodiments, the tests include evaluation for toxicity. In certain embodiments, additional laboratory monitoring in the case of methotrexate includes a complete blood cell count every 2 weeks for the first 3 months and then monthly thereafter. In certain embodiments, additional precautions include monthly assessments of levels of serum albumin, alanine amino transferase, bilirubin, creatinine, and blood urea nitrogen. In certain embodiments, monthly urinalysis is performed.

In certain embodiments, methods of treating inflammatory and/or autoimmune diseases are provided. In certain embodiments, pharmaceutical compositions are provided.

In certain embodiments, the co-stimulatory factors may be used in conjunction with cytokine inhibitors. Certain exemplary cytokine inhibitors of interest include, but are not limited to, IL-1 inhibitors and TNF-α inhibitors. In certain embodiments, methods are provided for treating an IL-1 mediated disease, which comprises administering a therapeutically effective amount of an IL-1 inhibitor and an inhibitor of T cell or B cell activation. In certain embodiments, methods are provided for treating a TNF-α mediated disease, which comprises administering a therapeutically effective amount of a TNF-α inhibitor and an inhibitor of T cell or B cell activation. In certain embodiments, methods are provided for treating an inflammatory or an autoimmune condition, which comprises administering a therapeutically effective amount of an IL-1 inhibitor, a therapeutically effective amount of a TNF-α inhibitor, and an inhibitor of T cell or B cell activation.

Rheumatoid arthritis (RA) is a disease of unknown etiology that involves several components of the inflammatory process. Clinical and experimental studies have shown that immune cells (T and B) along with proinflammatory cytokines create an imbalance in the biological system to cause local inflammation in the joints. Inhibition of IL-1 (by IL-1 Ra or Kineret™) or TNF-α (by soluble TNFR1, TNFR2 or anti-TNF-α antibody) has been shown to be beneficial in experimental models of arthritis and in RA patients. Clinical and experimental studies have also demonstrated the presence of T cells and B cells at the affected tissue. Inhibitors of T cells and B cells, such as CTLA-4-Ig, have shown efficacy in experimental animal models when used from the induction of arthritis. Studies have shown that CTLA-4-Ig is not efficacious in experimental animal models (Collagen-induced arthritis), when treatment starts from the clinical evidence of inflammatory arthritis. A role for combination therapy that modulates T cell or B cell function with anti-proinflammatory cytokine medication in a model of experimental arthritis is discussed in Examples 1 to 3. As in Rheumatoid Arthritis, T cells, B cells and proinflammatory cytokines are involved in collagen-induced arthritis in mice.

In certain embodiments of the invention, one may treat any one or more of the following conditions: infections such as bacterial, fungal, protozoan and viral infections, especially HIV-1 or HIV-2; diarrhorea; psoriasis; inflammation; allergies; atopic dermatitis; respiratory allergic diseases such as asthma, allergic rhinitis, hypersensitivity lung disease, hypersensitivity pneumonitis, eosinophilic pneumonia (e.g. Loeffler's syndrome, chronic eosinophilic pneumonia, interstitial lung disease (ILD), such as idiopathic pulmonary fibrosis or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses; drug allergy; insect sting allergy; inflammatory bowel disease, such as Crohn's disease and ulcerative colitis; spondyloarthropathy; scleroderma; psoriasis; inflammatory dermatosis such as dermatitis, eczema, atopic dermatitis, allergic contact dermatitis, urticaria, vasculitis (e.g. necrotizing, cutaneous and hypersensitivity vasculitis), eosinphilic myositis and eosinophilic fasciitis; autoimmune diseases such as rheumatoid arthritis, psoriatic arthritis, multiple sclerosis, systemic lupus erythematosus, myasthenia gravis, juvenile onset diabetes, glomerulonephritis, autoimmune thyroiditis and Behcet's disease; graft rejection, including allograft rejection or graft-versus-host disease; cancers with leukocyte infiltration of the skin or organs; reperfusion injury; atherosclerosis; certain haematologic malignancies; shock, including septic shock and endotoxic shock.

In certain embodiments, gene therapy may be employed. In certain embodiments, a gene (either genomic DNA, cDNA, and/or synthetic DNA) encoding a specific binding partner of a target molecule, or a fragment, variant, or derivative thereof, may be operably linked to a constitutive or inducible promoter to form a "gene therapy DNA construct". In certain embodiments, the promoter may be homologous or heterologous to the gene encoding the specific binding partner, provided that it is active in the cell or tissue type into which the construct will be inserted. Other components of a gene therapy DNA construct may include, but are not limited to, DNA molecules designed for site-specific integration (e.g., endogenous flanking sequences useful for homologous recombination), tissue-specific promoter, enhancer(s) or silencer(s), DNA molecules capable of providing a selective advantage over the parent cell, DNA molecules useful as labels to identify transformed cells, negative selection systems, cell specific binding agents (as, for example, for cell targeting) cell-specific internalization factors, and transcription factors to enhance expression by a vector as well as factors to enable vector manufacture.

In certain embodiments, a gene therapy DNA construct may then be introduced into a patient's cells (either ex vivo or in vivo). In certain embodiments, the gene therapy DNA construct may be introduced via viral vectors. Exemplary viral vectors used for delivery of gene therapy DNA constructs include, but are not limited to, adenovirus, adeno-associated virus, herpes simplex virus, lentivirus, papilloma virus, and retrovirus vectors. In certain embodiments, some of these vectors, such as retroviral vectors, will deliver the gene therapy DNA construct to the chromosomal DNA of the patient's cells, and the gene therapy DNA construct can integrate into the chromosomal DNA. In certain embodiments, other vectors will function as episomes and the gene therapy DNA construct will remain in the cytoplasm. The use of gene therapy vectors is described, for example, in U.S. Pat. Nos. 5,672,344, 5,399,346.

Exemplary methods to deliver gene therapy DNA constructs to a patient's cells without the use of viral vectors, include, but are not limited to, liposome-mediated transfer, direct injection of naked DNA, receptor-mediated transfer (ligand-DNA complex), electroporation, calcium phosphate precipitation, and microparticle bombardment (e.g., "gene gun"). See U.S. Pat. Nos. 4,970,154, WO 96/40958, 5,679,559, 5,676,954, and 5,593,875.

In certain embodiments, the levels of expression of a specific binding partner in a cell may be increased via gene therapy by insertion of one or more enhancer elements into the promoter. In certain embodiments, the enhancer elements used may be selected based on the tissue in which one desires to activate the genes, and enhancer elements known to confer promoter activation in that tissue will be selected. In certain embodiments, the lck promoter enhancer element may be used to increase expression of a specific binding partner to be expressed in T-cells. In certain embodiments, the functional portion of the transcriptional element to be added may be inserted into a fragment of DNA containing a promoter for a specific binding partner using standard cloning techniques. This construct, known as a "homologous recombination construct" can then be introduced into the desired cells either ex vivo or in vivo.

In certain embodiments, gene therapy may be used to decrease expression of target molecules by modifying the nucleotide sequence of the endogenous promoter(s). In certain embodiments, the modification may be accomplished via homologous recombination methods. In certain embodiments, a DNA molecule containing all or a portion of the promoter of a gene encoding a target molecule may be engineered to remove and/or replace pieces of the promoter that regulate transcription. In certain embodiments, the TATA box and/or the binding site of a transcriptional activator of the promoter may be deleted using standard molecular biology techniques; such deletion can inhibit promoter activity thereby repressing transcription of the corresponding target molecule gene. In certain embodiments, deletion of the TATA box or transcription activator binding site in a promoter may be accomplished by generating a DNA construct comprising all or the relevant portion of a promoter in which one or more of the TATA box or transcriptional activator binding site nucleotides are mutated via substitution, deletion and/or insertion of one or more nucleotides such that the TATA box or activator binding site has decreased activity or is rendered completely inactive. In certain embodiments, this construct may contain at least about 500 bases of DNA that correspond to the native (endogenous) 5' and 3' flanking regions of the promoter segment that has been modified, and may be introduced into the appropriate cells (either ex vivo or in vivo) either directly or via a viral vector as described above. In certain embodiments, integration of the construct into the genomic DNA of the cells may be via homologous recombination, where the 5' and 3' flanking DNA sequences in the promoter construct can serve to help integrate the modified promoter region via hybridization to the endogenous chromosomal DNA.

In certain embodiments, other gene therapy methods may also be employed where it is desirable to inhibit one or more target molecules. In certain embodiments, antisense DNA or RNA molecules, which have a sequence that is complementary to at least a portion of a selected target molecule gene may be introduced into the cell. In certain embodiments, each such antisense molecule will be complementary to the start site (5' end) of each selected target molecule gene. When the antisense molecule then hybridizes to the corresponding mRNA encoding a target molecule, translation of this mRNA is prevented In certain embodiments, gene therapy may be employed to create a dominant-negative inhibitor of one or more target molecules. In certain embodiments, the DNA encoding a mutant full length or truncated polypeptide of each selected target molecule can be prepared and introduced into the cells of a patient using either viral or non-viral methods as described above. In certain embodiments, each mutant may be designed to compete with an endogenous target molecule in its biological role.

In certain embodiments, the invention provides for pharmaceutical compositions comprising a therapeutically effective amount of certain particular molecules together with a pharmaceutically acceptable diluent, carrier, solubilizer, emulsifier, preservative and/or adjuvant.

In certain embodiments, the invention provides for pharmaceutical compositions comprising certain particular molecules, together with a pharmaceutically acceptable diluent, carrier, solubilizer, emulsifier, preservative and/or adjuvant.

In certain embodiments, acceptable formulation materials preferably are nontoxic to recipients at the dosages and concentrations employed.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (*Remington's Pharmaceutical Sciences*, 18$^{th}$ Edition, A. R. Gennaro, ed., Mack Publishing Company (1990).

In certain embodiments, one or more of the molecules are linked to a half-life extending vehicle known in the art. Such vehicles include, but are not limited to, the Fc domain, polyethylene glycol, and dextran. Such vehicles are described, e.g., in published PCT Application No. WO 00/24782, which is hereby incorporated by reference for any purpose.

In certain embodiments, the optimal pharmaceutical composition will be determined by one skilled in the art depending upon, for example, the intended route of administration, delivery format and desired dosage. See, for example, *Remington's Pharmaceutical Sciences*, supra. In certain embodiments, such compositions may influence the physical state, stability, rate of in vivo release and rate of in vivo clearance of the antibodies of the invention.

In certain embodiments, the primary vehicle or carrier in a pharmaceutical composition may be either aqueous or non-aqueous in nature. For example, in certain embodiments, a suitable vehicle or carrier may be water for injection, physiological saline solution or artificial cerebrospinal fluid, possibly supplemented with other materials common in compositions for parenteral administration. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which may further include sorbitol or a suitable substitute therefor. In certain embodiments, a composition comprising certain particular molecules may be prepared for storage by mixing the selected composition having the desired degree of purity with optional formulation agents (*Remington's Pharmaceutical Sciences*, supra) in the form of a lyophilized cake or an aqueous solution. Further, in certain embodiments, a composition comprising certain particular molecules may be formulated as a lyophilizate using appropriate excipients such as sucrose.

In certain embodiments, the pharmaceutical compositions of the invention can be selected for parenteral delivery. In certain embodiments, the compositions may be selected for inhalation or for delivery through the digestive tract, such as orally. The preparation of such pharmaceutically acceptable compositions is within the skill of the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition may be in the form of a pyrogen-free, parenterally acceptable aqueous solution comprising the desired certain particular molecules in a pharmaceutically acceptable vehicle. In certain embodiments, a vehicle for parenteral injection is sterile distilled water in which certain particular molecules are formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide for the controlled or sustained release of the product which may then be delivered via a depot injection. In certain embodiments, hyaluronic acid may also be used, and may have the effect of promoting sustained duration in the circulation. In certain embodiments, implantable drug delivery devices may be used to introduce the desired molecule.

In certain embodiments, a pharmaceutical composition may be formulated for inhalation. In certain embodiments, certain particular molecules may be formulated as a dry powder for inhalation. In certain embodiments, an inhalation solution comprising certain particular molecules may be formulated with a propellant for aerosol delivery. In certain embodiments, solutions may be nebulized. Pulmonary administration is further described in PCT application no. PCT/US94/001875, which describes pulmonary delivery of chemically modified proteins.

In certain embodiments, it is contemplated that formulations may be administered orally. In certain embodiments, certain particular molecules that are administered in this fashion may be formulated with or without those carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. In certain embodiments, at least one additional agent can be included to facilitate absorption of certain particular molecules. In certain embodiments, diluents, flavorings, low melting point waxes, vegetable oils, lubricants, suspending agents, tablet disintegrating agents, and binders may also be employed.

In certain embodiments, a pharmaceutical composition may involve an effective quantity of certain particular molecules in a mixture with non-toxic excipients which are suitable for the manufacture of tablets. In certain embodiments, by dissolving the tablets in sterile water, or another appropriate vehicle, solutions may be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving certain particular molecules in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations may include semipermeable polymer matrices in the form of shaped articles, e.g. films, or microcapsules. Sustained release matrices may include polyesters, hydrogels, polylactides (U.S. Pat. No. 3,773,919 and EP 058, 481), copolymers of L-glutamic acid and gamma ethyl-L-glutamate (Sidman et al., *Biopolymers*, 22:547-556 (1983)), poly(2-hydroxyethyl-methacrylate) (Langer et al., *J. Biomed. Mater. Res.*, 15:167-277 (1981) and Langer, *Chem. Tech.*, 12:98-105 (1982)), ethylene vinyl acetate (Langer et al., supra) or poly-D(−)-3-hydroxybutyric acid (EP 133,988). In certain embodiments, sustained release compositions may also include liposomes, which can be prepared by any of several methods known in the art. See e.g., Eppstein et al., *Proc. Natl. Acad. Sci. USA*, 82:3688-3692 (1985); EP 036, 676; EP 088,046 and EP 143,949.

The pharmaceutical composition to be used for in vivo administration typically is sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it may be stored in sterile vials as a solution, suspension, gel, emulsion, solid, or as a dehydrated or lyophilized powder. In certain embodiments, such formulations may be stored either in a ready-to-use form or in a form (e.g., lyophilized) that is reconstituted prior to administration.

In certain embodiments, the present invention is directed to kits for producing a single-dose administration unit. In certain embodiments, the kits may each contain both a first container having a dried protein and a second container having an aqueous formulation. In certain embodiments of this invention, kits containing single and multi-chambered pre-filled syringes (e.g., liquid syringes and lyosyringes) are included.

In certain embodiments, the effective amount of a pharmaceutical composition comprising certain particular molecules to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which certain particular molecules are being used, the route of administration, and the size (body weight, body surface or organ size) and/or condition (the age and general health) of the patient. In certain embodiments, the clinician may titer the dosage and modify the route of administration to obtain the optimal therapeutic effect. In certain embodiments, a typical dosage may range from about 0.1 µg/kg to up to about 100 mg/kg or more, depending on the factors mentioned above. In certain embodiments, the dosage may range from 0.1 µg/kg up to about 100 mg/kg; or 1 µg/kg up to about 100 mg/kg; or 5 µg/kg up to about 100 mg/kg.

In certain embodiments, the frequency of dosing will take into account the pharmacokinetic parameters of certain particular molecules in the formulation used. In certain embodiments, a clinician will administer the composition until a dosage is reached that achieves the desired effect. In certain embodiments, the composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages may be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

In certain embodiments, the composition may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

In certain embodiments, it may be desirable to use a pharmaceutical composition comprising certain particular molecules in an ex vivo manner. In such instances, cells, tissues and/or organs that have been removed from the patient are exposed to a pharmaceutical composition comprising certain particular molecules after which the cells, tissues and/or organs are subsequently implanted back into the patient.

In certain embodiments, certain particular molecules can be delivered by implanting certain cells that have been genetically engineered, using methods such as those described herein, to express and secrete the polypeptides. In certain embodiments, such cells may be animal or human cells, and may be autologous, heterologous, or xenogeneic. In certain embodiments, the cells may be immortalized. In certain embodiments, in order to decrease the chance of an immunological response, the cells may be encapsulated to avoid infiltration of surrounding tissues. In certain embodiments, the encapsulation materials are typically biocompatible, semipermeable polymeric enclosures or membranes that allow the release of the protein product(s) but prevent the destruction of the cells by the patient's immune system or by other detrimental factors from the surrounding tissues.

EXAMPLES

For the following examples, murine CTLA4-Fc was derived from murine CTLA4 (SEQ ID NO. 19). For the following examples, Freund's Complete Adjuvant (CFA) was obtained from Difco (Detroit, Mich.). For the following examples, immunization grade porcine type II collagen was purchased from Griffith's lab (University of Utah, Salt Lake City).

Example 1

Combination Therapy Using KIN2 and CTLA4-Fc in Arthritis-Susceptible B10.RIII Mice Murine CTLA4-Fc and KIN2 (SEQ ID NO 2) used in the study were produced at Amgen.
A. Exemplary Preparation of KIN2

KIN2 may be produced as generally described in U.S. Pat. No. 6,294,170 B1 (the '170 patent). The Fc-IL-1ra fusion protein discussed in the '170 patent is the same as KIN2 discussed herein.

Exemplary Recombinant Human IL-1ra in the '170 Patent

The '170 patent discusses an IL-1ra gene fragment being enzymatically cleaved from another expression vector and being ligated to the expression vector pAMG21 (European Patent Application No. 96309363.8).

The amino acid sequence of IL-1ra is:

```
                                         (SEQ ID NO. 20)
MRPSGRKSSK MQAFRIWDVN QKTFYLRNNQ LVAGYLQGPN

VNLEEKIDVV PIEPHALFLG IHGGKMCLSC VKSGDETRLQ

LEAVNITDLS ENRKQDKRFA FIRSDSGPTT SFESAACPGW

FLCTAMEADQ PVSLTNMPDE GVMVTKFYFQ EDE
```

The '170 patent discusses that the resulting plasmid pAMG21-IL-1ra was purified and the sequence of the IL-1ra gene was confirmed by sequencing. The '170 patent discusses that that plasmid (pAMG21-IL-1ra) (European Patent Application No. 96309363.8) was used later for cloning of rhuIL-1ra-Fc protein. The '170 patent states that an rhuIL-1ra fusion protein was constructed where the Fc region of human IgG1 was fused at the N-terminus of human IL-1ra. The Fc sequence that was chosen for fusions in the '170 patent is shown below. Eight extra amino acid residues AAAEPKSS are present in the N-terminus of the functional Fc region.

Amino acid sequence of Fc3A C8S:

(SEQ ID NO. 22)
AAAEPKSSDK THTCPPCPAP ELLGGPSVFL FPPKPKDTLM

ISRTPEVTCV VVDVSHEDPE VKFNWYVDGV EVHNAKTRPR

EEQYNSTYRV VSVLTVLHQD WLNGKEYKCK VENKALPAPI

EKTISKAKGQ PREPQVYTLP PSRDELTKNQ VSLTCLVKGF

YPSDIAVEWE SNGQPENNYK TTPPVLDSDG SFFLYSKLTV

DKSRWQQGNV FSCSVMHEAL HNHYTQKSLS LSPGK

The underlined sequence was added to the Fc region

Exemplary Description of *E. Coli* Host Strain in the '170 Patent

The '170 patent discusses that a derivative of *E. coli* W1485 (a K12 strain) was obtained from the *E. coli* Genetic Stock Center, Yale University, New Haven, Conn. (CGSC strain #6159). The strain is prototrophic, contains no lambda prophage, and has been cured of the sex factor, F.

The '170 patent states that the CGSC strain #6159 has been altered by selecting for spontaneous resistance to four different phages isolated from phage outbreaks that occurred while conducting fermentation research. The '170 patent states that a first round of phage-resistant mutant isolation, conferring resistance simultaneously to two of the four phages, was performed. The '170 patent states that a sample of one of the phages was diluted and mixed with a culture of the sensitive strain and incubated as a liquid culture at 37° C. for 16-24 hours to select for phage-resistant survivors. The '170 patent states that candidates were isolated from single colonies and tested to confirm phage resistance and ability to grow in minimal medium. The '170 patent states that the mutation obtained in the first round of selection exhibits certain characteristics of a tonA mutation in that the strain simultaneously acquired resistance to phages T5 and φ80.

The '170 patent states that a second phage resistance selection, conferring resistance to the third phage, was performed on May 15, 1984. The '170 patent states that spontaneous phage-resistant mutants were obtained using a plate method. Lawns of sensitive bacteria were spotted with a phage suspension and incubated at 37° C. for two days. Survivors were isolated from colonies in the zone of lysis. They were tested for growth in minimal medium, normal efficiency of plasmid transformation, normal growth rate in complex medium, and normal level of product synthesis. The '170 patent states that the mutation conferring resistance to this phage has been mapped at the btu locus of *E. coli*.

The '170 patent also discusses a third round of phage resistance selection performed using the plate method described above. The '170 patent states that the purified mutant appeared normal by those criteria outlined above (growth in minimal and complex media, efficiency of transformation and level of product synthesis).

Exemplary Preparation of Fc-rhuIL-1ra in the '170 Patent

The '170 patent states that the unique SacII site in the Fc region and the unique SacI site in the IL-1ra gene were used for cloning. The SacII-SacI fragment was synthesized using standard PCR technology. Templates for PCR reactions were plasmid preparations (pAMG21-OPG-Fc and pAMG21-IL-1ra) containing the target genes. The '170 patent states that the overlapping oligos were designed to combine the C-terminal portion of the Fc gene with the N terminal portion of the IL-1ra gene. The '170 patent states that this process allows fusing the two genes together in the correct reading frame after the appropriate PCR reactions have been performed. Initially, one "fusion" oligo for each gene, Oligo #1561-57 for Fc and #1561-56 for IL-1ra, was put into a PCR reaction with a primer 5' to the SacII in Fc (#1561-55) or the SacI site in IL-1ra (#1561-58). At the end of this first PCR reaction, two separate products were obtained, with each individual gene having the fusion site present. In the second round of PCR, the first two PCR products were combined along with the two outside primers (#1561-55 and #1561-58) and the full length fusion DNA sequence was produced.

The '170 patent states that the final PCR gene products were digested with restriction endonucleases SacII and SacI, and a three-way ligation was conducted with the ClaI-SacII Fc fragment with partial pAMG21 sequence isolated from pAMG21-Fc-OPG and the vector ClaI-SacI fragment with partial IL-1ra sequence isolated from pAMG21-IL-1ra. The ligation mixture was transformed into *E. coli* host by electroporation utilizing the manufacturer's protocol. The '170 patent states that clones were screened for the ability to produce the recombinant Fc-rhuIL-1ra and to possess the gene fusion having the correct nucleotide sequence. A methionine residue was added to the junction of the Fc region and the rhuIL-1ra, but it did not interfere with the activity of the fusion protein.

The '170 patent states that the following primers used to construct this Fc-rhuIL-1ra:

```
1651-55
CCA CGA AGA CCC TGA GGT C          (SEQ ID NO. 23)

1561-56
GGG TAA AAT GCG ACC GTC CGG CCG    (SEQ ID NO. 24)
TAA G 1561-57
GGA CGG TCG CAT TTT ACC CGG GCT    (SEQ ID NO. 25)
GAG C 1661-58
CTG GTT GTT GCG CAG GTA G          (SEQ ID NO. 26)
```

Exemplary Expression of Fc-IL-1ra Fusion Proteins in *E. Coli* in the '170 Patent The '170 patent states that the DNA sequence coding for Fc-IL-1ra fusion protein was placed under control of the luxPR promoter in pAMG21 (U.S. Pat. No. 5,169,318 for description of the lux expression system).

The '170 patent states that cultures of pAMG21-Fc-IL-1ra and *E. coli* host were placed in Terrific broth media (Tartof. and Hobbs (1987), *Bethesda Res. Lab. Focus,* 9:12) containing 50 μg/ml kanamycin and were incubated at 30° C. to an OD600 of about 0.8 prior to induction. Induction of recombinant gene product expression from the luxPR promoter of vector pAMG21 was achieved following the addition of the synthetic autoinducer N-(3-oxohexanoyl)-DL-homoserine lactone to the culture media to a final concentration of 30 ng/ml and incubation at 37° C. for a further 6 hours. After 6 hours, bacterial cultures were pelleted by centrifugation. The pelleted cultures were resuspended, lysed by sonication, and soluble and insoluble fractions were separated by centrifugation. The whole cell lysate, and the soluble and insoluble fractions were analyzed by SDS-polyacrylamide gel electrophoresis and by Western blot. The '170 patent states that the induced cultures at 37° C. have inclusion bodies, and over 70% of the product is in the insoluble fraction.

Exemplary Purification of Fc-IL-1ra Fusion Protein

Inclusion bodies (IB) may be mixed at a concentration of 1:10 (wt./vol.) with a solution of 8M guanidine hydrochloride, 3 mM EDTA, 10 mM dithioerythritol and 10 mM 2-n-cyclohexylamino-ethanesulfonic acid pH 9.3, and stirred at room temperature for 20 minutes. Solid urea may then be added to make the final urea concentration 4M. One may further stir the mixture at room temperature for 40 minutes.

With stirring, the solubilized inclusion bodies may be slowly, drop by drop, diluted to a concentration of 1:20 (vol./vol.) into the refolding buffer of 2.5 M 1,3-Dimethyl-Urea, 0.2 M Arg, 4.5 mM cysteine and 1 mM cystamine dihydrochloride pH8.8. The mixture may then set at 4° C. overnight, without stirring.

The refolded mixture may be centrifuged for 1 hour in a J6-B centrifuge. The resultant supernatant may be concentrated 3 times and buffer changed into 25 mM tris pH 8.8 with an ultrafiltration system. The retentate may be titrated by 6M HCl to pH 6.5. Some precipitate may be formed at pH 6.5 and may be discarded after being centrifuged for 1 hour in the J6-B centrifuge.

The supernatant from ultracentrifugation may be passed through a column of Q High Performance (QHP) (15 g IB's/50 ml) resin (Pharmacia Biotech, Inc., Piscataway, N.J.) pre-equilibrated with 20 mM 2-n-morpholinoephane-sulfonic acid pH 6.5 buffer. The flow-through from the QHP (QFT) and the early eluted fractions from the QHP column which contains the product may be collected.

Solid ammonium sulfate may be added into the O-FT pool to a concentration of 0.7 M. The sample may then be loaded onto a Phenyl-toyo column (Toso Haas, Philadelphia, Pa.) (15 g IB's/15 ml resin) pre-equilibrated with 0.7 M ammonium sulfate in 20 mM sodium phosphate pH 7.0. After washing with 0.7 M ammonium sulfate, the column may be eluted with a linear gradient from 0.7 M ammonium sulfate to 0.2 M ammonium sulfate in 20 mM sodium phosphate pH 7.0 buffer. Fractions containing the product may be pooled based on SDS-PAGE analysis.

The HIC pool may be dialyzed into 25 mM sodium phosphate pH 7.0. The dialyzed sample may be titrated by 2 M citric acid to pH 5.0, and then loaded onto a SOHO column (15 g IB's/7 ml resin) pre-equilibrated with 20 mM citric acid pH 5.0. After washing with 25 mM citric acid pH 5.0 and pH 6.0 buffer the column may be eluted with a linear gradient from 0 M to 0.7 M NaCl in 25 mM citric acid pH 6.0 buffer.

The fractions containing the product may be pooled.

B. Therapy in Mice

Porcine type II collagen was dissolved in 0.01 N acetic acid at a concentration of 2 mg/ml and then emulsified at a 1:1 ratio with CFA (Difco). Arthritis susceptible B10.RIII (H-2$^r$) mice (from Jackson Lab, Bar harbor, Me., USA) were immunized with 100 µl of emulsion intradermally at the base of the tail. (Nabozny et al. *Autoimmunity* 20, 39-49 (1995)).

Mice were monitored once every day for the development of arthritis. Arthritis severity was determined using a grading system (Khare et al. *J. Immunol.*, 155: 3653-3659, 1995) for each paw as follows: 0: no arthritis; 1: redness or swelling 1-3 toes; 2: severe swelling of paw; 3: joint ankylosis. The score of each limb was summed, thus giving a severity range from 0 to 12 for each animal. The scores for the mice were summed and divided by the total number of mice to generate a mean arthritis score. As mice developed disease, they were randomized to study groups (9-10 mice/group) and treatment was initiated.

Prior to injections, KIN2 was suspended in A5S (A5S buffer includes 10 mM Acetic Acid and 5% Sorbitol pH 5.0) and murine CTLA4-Fc was suspended in phosphate buffered saline (PBS). Mice were treated by injection of 100 g of KIN2, 100 µg murine CTLA4-Fc, or 100 µg each of KIN2 and murine CTLA4-Fc at day 0, +1, +2, +4, +6, +8 and +10 post clinical onset of disease. 100 µg is equivalent to 5 mg of therapeutic per Kg weight of animal (5 mg/Kg). Mice were injected in 100 µl volumes, except in the combination experiment, wherein the mice received two separate injections of 100 µl each. Injections of PBS were used as a control. Mice were monitored once every day and a mean arthritis score was calculated.

KIN2 reduced the severity of collagen-induced arthritis in mice when given alone whereas murine CTLA4-Fc given alone had no effect when compared to PBS control. The combination of KIN2 and murine CTLA4-Fc reduced collagen-induced arthritis for an extended period of time compared to KIN2 alone, as shown in FIG. 1.

Example 2

Combination Therapy Using PEG sTNFR-1 and CTLA4-Fc in Arthritis-Susceptible B10.RIII Mice PEG sTNFR-1 2.6D, murine CTLA4-Fc, and Fc used in the study were produced at Amgen.

A. Exemplary PEGylation of sTNFR-I

PEG was added to an sTNFR-1 2.6D molecule to construct PEG sTNFR-1 2.6D. sTNFR-1 2.6D molecules include, but are not limited to, sTNFR-1 2.6D/C105, sTNFR-1 2.6D/C106, and sTNFR-1 2.6D/N105 (SEQ ID NO. 4). PEG may be added to a sTNFR-1 2.6D molecule in a manner similar to how PEG may be added to sTNFR-1 2.6D/N105, as generally described in published PCT Application No. WO 98/01555 (PCT '555).

Exemplary Preparation of sTNFR-I 2.6D/N105-t-BuPEG (33 kDa) in PCT '555

PCT '555 states that to a cooled (4° C.), stirred solution of sTNFR-I 2.6D/N105 (SEQ ID NO. 4) (3.5 mg/ml) in 50 mM sodium acetate, pH 4, is added a 3-fold molar excess of t-BuPEG (mono-t-butoxy-polyethylene glycol, average MW=33 kDa, Shearwater Polymers, Inc.). NaCNBH$_3$ is added to a final concentration of 20 mM, and the reaction mixture is stirred at 7° C. for 18-24 hours.

PCT '555 states that the extent of the protein modification during the course of the reaction is monitored by SEC HPLC using a TSKG3000sw$_{XL}$ column (Toso Haas, Montgomeryville, Pa.) eluting with 0.1 M sodium phosphate buffer pH 6.9, 0.5M NaCl, and 10% ethanol at 0.7 ml/min (Toso Haas, Montgomeryville, Pa.).

PCT '555 states that the pH of the reaction mixture is adjusted to ca. 3.5 with 1M HCl, and the reaction mixture is diluted with water to a final protein concentration of 1.5 mg/ml.

PCT '555 states that sTNFR-I 2.6D/N105-t-BuPEG (33 kDa) is separated from the excess of t-BuPEG and other reaction by-products by using a SP Sepharose HP 16/10™ ion-exchange chromatography (Pharmacia Biotech, Inc., Piscataway, N.J.).

PCT '555 states that the reaction mixture is loaded onto the column and the unreacted t-BuPEG is eluted with 3 column volumes of the starting Buffer A (20 mM sodium acetate, pH 4.0). The sTNFR-I 2.6D/N105-t-BuPEG (33 kDa) is eluted using a linear 20 column volume gradient from 0-30% Buffer B (1M NaCl in 20 mM acetate, pH 4.0. The eluent is monitored at 280 nm. Each fraction containing sTNFR-I 2.6D/N105-t-BuPEG (33 kDa) is analyzed by SDS-PAGE using 4-20% precast gradient gels (Novex, San Diego, Calif.). Based on SDS-PAGE analysis results, fractions are pooled, concentrated, and sterile filtered. Each final pool of purified sTNFR-I 2.6D/N105-t-BuPEG (33 kDa) is again analyzed by SDS-PAGE and SEC HPLC. This protein is formulated in 10 mM sodium phosphate, pH 6.5 and 20 mM NaCl.

Exemplary Preparation of sTNFR-I 2.6D/N105-33 kDa (Me-PEG) in PCT '555

PCT '555 states that to a cooled (7° C.), stirred solution of sTNFR-2.6D/N105 (4 mg/ml) is added 10% acetic acid until the pH is 5.0. To this solution is added 15 mM NaCNBH$_3$ and a 2-fold molar excess of t-butoxy PEG (t-butoxy polyethylene glycol, average MW=33 kDa, Shearwater Polymers, Inc.). The reaction mixture is stirred briefly at the same temperature and then allowed to incubate for ~18 hours.

PCT '555 states that after 18 hours, the protein concentration in the reaction mixture is adjusted to pH 3.0 with citric acid.

PCT '555 states that sTNFR-I 2.6D/N105-MePEG (33 kDa) is separated from the excess of MePEG and other reaction by-products by ion exchange chromatography using an SP Sepharose HP™ column (Pharmacia Biotech, Inc., Piscataway, N.J.).

PCT '555 states that the reaction mixture is loaded (no more than 8 mg/ml of resin) onto the column and the unreacted MePEG is eluted with 3 column volumes of the starting buffer A (20 mM sodium citrate, pH 3.0). The sTNFR-I 2.6D/N105-MePEG (33 kDa) is eluted using a linear 16 column volume gradient from 0.1-0.5 M NaCl in 20 mM citrate, pH 3.0. The eluent is monitored at 280 nm. Each fraction containing sTNFR-I 2.6D/N105-MePEG (33 kDa) is analyzed by SDS-PAGE using 4-20% precast gradient gels (Novex, San Diego, Calif.). Based on SDS-PAGE analysis results, fractions are pooled, concentrated, and sterile filtered. Each final pool of purified sTNFR-I 2.6D/N105-MePEG (33 kDa) is again analyzed by SDS-PAGE. The purified sTNFR-I 2.6D/N105-MePEG (33 kDa) is concentrated to 5-20 mg/mL and formulated in either PBS, pH 6.5 (10 mM sodium phosphate, 35-100 mM NaCl) or 20 mM acetate, 100 mM NaCl, pH 5.0.

B. Therapy in Mice

Arthritis was induced in B10.RIII mice by injection with porcine type II collagen as described in Example 1. Prior to the injections, murine CTLA4-Fc and PEG sTNFR-1 2.6D were suspended in PBS. Mice were administered by injection of 100 µg of PEG sTNFR-1 2.6D, 100 µg murine CTLA4-Fc, or 100 µg each of PEG sTNFR-1 2.6D and murine CTLA4-FC at day 0, +1, +2, +4, +6, +8 and +10 post clinical onset of disease. 100 µg is equivalent to 5 mg of therapeutic per Kg weight of animal (5 mg/Kg). Mice were injected in 100 µl volumes. PBS and human IgG1 Fc (Protein Science, Amgen, Thousand Oaks, Calif.) were used as controls. Mice were evaluated once a day for a mean arthritic score as described in Example 1.

PEG sTNFR-1 2.6D reduced the severity of collagen-induced arthritis in mice when given alone whereas murine CTLA4-Fc given alone had no effect when compared to PBS control. The combination of PEG sTNFR-1 2.6D and murine CTLA4-Fc reduced collagen-induced arthritis for an extended period of time compared to PEG sTNFR-1 2.6D alone, as shown in FIG. 2.

Figure 2:
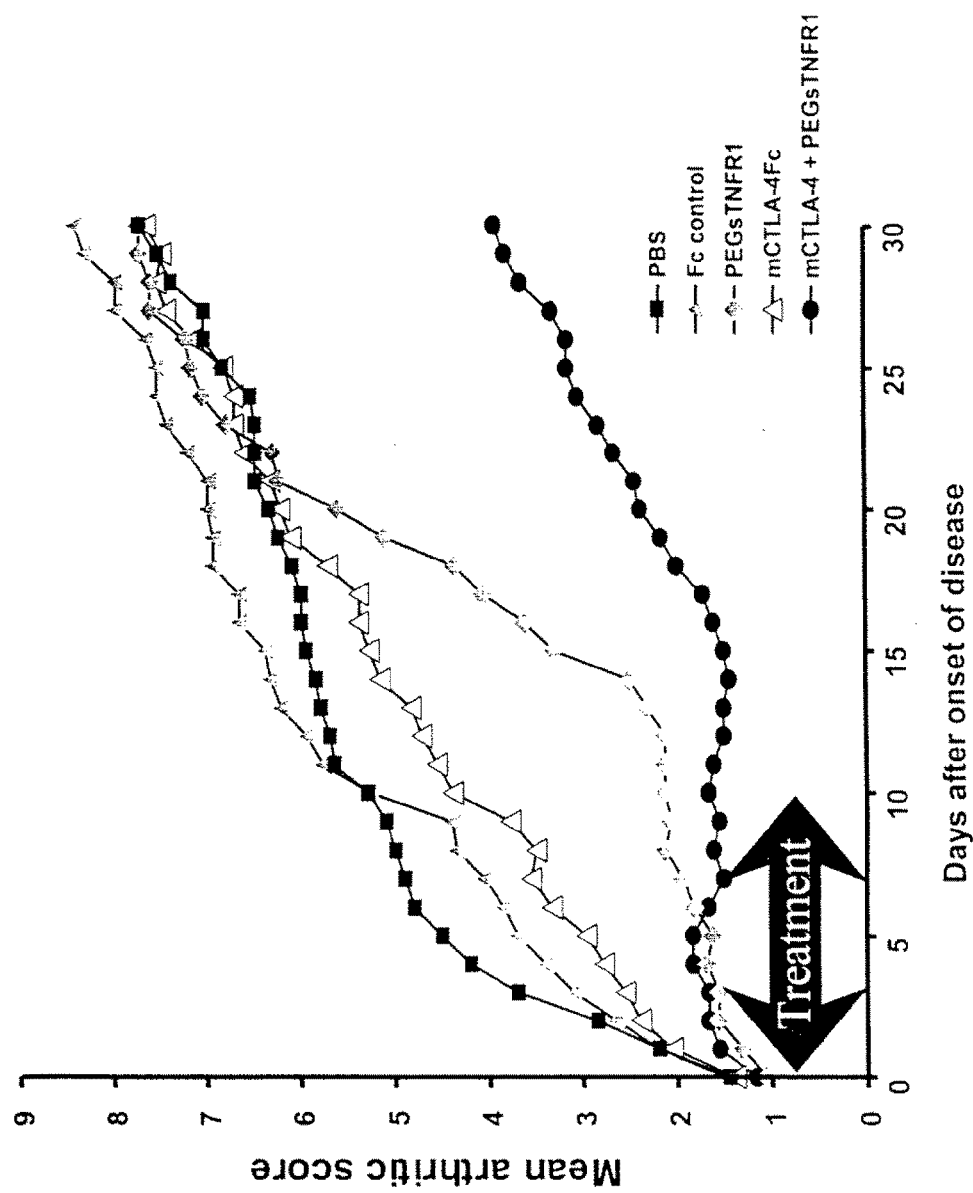
FIG. 2 shows mean arthritis scores in CIA animals during and after treatment with an TNF-alpha inhibitor (PEG sTNFR-1 2.6D), murine CTLA4-Fc fusion protein, and a combination thereof. The arrow indicates that animals were administered by injection of 100 µg of PEG sTNFR-1 2.6D, 100 µg murine CTLA4-Fc, or 100 µg each of PEG sTNFR-1 2.6D and murine CTLA4-Fc at day 0, +1, +2, +4, +6, +8 and +10 post onset of disease. 100 µg is equivalent to 5 mg of therapeutic per Kg weight of animal (5 mg/Kg). Phosphate buffered saline (PBS) and Fc were used as controls.

Serum samples were taken ten days after the conclusion of the experiment shown in FIG. 2 and assayed for type II collagen specific antibodies. Briefly, porcine type II collagen at 2 µg/ml was coated onto high-binding plates (Nalge Nunc Intl., Denmark) overnight. The plates were washed with PBS-Tween 20 and blocked with 1% bovine serum albumin (BSA) in PBS. Serum samples were added to the plates at dilutions ranging from 1:100 to 1:6400, and incubated for three hours at room temperature. After incubation, excess sera was washed from the plates with PBS-Tween 20. Anti-IgG1 and anti-IgG2b antibodies (Southern Biotech, Birmingham, Ala.) labeled with Horse Radish Peroxidase (HRP) were added to the plates and incubated for 1 to 2 hours. Excess reagents were washed from the plates with PBS-Tween 20. The reaction was developed using a 3,3',5,5'-Tetramethyl-Benzidine (TMB) solution (Sigma, St. Louis, Mo.) and the optical density at 450 nm was measured. The optical density values obtained were compared with standard serum from type II collagen immunized mice.

The level of type II collagen specific antibodies was reduced in animals injected with PEG sTNFR-1 2.6D and murine CTLA4-Fc compared to animals injected with murine CTLA4-Fc alone as measured by anti-IgG1 antibodies, and shown in FIG. 3A. The level of type II collagen specific antibodies was reduced in animals injected with PEG sTNFR-1 2.6D and murine CTLA4-Fc compared to both animals injected with PEG sTNFR-1 2.6D alone and animals injected with murine CTLA4-Fc alone, as measured by anti-IgG2b antibodies, and shown in FIG. 3B.

Example 3

Combination Therapy Using Viral Vectors Expressing IL-1ra, sTNFR-I and/or CTLA4

Vector Construction

Adeno-associated virus (AAV) cloning vectors were based on the pBluescript SK II vector (Stratagene, La Jolla, Calif.). An oligonucleotide linker containing a Bgl II site (CGC-GAGATCTTGCGCAAGATCT (SEQ ID NO. 28)) was inserted between the two BssH II sites of pBSSK II. AAV2 genomic DNA (available from the American Type Culture Collection under accession number 37215; see also Laughlin et al. *Gene* 23, 65-73 (1983)) having flanking Bgl II sites was inserted into the linker. A NruI site and a XhoI site were introduced by site directed mutagenesis at positions 145 and 4530 respectively of the AAV2 nucleotide sequence (Srivastava et. al. *J. Virol.* 45, 555-564 (1983) and NCBI Accession No. NC-001401). The resulting construct was digested with NruI and XhoI and the AAV2 sequence from nucleotide 146 to nucleotide 4534 was removed. A DNA fragment comprising either a cytomegalovirus (CMV) early gene promoter/enhancer (Invitrogen, Carlsbad, Calif.) or an EF1a promoter (PEF1HisA, Invitrogen) followed by a multiple cloning site derived from pcDNA3.1 (Invitrogen) was inserted between remaining nucleotides 145 and 4535 of the AAV2 sequence. The bovine growth hormone poly adenylation site from pcDNA3.1 was inserted downstream of the multiple cloning site. cDNA encoding either human IL-1ra (SEQ ID NO. 20), rat sTNFR-1, human CTLA4 (SEQ ID NO. 2), or beta-galactosidase (Herz et al. *Proc. Natl. Acad. Sci.* 90, 2812-2816 (1993)) was cloned into Nhe I and Not I sites respectively using standard cloning procedures. Rat sTNFR-1 was derived from rat TNFR-I (SEQ ID NO. 21).

The packaging plasmid pTrans was constructed using the pBluescript SK+ vector (Stratagene, La Jolla, Calif.). An AAV2 genomic fragment spanning nucleotides 191-4497 in the AAV2 genome was obtained by digestion with ClaI and SnaBI and the fragment was inserted into pBluescript SK+ digested with ClaI and EcoRV. AAV2 nucleotide sequence 1849-2202 was inserted into AAV2 nucleotide sequence at nucleotide 320 using standard cloning methods. An adenovirus helper plasmid containing the adenovirus E2a, E4orf 6 and VA sequence of adenovirus 5 (Gomez-Foix et al. *J. Biol.*

Chem. 267, 25129-25134 (1992)) was cloned into pBluescript SK+ using standard cloning procedures.

Adeno-Associated Virus Production

Monolayers of human embryonic kidney 293T cells were cultured in 5% $CO_2$ at 37° C. in medium A (Dulbecco's modified Eagle's medium containing 100 units/ml penicillin and 100 µg/ml streptomycin sulfate) supplemented with 10% (v/v) fetal calf serum. Cotransfection of AAV cloning vector, pTrans and pHelper plasmid in ratio of 1:1:3 were performed using a calcium phosphate precipitation method (Sambrook et al. Molecular Cloning, supra). Cells were harvested and viruses were released by freezing and thawing. Viruses were purified using heparin sulfate chromatography and titered using a dot blot method described in Auricchiv et. al. *Human Gene Therapy* 12, 71-76).

Administration to Animals 6-8 week old male B10.RIII mice (Charles River, Wilmington, Mass.) were randomly assigned to treatment groups (n=10) and were injected via tail vein with 100 µg porcine type II collagen in 1×CFA intradermally in the base of the tail. At day 19, mice were injected intravenously with 100 µl of PBS containing $7 \times 10^{12}$ particles of recombinant AAV carrying β-gal, IL-1ra, sTNFR-1, CTLA-4 or a combination as indicated. Blood was collected from tail veins for ELISA to quantify the protein expression level. On day 21 mice were boosted with 100 µg porcine type II collagen in 1×CFA intradermally.

Expression of human IL-1ra, rat sTNFR-I, and human CTLA4 reduced the incidence and severity of collagen-induced arthritis in mice when vectors were administered individually compared to a β-galactosidase control. The combination of sTNFR-I and CTLA4 expression by coadministration of vectors reduced the severity and incidence of collagen-induced arthritis to a greater extent than expression of those proteins individually, as shown in FIGS. 4 and 5.

Figure 4:
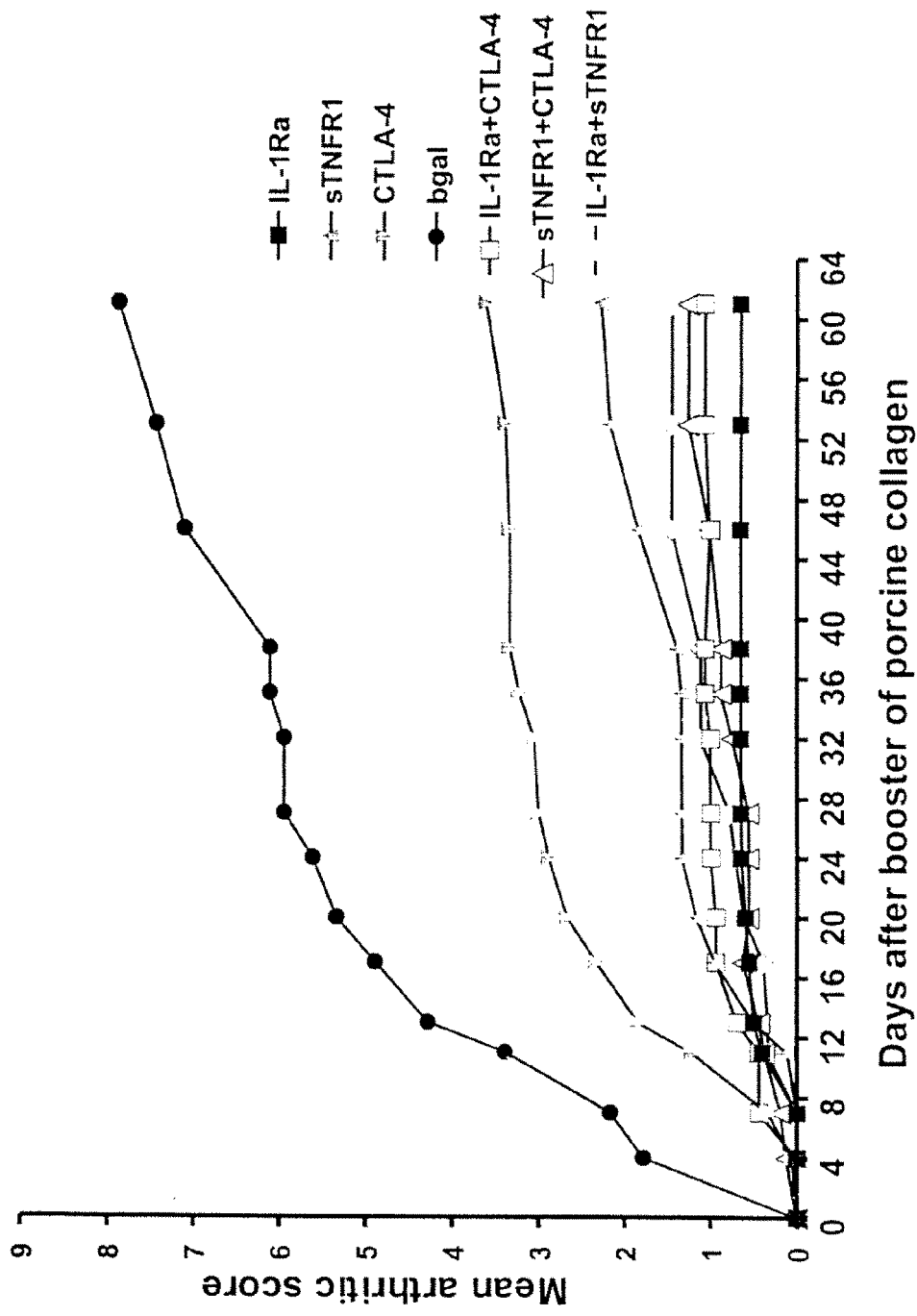
FIG. 4 shows mean arthritis scores in CIA male B10.RIII mice modified with vectors expressing IL-1ra, s-TNFRI (SEQ ID NO. 4) and/or CTLA-4 SEQ ID NO 2). At day 19 after a booster of porcine type II collagen, mice were administered viral vectors encoding IL-1ra, s-TNFRI, CTLA-4 or β-galactosidase as a control. For combination therapy, mice were administered both IL-1ra and CTLA-4 vectors, s-TNFRI and CTLA-4 vectors, or IL-1ra and s-TNFRI vectors.
Figure 5:
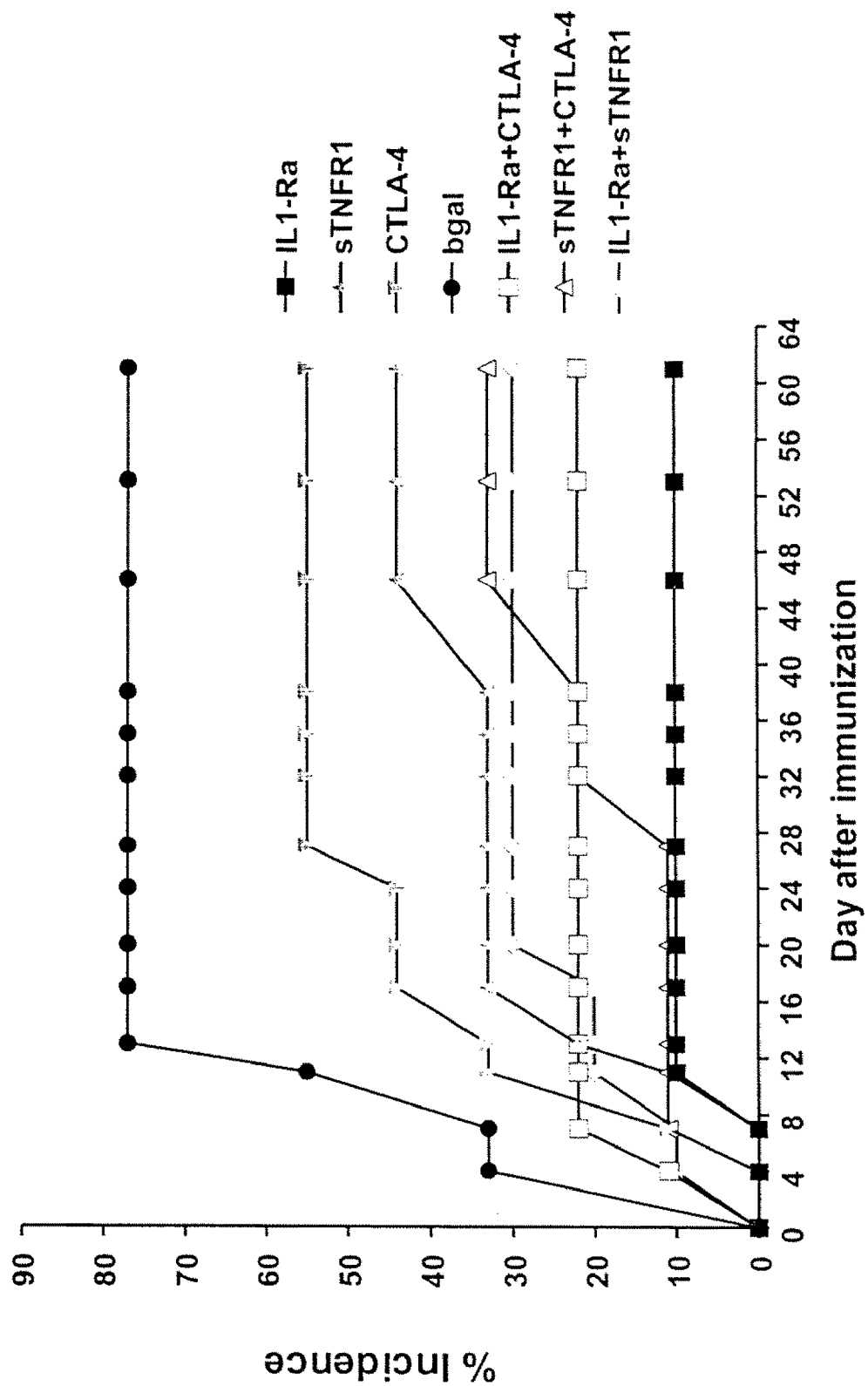
FIG. 5 shows the percent incidence of arthritis in the same groups of mice as in FIG. 4.

Serum samples from the treatment groups of mice shown in FIG. 4 were taken several weeks after booster of porcine type II collagen and levels of type II collagen specific antibodies were assayed as described above in Example 2, except that anti-IgG3 antibodies were used.

Figure 6:
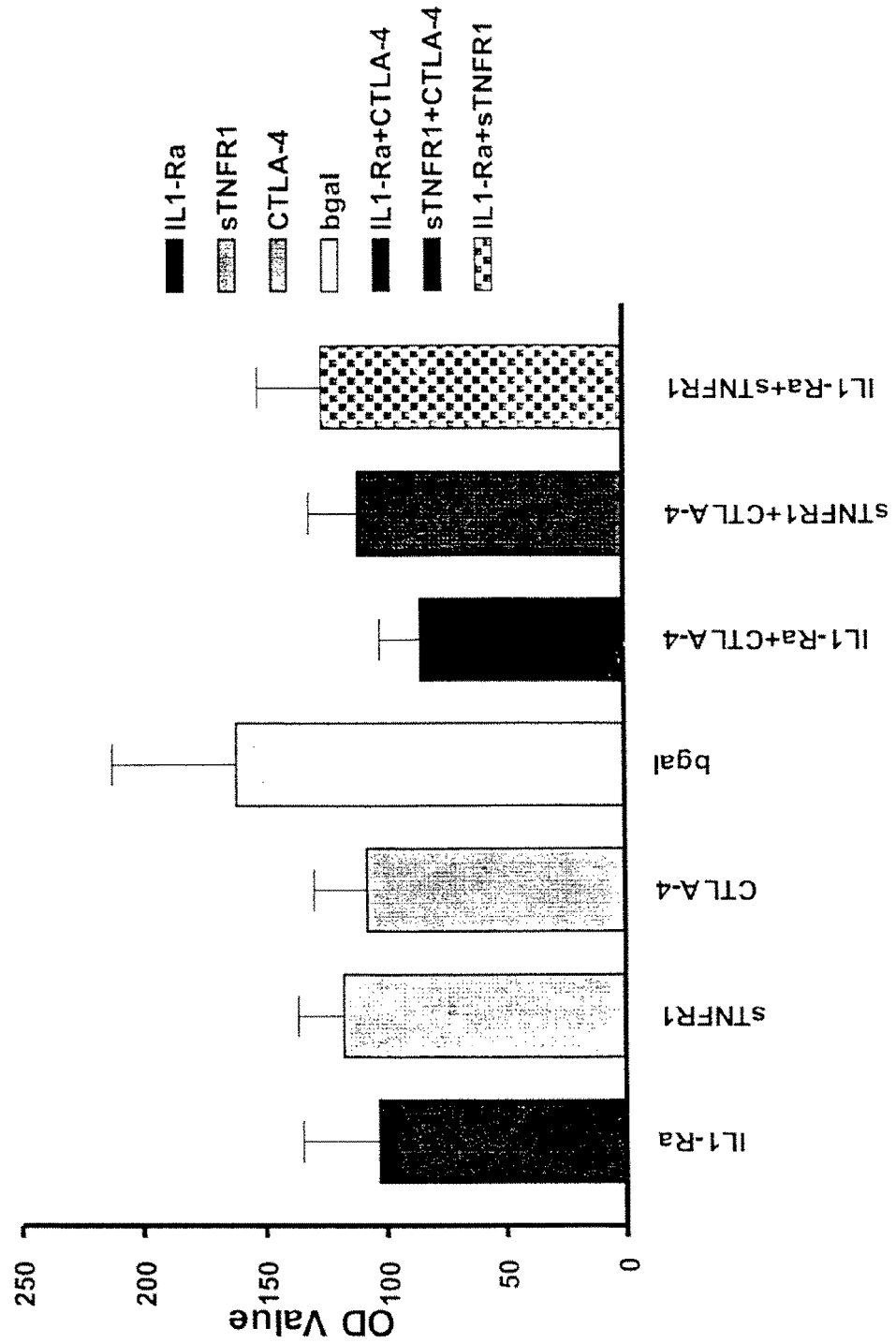
FIG. 6 shows levels of type II collagen (CII) specific antibodies present in bleeds from the same groups of mice as in FIG. 4. Mice were bled several weeks after booster of porcine type II collagen and antibodies were assayed as described in Example 3.

The level of type II collagen specific antibodies was reduced in animals injected with sTNFR-1 and CTLA-4 vectors compared to animals injected with a sTNFR-1 vector alone as measured by anti-IgG3 antibodies, and shown in FIG. 6. The level of type II collagen specific antibodies was reduced in animals injected with IL1-ra and CTLA-4 vectors compared to both animals injected with an IL1-ra vector alone and animals injected with a CTLA-4 vector alone, as measured by anti-IgG3 antibodies, and shown in FIG. 6.

Example 4

Combination Therapy Using AGP3 Pb and CTLA4-Fc in Lupus Mice

The CTLA4-Fc protein and the AGP3 peptibody (an AGP3 tandem dimer peptide-Fc fusion) ("AGP3 Pb") (SEQ ID NO. 1) were produced at Amgen.

A. Exemplary Production of AGP3 Peptibody

AGP3 Pb may be prepared as generally described in published PCT Application No. WO 02/092620 (PCT '620).

PCT '620 discusses that an inhibitory AGP-3 Pb was constructed in which a tandem dimer of a peptide was fused in-frame to the Fc region of human IgG1. PCT '620 states that an inhibitory peptibody may be constructed by annealing pairs of oligonucleotides to generate a duplex encoding the peptide and a linker comprised of 5 glycine residues and one valine residue as an NdeI to SalI fragment.

PCT '620 states that these duplex molecules were ligated into a vector (pAMG21-RANK-Fc, described in PCT '620) containing the human Fc gene, also digested with NdeI and SalI. PCT '620 states that the resulting ligation mixtures were transformed by electroporation into *E. coli* strain 2596 cells (GM221, described in PCT '620). PCT '620 states that clones were screened for the ability to produce the recombinant protein product and to possess the gene fusion having the correct nucleotide sequence. PCT '620 states that a single such clone was selected for each of the peptibodies.

pAMG21-RANK-Fc fusion constructs may be expressed in *E. coli* as described in WO 02/092620.

B. Therapy in Mice (NZB×NZW) F1 mice spontaneously develop lupus-like symptoms at 6 to 9 months of age and usually die at 10 to 12 months of age (Vyse et al. *Ann Rev Immunol* 16, 261-292 (1998)). Prior to treatment, mice were pre-screened for protein in the urine with Albustix® reagent strips (Bayer Corp., Elkhart, Ind.) and those having greater than 100 mg/dl of protein in the urine were not included in the experiment. Prior to the injections, murine CTLA4-Fc and AGP3 Pb were suspended in PBS. Six month old (NZB×NZW) F1 mice were treated intraperitoneally 3 times per week for 60 days with 100 µg (4 mg/kg) AGP3 Pb, 50 µg (2 mg/kg) murine CTLA4-Fc, or a combination thereof. 100 µg is equivalent to 4 mg of therapeutic per Kg weight of animal (4 mg/Kg). 50 µg is equivalent to 2 mg of therapeutic per Kg weight of animal (2 mg/Kg). 100 µg of human IgG1 Fc protein or 100 µl PBS were administered as controls. Protein in the urine was evaluated monthly throughout the life of the experiment. The combination of AGP3 Pb and murine CTLA4-Fc showed a marked improvement in survival compared to AGP3 Pb or murine CTLA4-Fc alone, as shown in FIG. 7.

Lupus-prone mice in the treatment groups were assayed for proteinuria every 30 days using Albustix® reagent strips (Bayer Corp., Elkhart, Ind.). FIG. 8 shows the percent of mice having greater than 300 mg/dl of proteinuria at various times after initial treatment. The combination treatment of AGP3 Pb and murine CTLA4-Fc reduced the extent and delayed the onset of proteinuria compared to administration of AGP3 Pb or murine CTLA4-Fc alone, as shown in FIG. 8.

Figure 7:
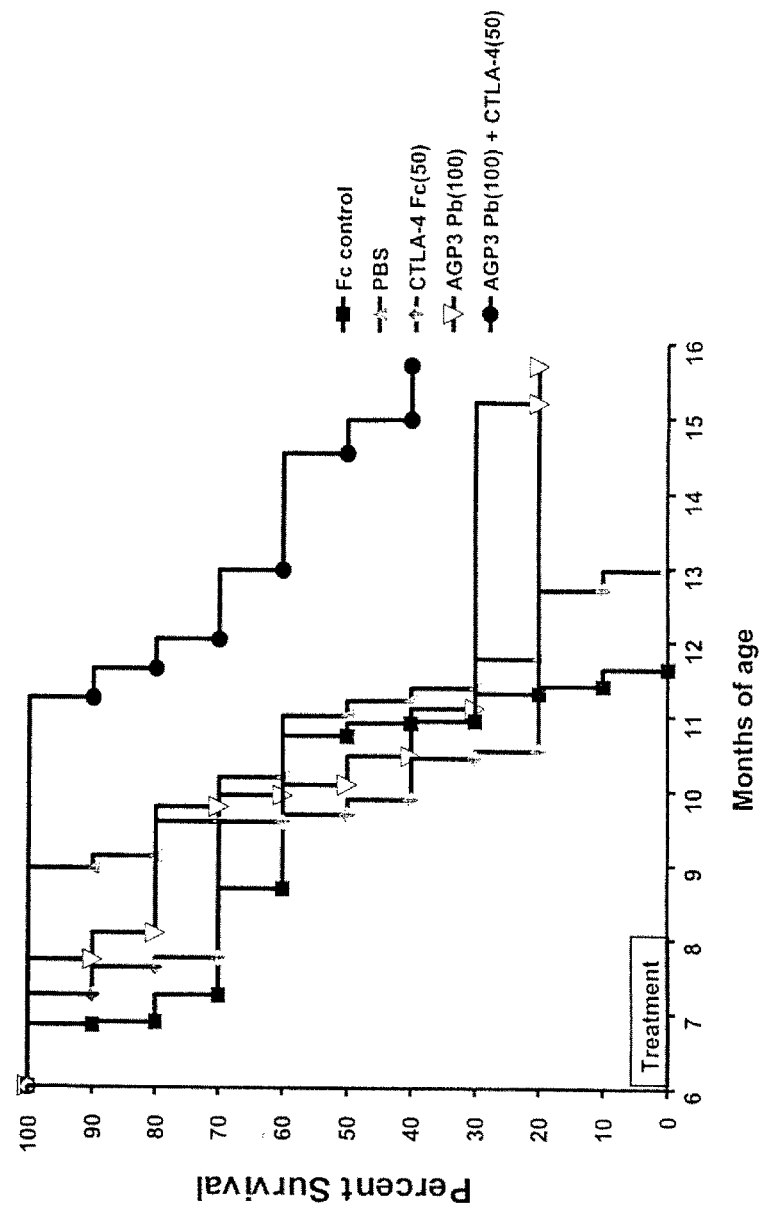
FIG. 7 shows percent survival of six month old (NZBx-NZW) F1 mice injected three times per week for two months with 100 μg of AGP3 peptibody (an AGP3 tandem dimer peptide-Fc fusion) ("AGP3 Pb") (SEQ ID NO. 12), 50 μg of murine CTLA4-Fc, or a combination of 100 μg of AGP3 Pb and 50 μg of murine CTLA4-Fc. 100 μg is equivalent to 4 mg of therapeutic per Kg weight of animal (4 mg/Kg). 50 μg is equivalent to 2 mg of therapeutic per Kg weight of animal (2 mg/Kg). Fc and PBS were used as controls.

Three randomly chosen lupus-prone mice from each of the treatment groups shown in FIG. 7 were bled 60 days after the initial treatment with AGP3 Pb, murine CTLA4-Fc, or the combination thereof, and the blood samples tested for the presence of B220-positive cells. The B220 antibody detects B cells. Red blood cells were lysed and white blood cells were stained with fluorescein isothiocyanate-labeled CD4 (anti-CD4-FITC), phycoerythrin (PE) labeled CD8 (anti-CD8-PE), and cychrome labeled B220 (B220-cyc), all purchased from BD Pharmingen (San Diego, Calif.) at 4° C. for 30 min. Following incubation, cells were washed 2 to 3 times with and fixed in FACS buffer containing paraformaldehyde. Staining and analysis was performed using standard protocols as described in Khare et al. *J Immunol* 160, 101-106 (1998)).

Figure 9A:
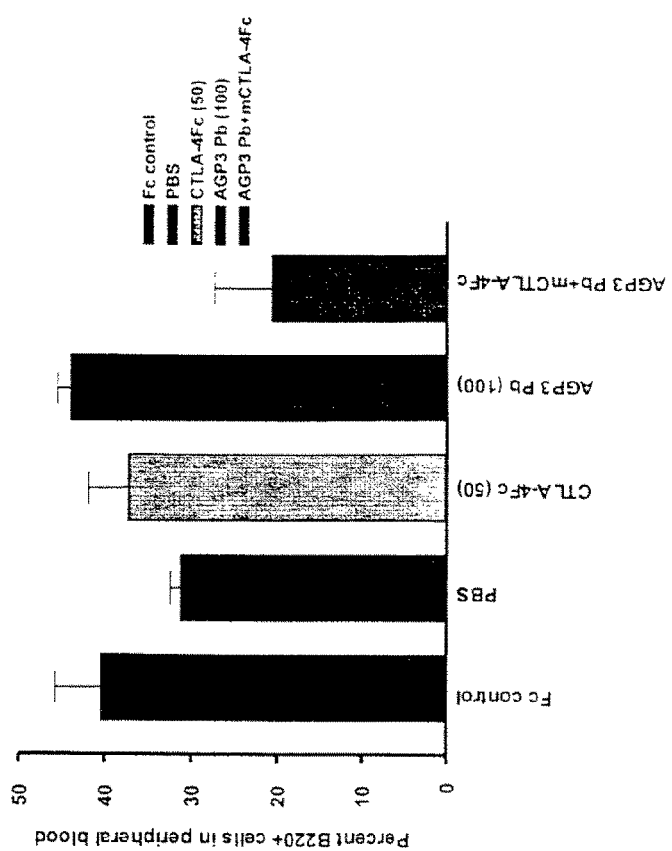
FIGS. 9A and 9B show the percentage of B220-positive B cells in the peripheral blood of mice in the treatment groups shown in FIG. 7. B220 positive B cells were determined by FACS staining. (A) The percent of B220+ cells in peripheral blood was determined at the end of the treatment period. (B) The percent of B220+ cells in peripheral blood was determined one month after the end of the treatment period.
Figure 9B:
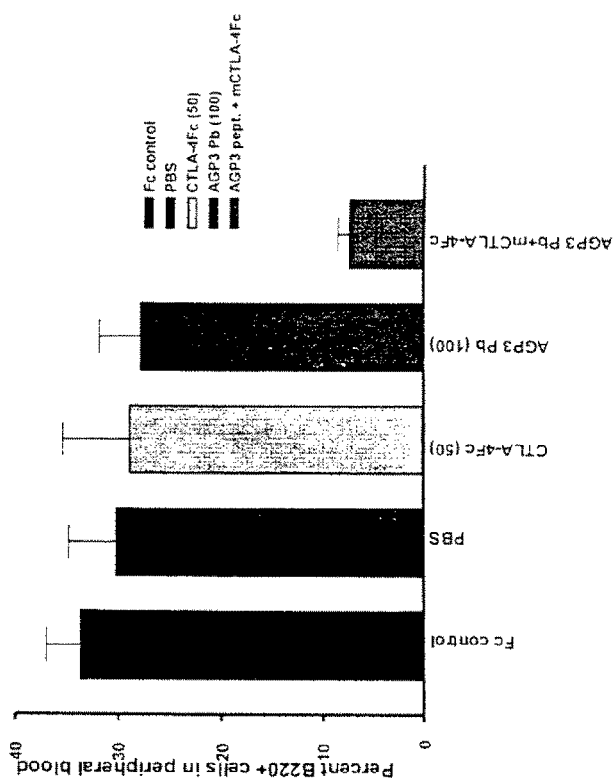

The percent of B220-positive cells was sharply reduced in mice administered both AGP3 Pb and murine CTLA4-Fc, compared to individual administration, as shown in FIG. 9A. Furthermore, this reduction persisted for 30 days after the last administration of AGP3 Pb and murine CTLA4-Fc, as shown in FIG. 9B.

Serum samples taken from the various treatment groups of mice at day 0, 30, 60, and 90 were assayed for the presence of antibodies to double stranded DNA. Adsorbent plates were coated overnight at 4° C. with 50 µl of a 1:1 solution of 1

μg/ml plasmid DNA (Immunovision, Springdale, Ariz.) diluted in PBS with 1 mg/ml methylated bovine serum albumin (BSA; Sigma, St. Louis, Mo.) dissolved in water. Plates were gently washed three times with PBS/Tween 20 and blocked with 75 μl of 2% BSA/PBS for up to 2 hours. 25 μl of diluted samples were added to the plates to achieve final dilution factors of 100, 400, 1600, and 6400 fold. Serum from TALL-1 transgenic mice (Khare et al. *Proc. Natl. Acad. Sci. USA* 97, 3370-3375 (2000)) were used as standards. Samples were allowed to incubate for a few hours or overnight whereupon plates were washed again. Anti-mouse IgG and anti-mouse IgM (Southern Biotech, Birmingham, Ala.) labeled with HRP were diluted 1:2000 and added to the plates. The HRP labeled antibodies were incubated for about one hour. After incubation, plates were washed and developed with TMB solution and the optical density at 450 nm was determined.

Figure 10:
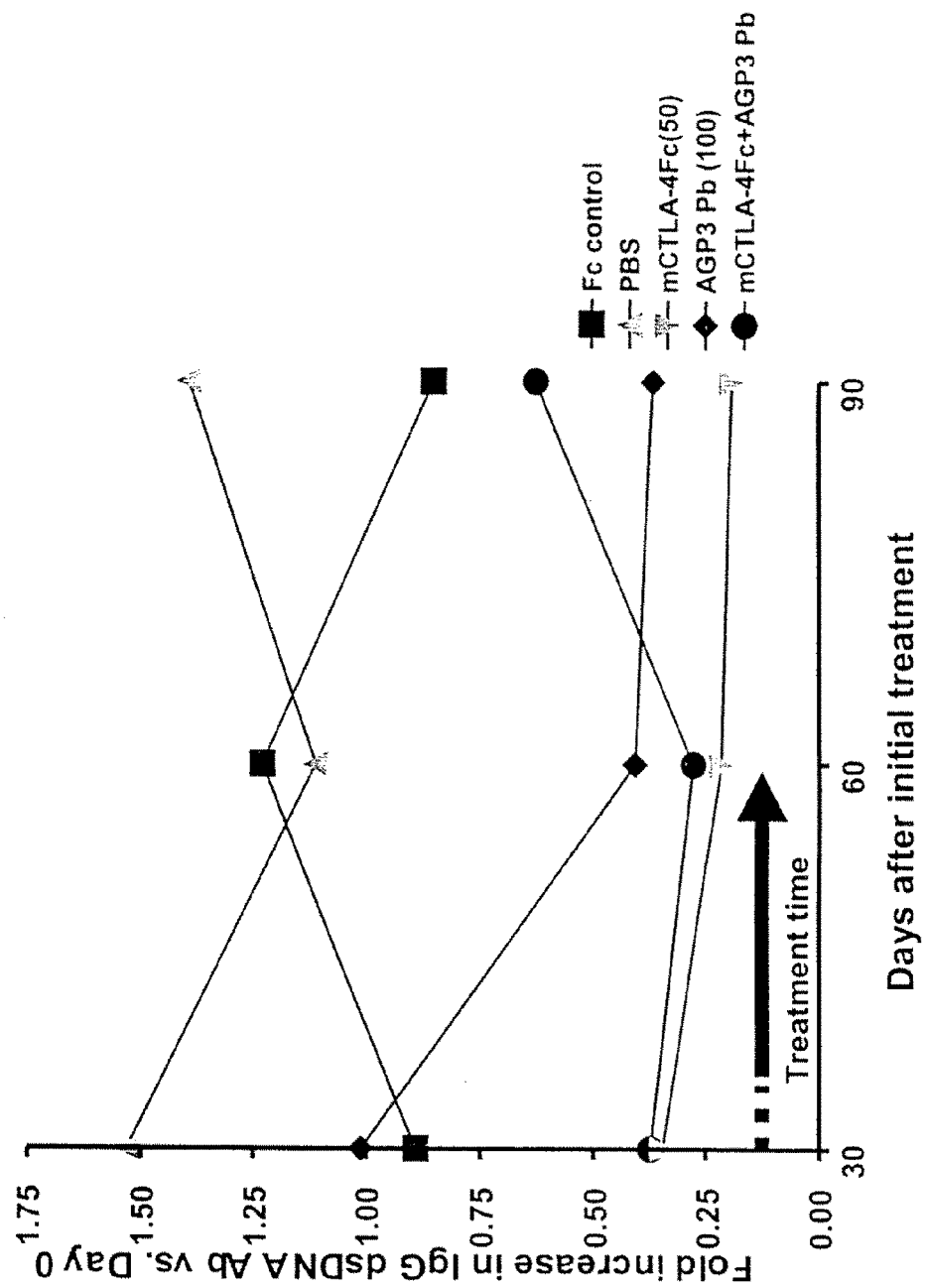
FIG. 10 shows the changes in levels of IgG specific double stranded DNA in serum collected at 30, 60 and 90 days after initial treatment with either AGP3 Pb (an AGP3 tandem dimer peptide-Fc fusion), murine CTLA4-Fc or the combination thereof. The change of dsDNA antibody level was determined by dividing day 30, 60 and 90 antibody levels by their day 0 pre-treatment antibody levels for all ten mice (mean+/–standard error). Serum was collected on those days and assessed for levels of dsDNA antibody using ELISA techniques as described in Example 4.

At 30 and 60 days after treatment, the level of double-stranded DNA specific antibodies was reduced in animals injected with mCTLA-4Fc and AGP3 Pb compared to animals injected with AGP3 Pb alone as measured by anti-IgG antibodies, as shown in FIG. 10.

Figure 11:
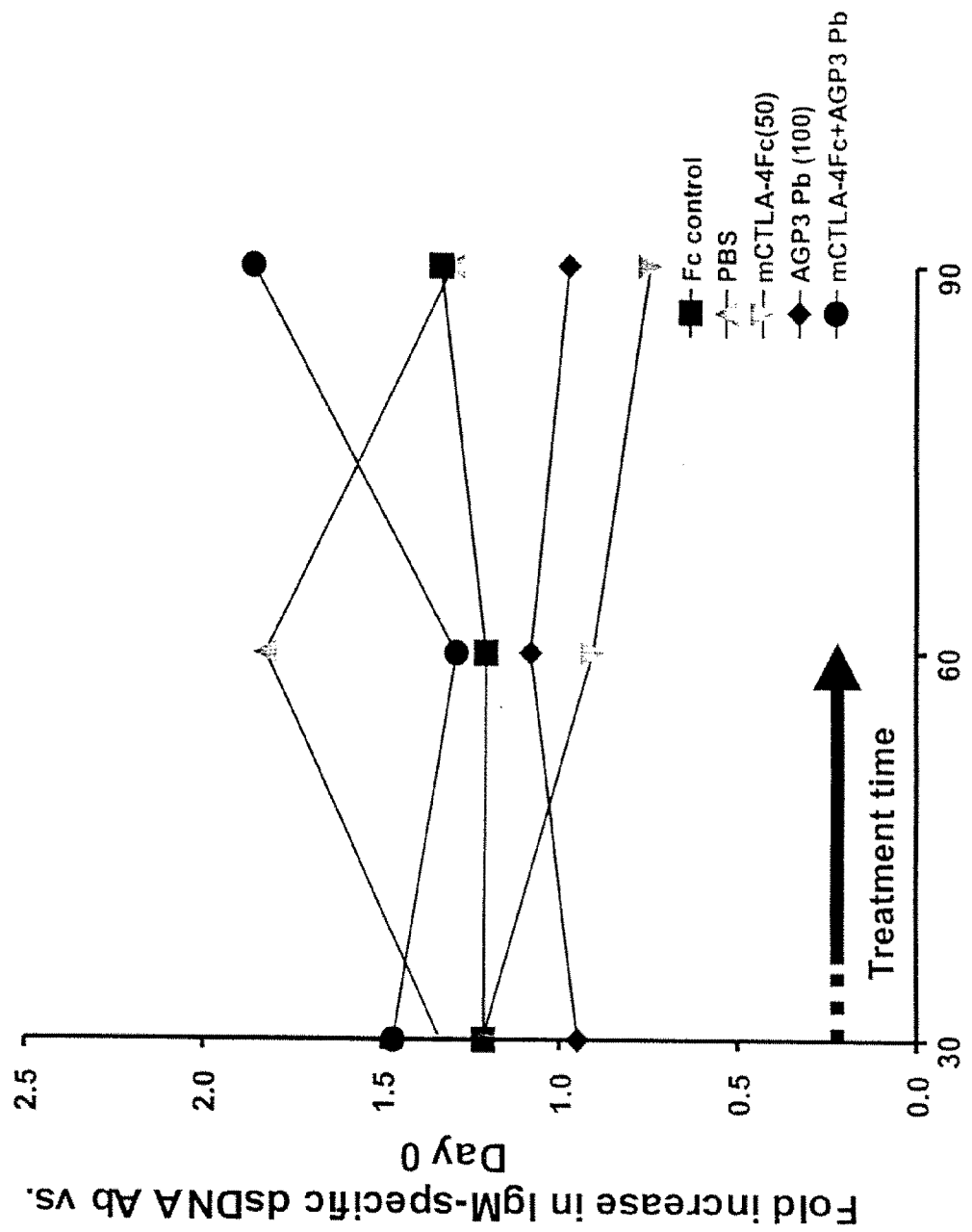
FIG. 11 shows the change in levels of IgM specific double-stranded DNA in serum collected at 30, 60 and 90 days after initial treatment with either AGP3 Pb (an AGP3 tandem dimer peptide-Fc fusion), murine CTLA4-Fc or the combination thereof. The levels of dsDNA and change in dsDNA antibody level was determined as described in FIG. 10 except IgM specific dsDNA was detected.

The level of double-stranded DNA specific antibodies as measured by anti-IgM antibodies is shown in FIG. 11.

Example 5

Combination Therapy Using PEG sTNFR-1 and AGP3 Pb in Arthritis-Susceptible B10.RIII Mice PEG sTNFR-1 2.6D, AGP3 Pb (an AGP3 tandem dimer peptide-Fc fusion), and Fc used in the study were produced at Amgen. Exemplary PEG sTNFR-1 2.6D production is described in Example 2. Exemplary AGP3 Pb production is described in Example 4.

Therapy in Mice

Arthritis was induced in B10.RIII mice by injection with porcine type II collagen as described in Example 1.

Prior to the injections, AGP3 Pb was suspended in PBS and sTNFR-1 2.6D was suspended in PBS. Mice were administered by injection of 100 μg of PEG sTNFR-I 2.6D, 100 μg AGP3 Pb, or 100 μg each of PEG sTNFR-1 2.6D and AGP3 Pb at day 0, +1, +2, +4, +6, +8 and +10 post clinical onset of disease. 100 μg is equivalent to 5 mg of therapeutic per Kg weight of animal (5 mg/Kg). Mice were injected in 100 μl volumes. PBS and human IgG1 Fc (Protein Science, Amgen, Thousand Oaks, Calif.) were used as controls. Mice were evaluated once a day for a mean arthritic score as described in Example 1.

Figure 12:
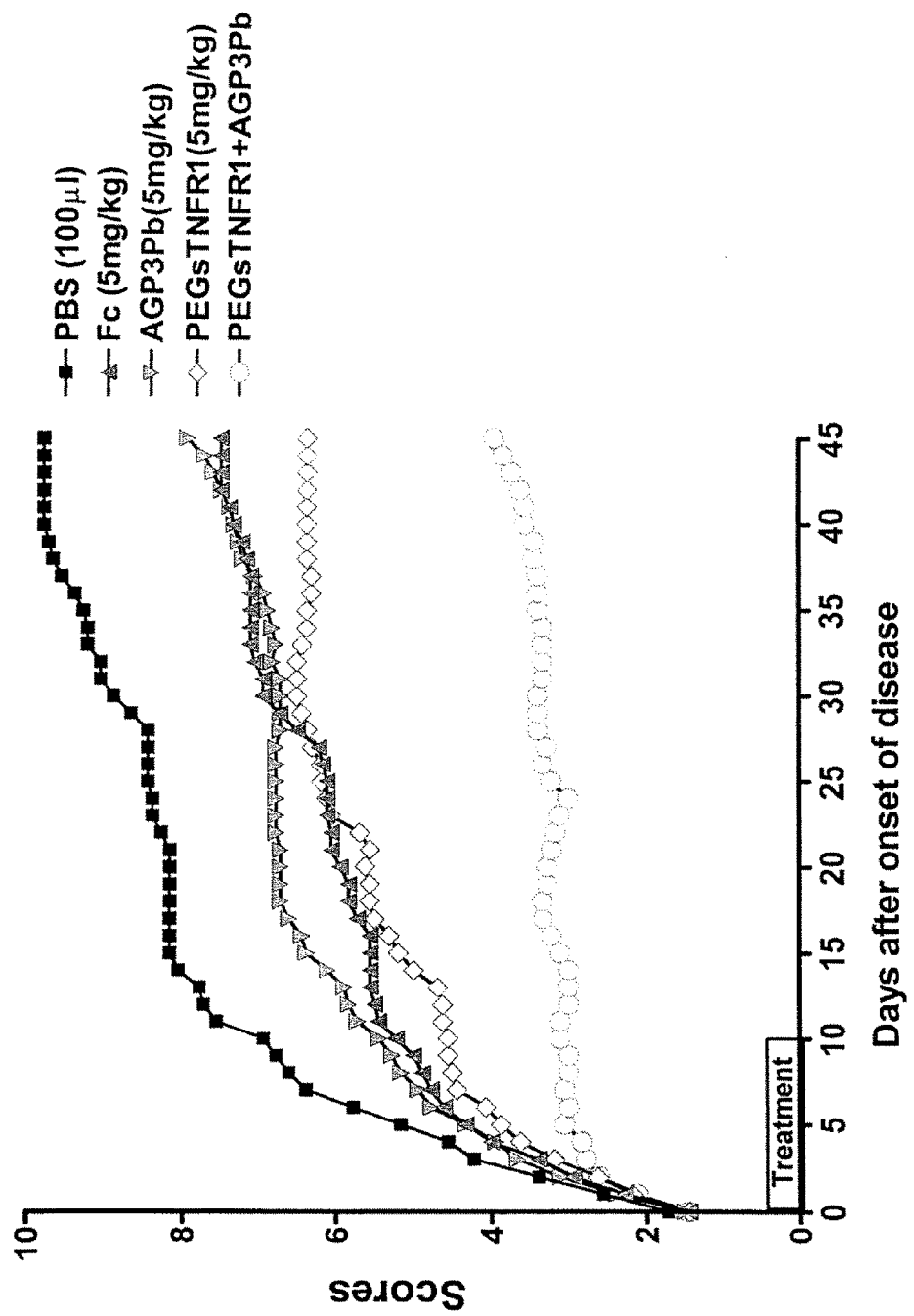
FIG. 12 shows mean arthritis scores in CIA animals during and after treatment with a TNF-alpha inhibitor (PEG sTNFR-1 2.6D), AGP3 Pb (an AGP3 tandem dimer peptide-Fc fusion), and a combination thereof. The animals were administered by injection of 100 μg of PEG sTNFR-1 2.6D, 100 μg AGP3 Pb, or 100 μg each of PEG sTNFR-1 2.6D and AGP3 Pb at day 0, +1, +2, +4, +6, +8 and +10 post onset of disease. 100 μg is equivalent to 5 mg of therapeutic per Kg weight of animal (5 mg/Kg). Phosphate buffered saline (PBS) and Fc were used as controls.

The combination of PEG sTNFR-1 2.6D and AGP3 Pb reduced collagen-induced arthritis for an extended period of time compared to Fc control, PEG sTNFR-1 2.6D alone, and AGP3 Pb alone, as shown in FIG. 12.

Example 6

Combination Therapy Using AGP3 Pb and KIN2 in Arthritis-Susceptible B10.RIII Mice AGP3 Pb (an AGP3 tandem dimer peptide-Fc fusion) and KIN2 used in the study were produced at Amgen. Exemplary KIN2 production is described in Example 1. Exemplary AGP3 Pb production is described in Example 4.

Therapy in Mice

Arthritis was induced in B10.RIII mice by injection with porcine type II collagen as described in Example 1.

Prior to injections, KIN2 was suspended in A5S and AGP3 Pb was suspended in PBS. Mice were treated by injection of 100 μg of KIN2, 100 μg AGP3 Pb, or 100 μg each of KIN2 and AGP3 Pb at day 0, +1, +2, +4, +6, +8 and +10 post clinical onset of disease. 100 μg is equivalent to 5 mg of therapeutic per Kg weight of animal (5 mg/Kg). Mice were injected in 100 μl volumes, except in the combination experiment, wherein the mice received two separate injections of 100 μl each. Injections of PBS and Fc were used as controls. Mice were monitored once every day and a mean arthritis score was calculated as described in Example 1.

Figure 13:
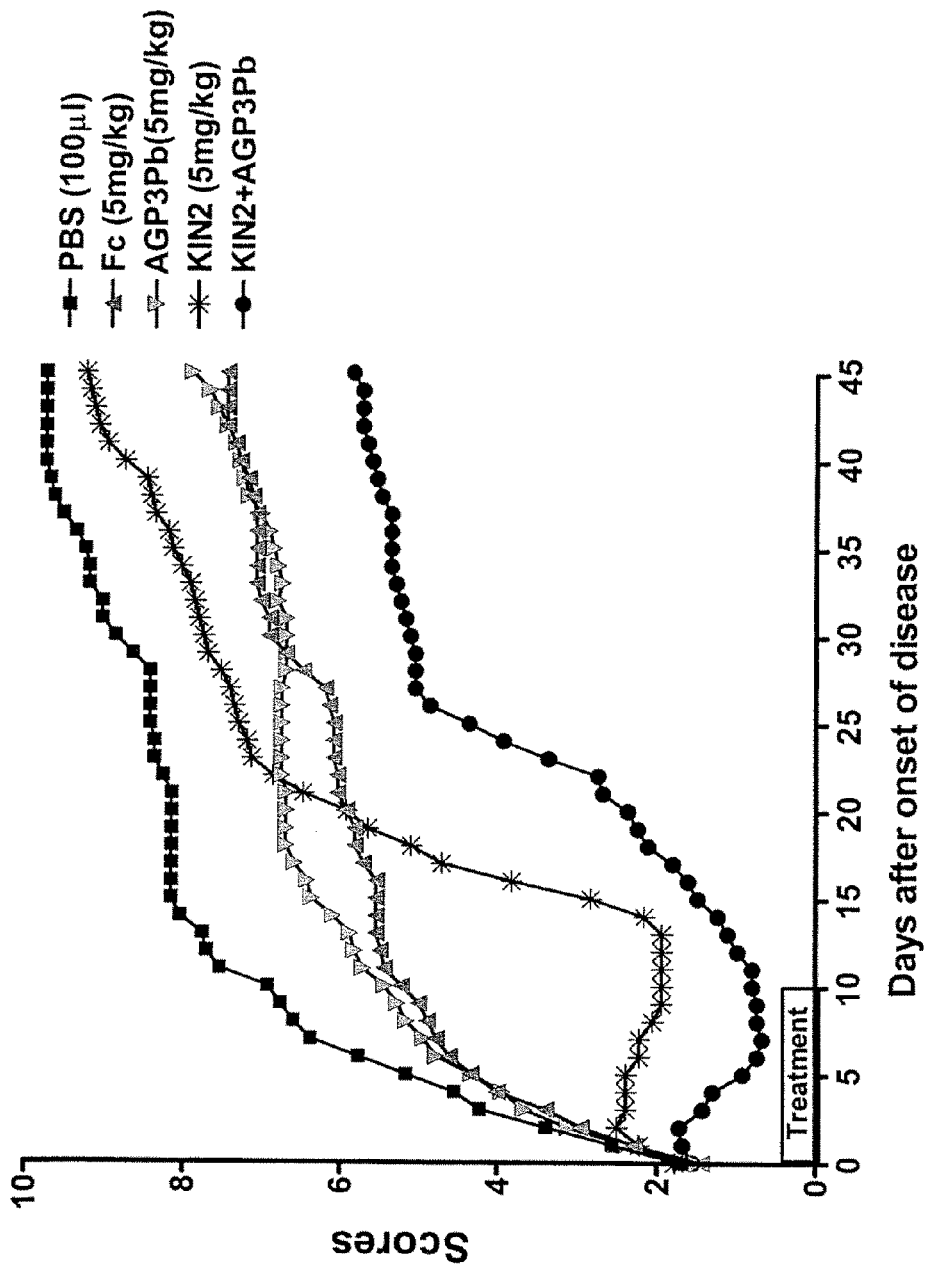
FIG. 13 shows mean arthritis scores in CIA animals during and after treatment with an IL-1 inhibitor (KIN2), AGP3 Pb (an AGP3 tandem dimer peptide-Fc fusion), and a combination thereof. The animals were administered by injection of 100 μg of KIN2, 100 μg AGP3 Pb, or 100 μg each of KIN2 and AGP3 Pb at day 0, +1, +2, +4, +6, +8 and +10 post onset of disease. 100 μg is equivalent to 5 mg of therapeutic per Kg weight of animal (5 mg/Kg). Phosphate buffered saline (PBS) and Fc were used as controls.

KIN2 reduced the severity of collagen-induced arthritis in mice when given alone, whereas AGP3 Pb given alone had a minimal effect when compared to PBS control. The combination of KIN2 and AGP3 Pb reduced collagen-induced arthritis for an extended period of time compared to KIN2 alone, as shown in FIG. 13.

Example 7

Combination Therapy Using KIN2 and Anti-OX40L Antibody in Arthritis-Susceptible DBA/1 Mice KIN2 used in the study was produced at Amgen. Exemplary KIN2 production is described in Example 1. Anti-OX40L antibody (RM134L) used in the study was purchased from Pharmingen (San Diego, Calif.). Exemplary generation of anti-OX40L antibody is summarized by Akiba et al., (J Immunol, 1999, 162: 7058-7066). Rat IgG was purchased from Sigma (St. Louis, Mo.).

Therapy in Mice

DBA/1 mice were immunized with bovine type II collagen emulsified with 1× complete Freunds adjuvant. Three weeks later, non-arthritic mice were boosted with bovine type II collagen emulsified with incomplete Freunds adjuvant. Mice were monitored for the development of arthritis as described in Example 1.

Prior to injections, KIN2 was suspended in A5S and anti-OX40L antibody was suspended in PBS. Mice were treated by injection of 100 μg of KIN2, 100 μg anti-OX40L antibody, or 100 μg each of KIN2 and anti-OX40L antibody, or 100 μg each of KIN2 and anti-OX40L antibody at day 0, +1, +2, +4, +6, +8 and +10 post clinical onset of disease. 100 μg is equivalent to 5 mg of therapeutic per Kg weight of animal (5 mg/Kg). Mice were injected in 100 μl volumes, except in the combination experiments, wherein the mice received two separate injections of 100 μl each. Injections of PBS and Rat IgG were used as controls. Mice were monitored once every day and a mean arthritis score was calculated as described in Example 1.

Figure 14:
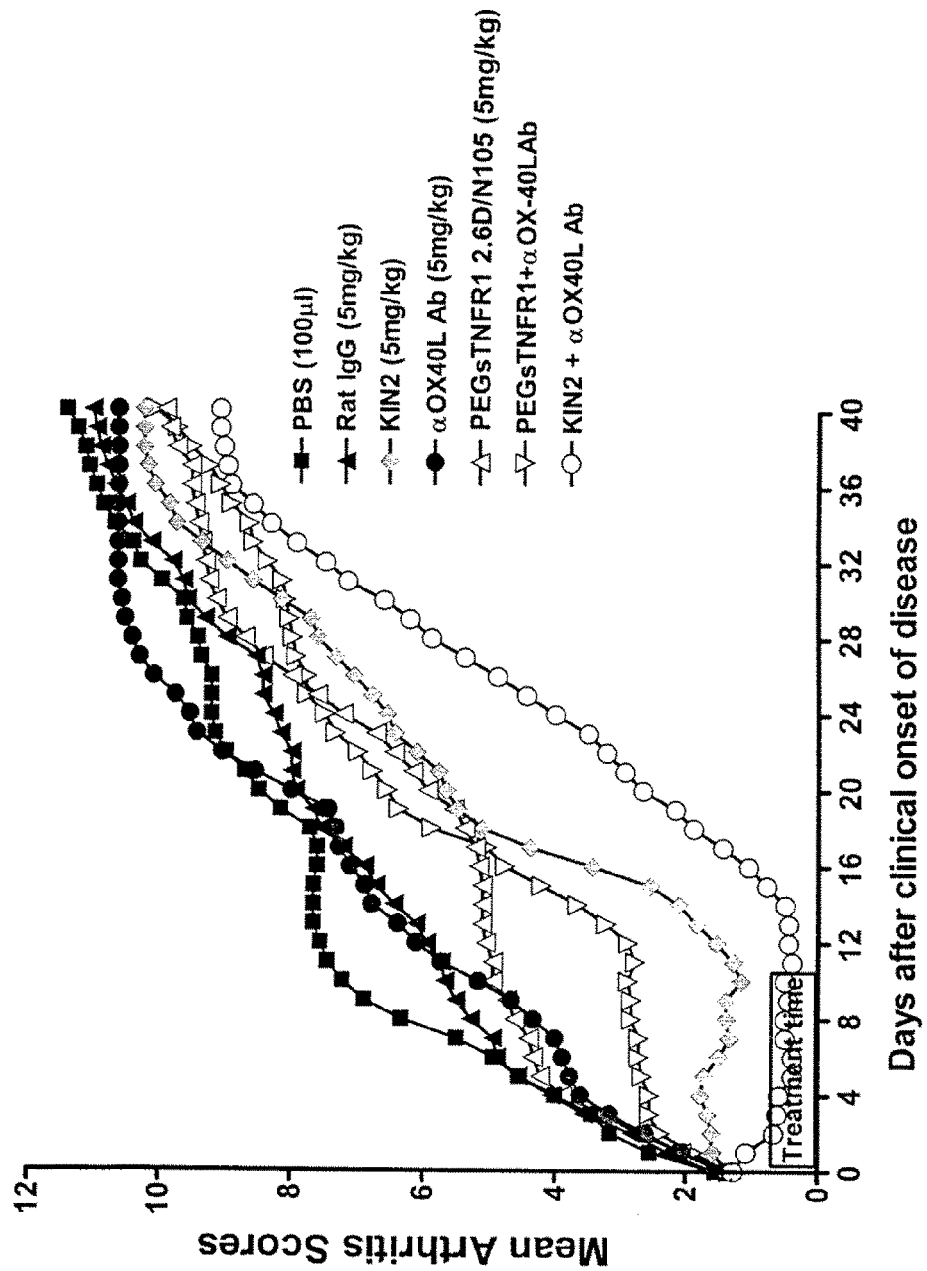
FIG. 14 shows mean arthritis scores in CIA animals during and after treatment with KIN2, PEG sTNFR-1 2.6D, anti-OX40L antibody, a combination of anti-OX40L antibody and KIN2, and a combination of anti-OX40L antibody and PEG sTNFR-1 2.6D. The animals were administered by injection of 100 μg of KIN2, 100 μg of PEG sTNFR-1 2.6D, 100 μg anti-OX40L antibody, 100 μg each of KIN2 and anti-OX40L antibody, or 100 μg each of PEG sTNFR-1 2.6D and anti-OX40L antibody at day 0, +1, +2, +4, +6, +8 and +10 post onset of disease. 100 μg is equivalent to 5 mg of therapeutic per Kg weight of animal (5 mg/Kg). Phosphate buffered saline (PBS) and Rat IgG were used as controls.

KIN2 reduced the severity of collagen-induced arthritis in mice when given alone, whereas anti-OX40L antibody given alone had a minimal effect when compared to PBS control. The combination of KIN2 and anti-OX40L antibody reduced collagen-induced arthritis for an extended period of time compared to KIN2 alone, as shown in FIG. 14.

Example 8

Combination Therapy Using PEG sTNFR-1 and Anti-OX40L Antibody in Arthritis-Susceptible DBA/1 Mice PEG sTNFR-1 2.6D and Fc used in the study were produced at Amgen. Exemplary PEG sTNFR-1 2.6D production is described in Example 2. Anti-OX40L antibody was purchased from Pharmingen. Rat IgG was purchased from Sigma.

Therapy in Mice

Arthritis was induced in DBA/1 mice by injection with bovine type II collagen as described in Example 7.

Prior to injections, anti-OX40L antibody was suspended in PBS and PEG sTNFR-1 2.6D was suspended in PBS. Mice were administered by injection of 100 µg PEG sTNFR-1 2.6D, 100 µg anti-OX40L antibody, or 100 µg each of PEG sTNFR-1 2.6D and anti-OX40L antibody at day 0, +1, +2, +4, +6, +8 and +10 post clinical onset of disease. 100 µg is equivalent to 5 mg of therapeutic per Kg weight of animal (5 mg/Kg). Mice were injected in 100 µl volumes. Injections of PBS and Rat IgG were used as controls. Mice were evaluated once a day for a mean arthritic score as described in Example 1.

PEG sTNFR-1 2.6D reduced the severity of collagen-induced arthritis in mice when given alone, whereas anti-OX40L antibody given alone had a minimal effect when compared to PBS control. The combination of PEG sTNFR-1 2.6D and anti-OX40L antibody reduced collagen-induced arthritis for an extended period of time compared to PEG sTNFR-1 2.6D alone, as shown in FIG. 14.

Example 9

Combination Therapy Using AGP3 Pb and CTLA4-Fc in Mice Having Greater than 100 mg/dl Protein in the Urine CTLA4-Fc protein and AGP3 Pb (an AGP3 tandem dimer peptide-Fc fusion) used in this study were produced at Amgen. Exemplary AGP3 Pb production is described in Example 4.

Therapy in Mice (NZB×NZW) F1 mice were allowed to develop lupus-like symptoms as described in Example 4.

Figure 15:
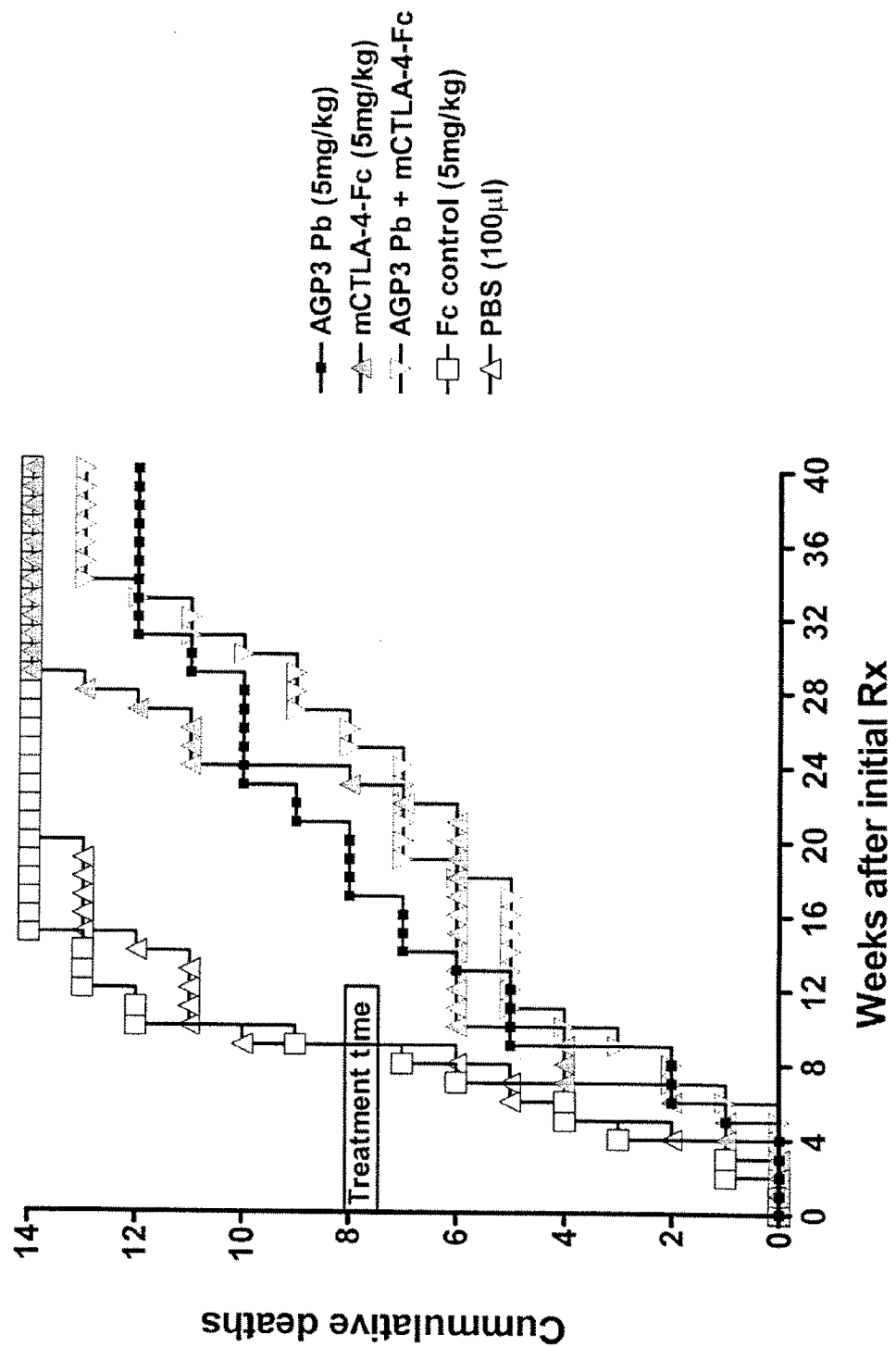
FIG. 15 shows percent survival of six month old (NZBx-NZW) F1 mice prescreened for greater than 100 mg/dl protein in the urine. The prescreened mice were injected three times per week for 12 weeks with 100 μg of AGP3 Pb (an AGP3 tandem dimer peptide-Fc fusion), 50 μg of murine CTLA4-Fc, or a combination of 100 μg of AGP3 Pb and 50 μg of murine CTLA4-Fc. 100 μg is equivalent to 4 mg of therapeutic per Kg weight of animal (4 mg/Kg). 50 μg is equivalent to 2 mg of therapeutic per Kg weight of animal (2 mg/Kg). Fc and PBS were used as controls.

Prior to treatment, mice were pre-screened for protein in the urine with Albustix® reagent strips (Bayer Corp., Elkhart, Ind.), and those having greater than 100 mg/dl of protein in the urine were included in the experiment. Prior to the injections, murine CTLA4-Fc was suspended in PBS and AGP3 Pb was suspended in PBS. Six month old (NZB×NZW) F1 mice were treated intraperitoneally 3 times per week for 12 weeks with 100 µg (4 mg/kg) AGP3 Pb, 50 µg (2 mg/kg) murine CTLA4-Fc, or a combination of 100 µg (4 mg/kg) AGP3 Pb and 50 µg (2 mg/kg) murine CTLA4-Fc. 100 µg is equivalent to 4 mg of therapeutic per Kg weight of animal (4 mg/Kg). 50 µg is equivalent to 2 mg of therapeutic per Kg weight of animal (2 mg/Kg). 100 µg of human IgG1 Fc protein or 100 µl PBS were administered as controls. Protein in the urine was evaluated weekly throughout the life of the experiment using Albustix® reagent strips (Bayer Corp., Elkhart, Ind.). The combination of AGP3 Pb and murine CTLA4-Fc showed a marked improvement in survival compared to AGP3 Pb or murine CTLA4-Fc alone, as shown in FIG. 15.

The selected mice in the treatment groups were assayed for proteinuria every week using Albustix® reagent strips (Bayer Corp., Elkhart, Ind.). Each week, the mice were given a score of +1 if their proteinuria became worse (from >100 mg/dl to >300 mg/di), a score of 0 if their proteinuria stayed the same, and a score of −1 if their proteinuria improved (<100 mg/dl). The mean score for the group of 14 mice is graphed in FIG. 16.

Figure 16:
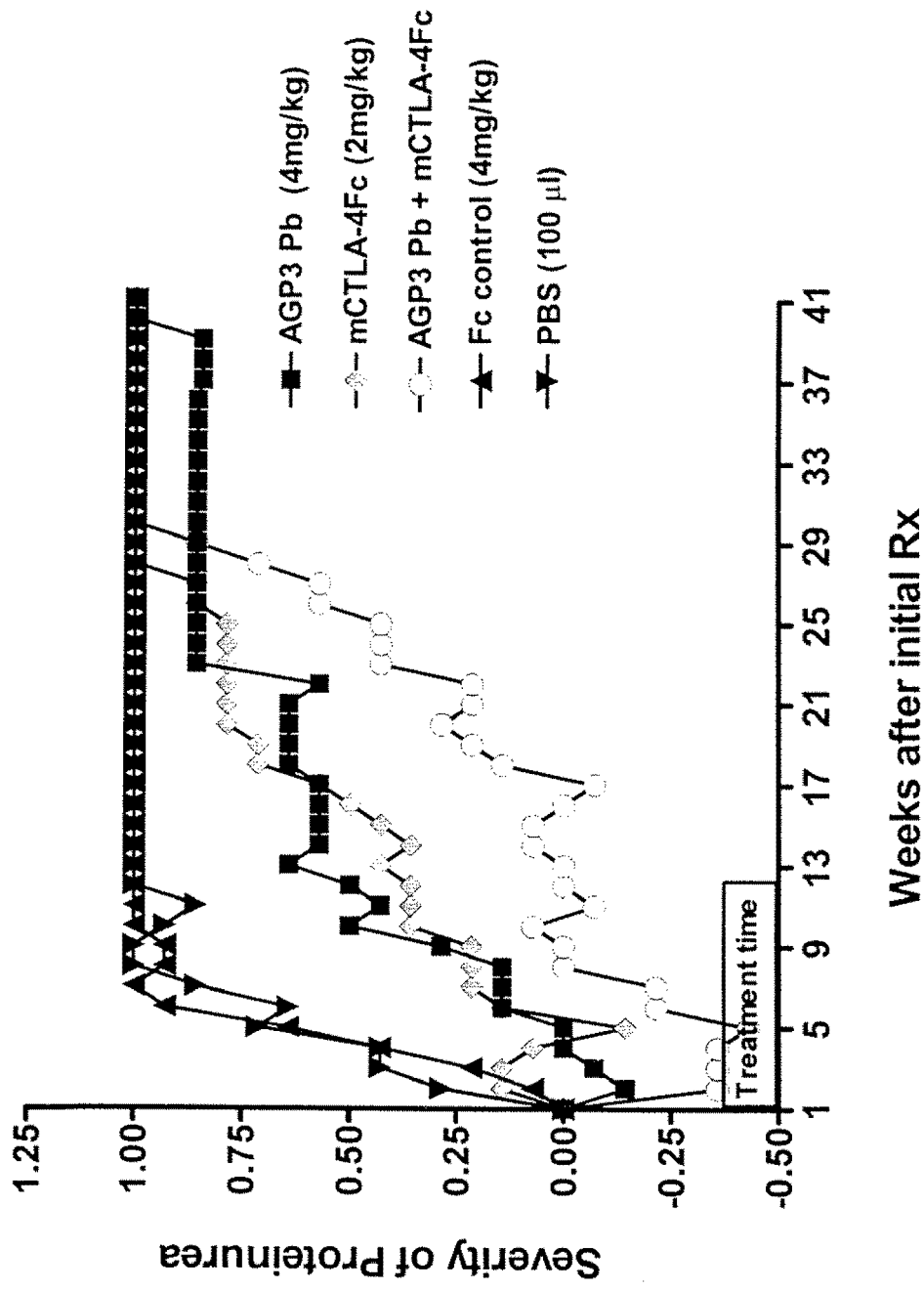
FIG. 16 shows the severity of proteinuria in (NZBxNZW) F1 mice prescreened for greater than 100 mg/dl protein in the urine. The prescreened mice were injected three times per week for 12 weeks with 100 μg of AGP3 Pb (an AGP3 tandem dimer peptide-Fc fusion), 50 μg of murine CTLA4-Fc, or a combination of 100 μg of AGP3 Pb and 50 μg of murine CTLA4-Fc. 100 μg is equivalent to 4 mg of therapeutic per Kg weight of animal (4 mg/Kg). 50 μg is equivalent to 2 mg of therapeutic per Kg weight of animal (2 mg/Kg). Fc and PBS were used as controls. The mice were tested for proteinuria every week using Albustix® commercial assay (Bayer AG).

FIG. 16 shows the severity of proteinuria over the course of 41 weeks. The combination treatment of AGP3 Pb and murine CTLA4-Fc reduced the severity of proteinuria compared to administration of AGP3 Pb or murine CTLA4-Fc alone, as shown in FIG. 16.

Example 10

Combination Therapy Using AGP3 Pb and CTLA4-Fc in Mice Having Greater than 300 mg/dl Protein in the Urine CTLA4-Fc protein and AGP3 Pb (an AGP3 tandem dimer peptide-Fc fusion) were produced at Amgen. AGP3 Pb production is described in Example 4.

Therapy in Mice (NZB×NZW) F1 mice were allowed to develop lupus-like symptoms as described in Example 4.

Figure 17:
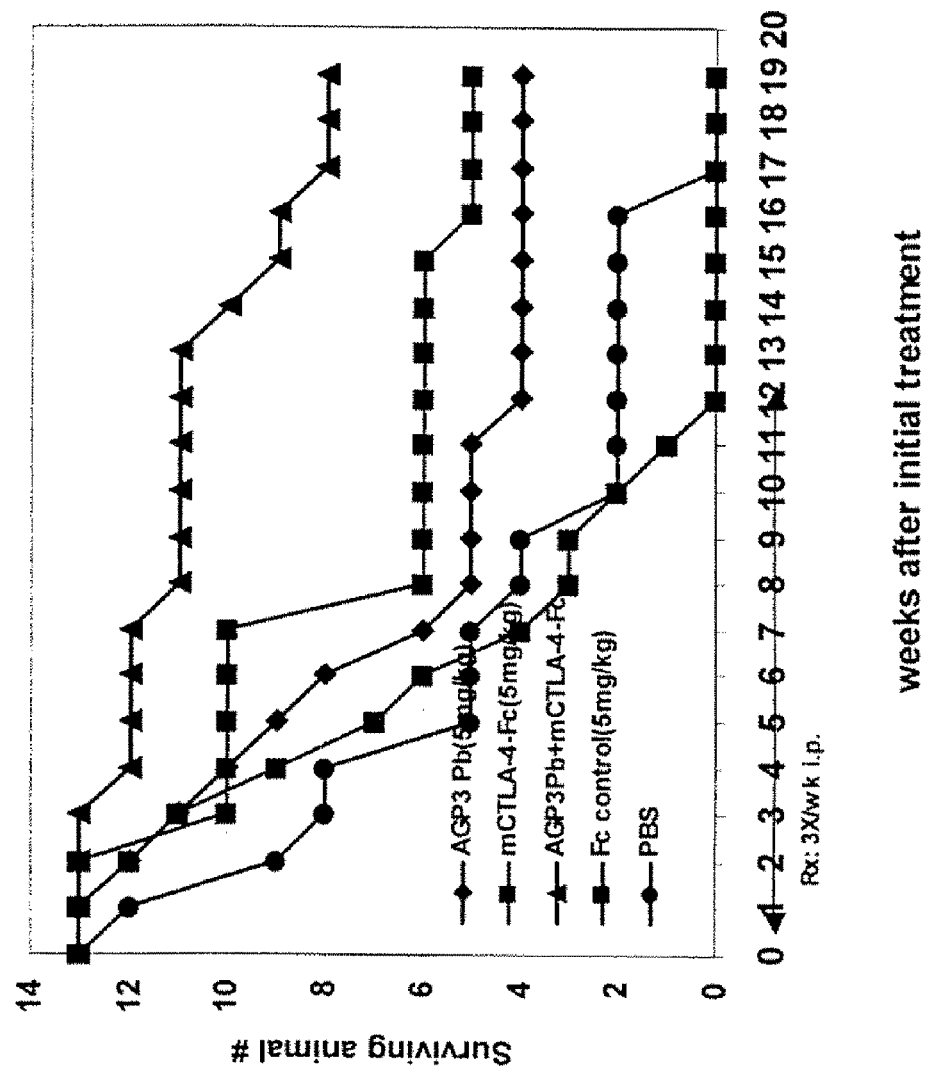
FIG. 17 shows percent survival of (NZBxNZW) F1 mice prescreened for greater than 300 mg/dl protein in the urine. The prescreened mice were injected three times per week for twelve weeks with 100 μg of AGP3 Pb (an AGP3 tandem dimer peptide-Fc fusion), 50 μg of murine CTLA4-Fc, or a combination of 100 μg of AGP3 Pb and 50 μg of murine CTLA4-Fc. 100 μg is equivalent to 4 mg of therapeutic per Kg weight of animal (4 mg/Kg). 50 μg is equivalent to 2 mg of therapeutic per Kg weight of animal (2 mg/Kg). Fc and PBS were used as controls.

Prior to treatment, mice were pre-screened for protein in the urine with Albustix® reagent strips (Bayer Corp., Elkhart, Ind.), and those having greater than 300 mg/dl of protein in the urine were included in the experiment. Prior to the injections, murine CTLA4-Fc was suspended in PBS and AGP3 Pb was suspended in PBS. Six month old (NZB×NZW) F1 mice were treated intraperitoneally 3 times per week for 12 weeks with 100 µg (4 mg/kg) AGP3 Pb, 50 µg (2 mg/kg) murine CTLA4-Fc, or a combination of 100 µg (4 mg/kg) AGP3 Pb and 50 µg (2 mg/kg) murine CTLA4-Fc. 100 µg is equivalent to 4 mg of therapeutic per Kg weight of animal (4 mg/Kg). 50 µg is equivalent to 2 mg of therapeutic per Kg weight of animal (2 mg/Kg). 100 µg of human IgG1 Fc protein or 100 µl PBS were administered as controls. Protein in the urine was evaluated weekly throughout the life of the experiment using Albustix® reagent strips (Bayer Corp., Elkhart, Ind.). The combination of AGP3 Pb and murine CTLA4-Fc showed a marked improvement in survival compared to AGP3 Pb or murine CTLA4-Fc alone, as shown in FIG. 17.

The selected mice in the treatment groups were assayed for proteinuria every week using Albustix® reagent strips (Bayer Corp., Elkhart, Ind.). Each week, the mice were given a score of +2 if they died, a score of +1 if their proteinuria worsened (>2000 mg/dl), a score of 0 if their proteinuria stayed the same (300 mg/dl to 2000 mg/dl), a score of −1 if their proteinuria improved (<300 mg/dl to 100 mg/dl), and a score of −2 if their proteinuria improved dramatically (<100 mg/dl). The mean score for the group of 13 mice is graphed in FIG. 18.

Figure 18:
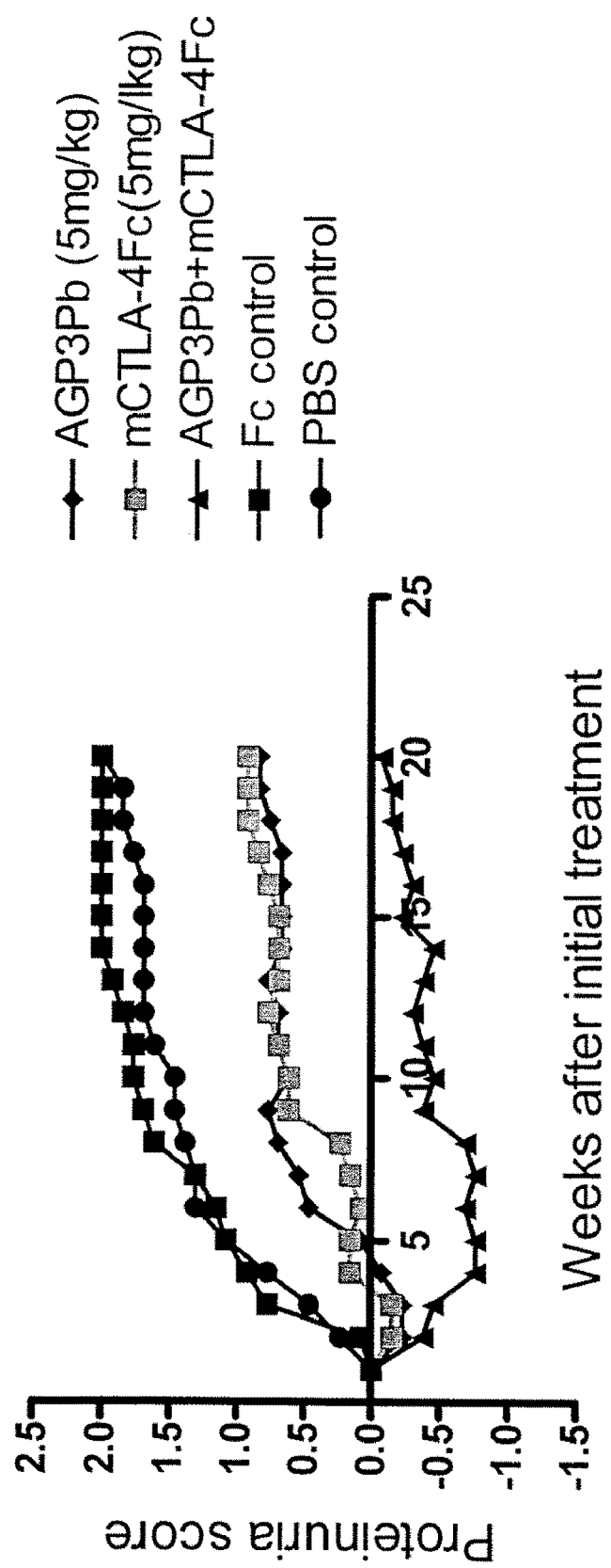
FIG. 18 shows the severity of proteinuria in (NZBxNZW) F1 mice prescreened for greater than 300 mg/dl protein in the urine. The prescreened mice were injected three times per week for 36 weeks with 100 μg of AGP3 Pb (an AGP3 tandem dimer peptide-Fc fusion), 50 μg of murine CTLA4-Fc, or a combination of 100 μg of AGP3 Pb and 50 μg of murine CTLA4-Fc. 100 μg is equivalent to 4 mg of therapeutic per Kg weight of animal (4 mg/Kg). 50 μg is equivalent to 2 mg of therapeutic per Kg weight of animal (2 mg/Kg). Fc and PBS were used as controls. The mice were tested for proteinuria every week using Albustix® commercial assay (Bayer AG).

FIG. 18 shows the severity of proteinuria over the course of 20 weeks. The combination treatment of AGP3 Pb and murine CTLA4-Fc reduced the severity of proteinuria compared to administration of AGP3 Pb or murine CTLA4-Fc alone, as shown in FIG. 18.

Example 11

Intermittent Combination Therapy Using CTLA4-Fc and KIN2 in Arthritis-Susceptible B10.RIII Mice The following is a prophetic example wherein intermittent treatment with the combination of KIN2 and CTLA4-Fc reduces collagen-induced arthritis for an extended period of time compared to CTLA4-Fc alone and KIN2 alone.

Therapy in Mice

Arthritis is induced in B10.RIII mice by injection with porcine type II collagen as described in Example 1.

The mice are separated into two groups. In the first group, prior to injection, KIN2 is suspended in A5S and CTLA4-Fc is suspended in PBS. The mice are administered by injection of 100 µg of KIN2, 100 µg CTLA4-Fc, or 100 µg each of KIN2 and CTLA4-Fc at days 0 to +9 post clinical onset of disease. 100 µg is equivalent to 5 mg of therapeutic per Kg weight of animal (5 mg/Kg). Mice are injected in 100 µl volumes, except in the combination experiment, wherein the mice receive two separate injections of 100 µl each. Injections of PBS and Fc are used as controls. Mice are monitored once every day and a mean arthritis score is calculated as described in Example 1.

Those mice that score above 1 on the mean arthritis score are treated a second time by injection of 100 µg of KIN2, 100 µg CTLA4-Fc, or 100 µg each of KIN2 and CTLA4-Fc for three additional days. After the second treatment, the three day treatment is repeated whenever a mouse has a mean arthritis score above 1. The treatment is repeated as often as necessary during the course of the experiment.

In the second group, prior to injection, KIN2 is suspended in A5S and CTLA4-Fc is suspended in PBS. The mice are treated by injection of 100 µg of KIN2, 100 µg CTLA4-Fc, or 100 µg each of KIN2 and CTLA4-Fc at days 0 to +2 post clinical onset of disease. 100 µg is equivalent to 5 mg of therapeutic per Kg weight of animal (5 mg/Kg). Mice are injected in 100 µl volumes, except in the combination experiment, wherein the mice receive two separate injections of 100 µl each. Injections of PBS and Fc are used as controls. Following treatment mice are evaluated daily and given a mean arthritis score as described in Example 1.

Those mice that score above 1 on the mean arthritis score are treated a second time by injection of a maintenance dose of 100 µg of KIN2, 100 µg CTLA4-Fc, or 100 µg each of KIN2 and CTLA4-Fc for three additional days. After the second treatment, the three day maintenance dose treatment is repeated whenever a mouse has a mean arthritis score above 1. The maintenance dose treatment is repeated as often as necessary during the course of the experiment. The experiment continues for two months.

Example 12

Intermittent Combination Therapy Using CTLA4-Fc and PEG sTNFR-1 in Arthritis-Susceptible B10.RIII Mice The following is a prophetic example wherein intermittent treatment with the combination of PEG sTNFR-1 2.6D and CTLA4-Fc reduces collagen-induced arthritis for an extended period of time compared to CTLA4-Fc alone and PEG sTNFR-1 2.6D alone.

Therapy in Mice

Arthritis is induced in B10.RIII mice by injection with porcine type II collagen as described in Example 1.

The mice are separated into two groups. In the first group, prior to injection, PEG sTNFR-1 2.6D is suspended in PBS and CTLA4-Fc is suspended in PBS. The mice are treated by injection of 100 µg of PEG sTNFR-1 2.6D, 100 µg CTLA4-Fc, or 100 µg each of PEG sTNFR-1 2.6D and CTLA4-Fc at days 0 to +9 post clinical onset of disease. 100 µg is equivalent to 5 mg of therapeutic per Kg weight of animal (5 mg/Kg). Mice are injected in 100 µl volumes. Injections of PBS and Fc are used as controls. Mice are monitored once every day and a mean arthritis score is calculated as described in Example 1.

Those mice that score above 1 on the mean arthritis score are treated a second time by injection of a maintenance dose of 100 µg of PEG sTNFR-1 2.6D, 100 µg CTLA4-Fc, or 100 µg each of PEG sTNFR-1 2.6D and CTLA4-Fc for three additional days. After the second treatment, the three day maintenance dose treatment is repeated whenever a mouse has a mean arthritis score above 1. The maintenance dose treatment is repeated as often as necessary during the course of the experiment.

In the second group, prior to injection, PEG sTNFR-1 2.6D is suspended in PBS and CTLA4-Fc is suspended in PBS. The mice are treated by injection of 100 µg of PEG sTNFR-1 2.6D, 100 µg CTLA4-Fc, or 100 µg each of PEG sTNFR-1 2.6D and CTLA4-Fc at days 0 to +2 post clinical onset of disease. 100 µg is equivalent to 5 mg of therapeutic per Kg weight of animal (5 mg/Kg). Mice are injected in 100 µl volumes. Injections of PBS and Fc are used as controls. Mice are monitored once every day and a mean arthritis score is calculated as described in Example 1.

Those mice that score above 1 on the mean arthritis score are treated a second time by injection of a maintenance dose of 100 µg of PEG sTNFR-1 2.6D, 100 µg CTLA4-Fc, or 100 µg each of PEG sTNFR-1 2.6D and CTLA4-Fc for three additional days. After the second treatment, the three day maintenance dose treatment is repeated whenever a mouse has a mean arthritis score above 1. The maintenance dose treatment is repeated as often as necessary during the course of the experiment.

The experiment continues for two months.

Example 13

Combination Therapy Using Etanercept and CTLA4-Fc in Arthritis-Susceptible B10.RIII Mice The following is a prophetic example wherein treatment with the combination of Etanercept and CTLA4-Fc reduces collagen-induced arthritis for an extended period of time compared to CTLA4-Fc alone and Etanercept alone. Etanercept is sold commercially under the tradename Enbrel®.

Therapy in Mice

Arthritis is induced in B10.RIII mice by injection with porcine type II collagen as described in Example 1.

Prior to the injections, murine CTLA4-Fc is suspended in PBS and Etanercept is suspended in PBS. Mice are administered by injection of 100 µg of Etanercept, 100 µg murine CTLA4-Fc, or 100 µg each of Etanercept and murine CTLA4-FC at day 0, +1, +2, +4, +6, +8 and +10 post clinical onset of disease. 100 µg is equivalent to 5 mg of therapeutic per Kg weight of animal (5 mg/Kg). Mice are injected in 100 µl volumes. PBS and human IgG1 Fc (Protein Science, Amgen, Thousand Oaks, Calif.) are used as controls. Mice are evaluated once a day for a mean arthritic score as described in Example 1.

The experiment continues for 40 days after clinical onset of disease.

What is claimed is:

1. A method for treating an individual afflicted with rheumatoid arthritis, which comprises administering a therapeutically effective amount of an IL-1 inhibitor and an OX40 ligand inhibitor to the individual, wherein the IL-1 inhibitor comprises an IL-1ra polypeptide and the OX40 ligand inhibitor comprises an antibody that binds OX40 ligand.

2. The method of claim 1, wherein the IL-1 inhibitor comprises an IL-1ra polypeptide fused to a human immunoglobulin constant region.

3. The method of claim 1, wherein the IL-1 inhibitor comprises Fc IL-1ra.

4. The method of claim 1, wherein the IL-1 inhibitor comprises the amino acid sequence of SEQ ID NO 3.

5. The method of claim 1, wherein the IL-1 inhibitor comprises anakinra.

6. The method of claim 1, wherein the administering is discontinued for at least one day and then resumed.

7. The method of claim 6, wherein the administering is resumed to treat a recurrence of the rheumatoid arthritis.

8. The method of claim 2, wherein the administering is discontinued for at least one day and then resumed.

9. The method of claim 8, wherein the administering is resumed to treat a recurrence of the rheumatoid arthritis.

10. The method of claim 3, wherein the administering is discontinued for at least one day and then resumed.

11. The method of claim 10, wherein the administering is resumed to treat a recurrence of the rheumatoid arthritis.

12. The method of claim 4, wherein the administering is discontinued for at least one day and then resumed.

13. The method of claim 12, wherein the administering is resumed to treat a recurrence of the rheumatoid arthritis.

14. The method of claim 5, wherein the administering is discontinued for at least one day and then resumed.

15. The method of claim 14, wherein the administering is resumed to treat a recurrence of the rheumatoid arthritis.

* * * * *

SEQUENCE LISTING

<160> NUMBER OF SEQ ID NOS: 28

<210> SEQ ID NO 1
<211> LENGTH: 293
<212> TYPE: PRT
<213> ORGANISM: Artificial Sequence -continued

```
<220> FEATURE:
<223> OTHER INFORMATION: AGP-3 Peptibody amino acid sequence

<400> SEQUENCE: 1

Met Leu Pro Gly Cys Lys Trp Asp Leu Leu Ile Lys Gln Trp Val Cys
1               5                   10                  15

Asp Pro Leu Gly Ser Gly Ser Ala Thr Gly Gly Ser Gly Ser Thr Ala
            20                  25                  30

Ser Ser Gly Ser Gly Ser Ala Thr His Met Leu Pro Gly Cys Lys Trp
        35                  40                  45

Asp Leu Leu Ile Lys Gln Trp Val Cys Asp Pro Leu Gly Gly Gly Gly
    50                  55                  60

Gly Val Asp Lys Thr His Thr Cys Pro Pro Cys Pro Ala Pro Glu Leu
65                  70                  75                  80

Leu Gly Gly Pro Ser Val Phe Leu Phe Pro Pro Lys Pro Lys Asp Thr
                85                  90                  95

Leu Met Ile Ser Arg Thr Pro Glu Val Thr Cys Val Val Val Asp Val
            100                 105                 110

Ser His Glu Asp Pro Glu Val Lys Phe Asn Trp Tyr Val Asp Gly Val
        115                 120                 125

Glu Val His Asn Ala Lys Thr Lys Pro Arg Glu Glu Gln Tyr Asn Ser
    130                 135                 140

Thr Tyr Arg Val Val Ser Val Leu Thr Val Leu His Gln Asp Trp Leu
145                 150                 155                 160

Asn Gly Lys Glu Tyr Lys Cys Lys Val Ser Asn Lys Ala Leu Pro Ala
                165                 170                 175

Pro Ile Glu Lys Thr Ile Ser Lys Ala Lys Gly Gln Pro Arg Glu Pro
            180                 185                 190

Gln Val Tyr Thr Leu Pro Pro Ser Arg Asp Glu Leu Thr Lys Asn Gln
        195                 200                 205

Val Ser Leu Thr Cys Leu Val Lys Gly Phe Tyr Pro Ser Asp Ile Ala
    210                 215                 220

Val Glu Trp Glu Ser Asn Gly Gln Pro Glu Asn Asn Tyr Lys Thr Thr
225                 230                 235                 240

Pro Pro Val Leu Asp Ser Asp Gly Ser Phe Phe Leu Tyr Ser Lys Leu
                245                 250                 255

Thr Val Asp Lys Ser Arg Trp Gln Gln Gly Asn Val Phe Ser Cys Ser
            260                 265                 270

Val Met His Glu Ala Leu His Asn His Tyr Thr Gln Lys Ser Leu Ser
        275                 280                 285

Leu Ser Pro Gly Lys
    290

<210> SEQ ID NO 2
<211> LENGTH: 186
<212> TYPE: PRT
<213> ORGANISM: Homo sapiens

<400> SEQUENCE: 2

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45
```

```
Ala Ala Thr Tyr Met Met Gly Asn Glu Leu Thr Phe Leu Asp Asp Ser
 50                  55                  60

Ile Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp Phe Leu Leu Trp
            115                 120                 125

Ile Leu Ala Ala Val Ser Ser Gly Leu Phe Phe Tyr Ser Phe Leu Leu
        130                 135                 140

Thr Ala Val Ser Leu Ser Lys Met Leu Lys Lys Arg Ser Pro Leu Thr
145                 150                 155                 160

Thr Gly Val Tyr Val Lys Met Pro Pro Thr Glu Pro Glu Cys Glu Lys
                165                 170                 175

Gln Phe Gln Pro Tyr Phe Ile Pro Ile Asn
                180                 185

<210> SEQ ID NO 3
<211> LENGTH: 388
<212> TYPE: PRT
<213> ORGANISM: Artificial Sequence
<220> FEATURE:
<223> OTHER INFORMATION: IL-1 inhibitor (KIN2) (FcIL-1ra) amino acid
      sequence

<400> SEQUENCE: 3

Met Arg Pro Ser Gly Arg Lys Ser Ser Lys Met Gln Ala Phe Arg Ile
 1               5                  10                  15

Trp Asp Val Asn Gln Lys Thr Phe Tyr Leu Arg Asn Asn Gln Leu Val
                 20                  25                  30

Ala Gly Tyr Leu Gln Gly Pro Asn Val Asn Leu Glu Glu Lys Ile Asp
             35                  40                  45

Val Val Pro Ile Glu Pro His Ala Leu Phe Leu Gly Ile His Gly Gly
         50                  55                  60

Lys Met Cys Leu Ser Cys Val Lys Ser Gly Asp Glu Thr Arg Leu Gln
 65                  70                  75                  80

Leu Glu Ala Val Asn Ile Thr Asp Leu Ser Glu Asn Arg Lys Gln Asp
                 85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
130                 135                 140

Thr Lys Phe Tyr Phe Gln Glu Asp Glu Ala Ala Ala Glu Pro Lys Ser
145                 150                 155                 160

Ser Asp Lys Thr His Thr Cys Pro Pro Cys Pro Ala Pro Glu Leu Leu
                165                 170                 175

Gly Gly Pro Ser Val Phe Leu Phe Pro Pro Lys Pro Lys Asp Thr Leu
            180                 185                 190

Met Ile Ser Arg Thr Pro Glu Val Thr Cys Val Val Val Asp Val Ser
        195                 200                 205

His Glu Asp Pro Glu Val Lys Phe Asn Trp Tyr Val Asp Gly Val Glu
210                 215                 220
```

Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
            245                 250                 255

Gly Lys Glu Tyr Lys Cys Lys Val Ser Asn Lys Ala Leu Pro Ala Pro
        260                 265                 270

Ile Glu Lys Thr Ile Ser Lys Ala Lys Gly Gln Pro Arg Glu Pro Gln
    275                 280                 285

Val Tyr Thr Leu Pro Pro Ser Arg Asp Glu Leu Thr Lys Asn Gln Val
290                 295                 300

Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
            325                 330                 335

Pro Val Leu Asp Ser Asp Gly Ser Phe Phe Leu Tyr Ser Lys Leu Thr
        340                 345                 350

Val Asp Lys Ser Arg Trp Gln Gln Gly Asn Val Phe Ser Cys Ser Val
    355                 360                 365

Met His Glu Ala Leu His Asn His Tyr Thr Gln Lys Ser Leu Ser Leu
370                 375                 380

Ser Pro Gly Lys
385

<210> SEQ ID NO 4
<211> LENGTH: 106
<212> TYPE: PRT
<213> ORGANISM: Artificial Sequence
<220> FEATURE:
<223> OTHER INFORMATION: s-TNFR-I amino acid sequence

<400> SEQUENCE: 4

Met Asp Ser Val Cys Pro Gln Gly Lys Tyr Ile His Pro Gln Asn Asn
1               5                   10                  15

Ser Ile Cys Cys Thr Lys Cys His Lys Gly Thr Tyr Leu Tyr Asn Asp
            20                  25                  30

Cys Pro Gly Pro Gly Gln Asp Thr Asp Cys Arg Glu Cys Glu Ser Gly
        35                  40                  45

Ser Phe Thr Ala Ser Glu Asn His Leu Arg His Cys Leu Ser Cys Ser
    50                  55                  60

Lys Cys Arg Lys Glu Met Gly Gln Val Glu Ile Ser Ser Cys Thr Val
65                  70                  75                  80

Asp Arg Asp Thr Val Cys Gly Cys Arg Lys Asn Gln Tyr Arg His Tyr
                85                  90                  95

Trp Ser Glu Asn Leu Phe Gln Cys Phe Asn
            100                 105

<210> SEQ ID NO 5
<211> LENGTH: 1167
<212> TYPE: DNA
<213> ORGANISM: Artificial Sequence
<220> FEATURE:
<223> OTHER INFORMATION: IL-1 inhibitor (KIN2 )(FcIL-1ra) nucleotide
      sequence

<400> SEQUENCE: 5
atgcgaccgt ccggccgtaa gagctccaaa atgcaggctt ccgtatctg ggacgttaac      60 cagaaaacct tctacctgcg caacaaccag ctggttgctg ctacctgca gggtccgaac     120 gttaacctgg aagaaaaaat cgacgttgta ccgatcgaac cgcacgctct gttcctgggt    180

-continued

```
atccacggtg gtaaaatgtg cctgagctgc gtgaaatctg gtgacgaaac tcgtctgcag      240
ctggaagcag ttaacatcac tgacctgagc gaaaaccgca acaggacaa  acgtttcgca      300 ttcatccgct ctgacagcgg cccgaccacc agcttcgaat ctgctgcttg cccgggttgg      360
ttcctgtgca ctgctatgga agctgaccag ccggtaagcc tgaccaacat gccgacgaa       420 ggcgtgatgg taaccaaatt ctacttccag gaagacgaag ctgcagctga accaaaatct      480
tccgacaaaa ctcacacatg cccaccgtgc ccagcacctg aactcctggg gggaccgtca      540
gtcttcctct tccccccaaa acccaaggac accctcatga tctcccggac ccctgaggtc      600
acatgcgtgg tggtggacgt gagccacgaa gaccctgagg tcaagttcaa ctggtacgtg      660
gacggcgtgg aggtgcataa tgccaagaca agccgcggg  aggagcagta caacagcacg      720
taccgtgtgg tcagcgtcct caccgtcctg caccaggact ggctgaatgg caaggagtac      780
aagtgcaagg tctccaacaa agccctccca gcccccatcg agaaaaccat ctccaaagcc      840
aaagggcagc cccgagaacc acaggtgtac accctgcccc catcccggga tgagctgacc      900
aagaaccagg tcagcctgac ctgcctggtc aaaggcttct atcccagcga catcgccgtg      960
gagtgggaga gcaatgggca gccggagaac aactacaaga ccacgcctcc cgtgctggac     1020
tccgacggct ccttcttcct ctacagcaag ctcaccgtgg acaagagcag gtggcagcag     1080
gggaacgtct tctcatgctc cgtgatgcat gaggctctgc acaaccacta cacgcagaag     1140
agcctctcgc tcagcccggg taaataa                                          1167
```

<210> SEQ ID NO 6
<211> LENGTH: 333
<212> TYPE: DNA
<213> ORGANISM: Artificial Sequence
<220> FEATURE:
<223> OTHER INFORMATION: sTNFR-I nucleotide sequence

<400> SEQUENCE: 6

```
catatggaca gcgtttgccc ccaaggaaaa tatatccacc ctcaaaataa ttcgatttgc       60
tgtaccaagt gccacaaagg aacctacttg tacaatgact gtccaggccc ggggcaggat      120
acggactgca gggagtgtga gagcggctcc ttcaccgctt cagaaaacca cctcagacac      180
tgcctcagct gctccaaatg ccgaaaggaa atgggtcagg tggagatctc ttcttgcaca      240
gtggaccggg acaccgtgtg tggttgcagg aagaaccagt accggcatta ttggagtgaa      300
aaccttttcc agtgcttcaa ttaataggga tcc                                    333
```

<210> SEQ ID NO 7
<211> LENGTH: 569
<212> TYPE: PRT
<213> ORGANISM: Homo sapiens

<400> SEQUENCE: 7

```
Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Glu Lys Ile Ile Leu
            20                  25                  30

Val Ser Ser Ala Asn Glu Ile Asp Val Arg Pro Cys Pro Leu Asn Pro
        35                  40                  45

Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80
```

```
Leu Trp Phe Val Pro Ala Lys Val Glu Asp Ser Gly His Tyr Tyr Cys
                85                  90                  95
Val Val Arg Asn Ser Ser Tyr Cys Leu Arg Ile Lys Ile Ser Ala Lys
            100                 105                 110
Phe Val Glu Asn Glu Pro Asn Leu Cys Tyr Asn Ala Gln Ala Ile Phe
        115                 120                 125
Lys Gln Lys Leu Pro Val Ala Gly Asp Gly Gly Leu Val Cys Pro Tyr
    130                 135                 140
Met Glu Phe Phe Lys Asn Glu Asn Asn Glu Leu Pro Lys Leu Gln Trp
145                 150                 155                 160
Tyr Lys Asp Cys Lys Pro Leu Leu Leu Asp Asn Ile His Phe Ser Gly
                165                 170                 175
Val Lys Asp Arg Leu Ile Val Met Asn Val Ala Glu Lys His Arg Gly
            180                 185                 190
Asn Tyr Thr Cys His Ala Ser Tyr Thr Tyr Leu Gly Lys Gln Tyr Pro
        195                 200                 205
Ile Thr Arg Val Ile Glu Phe Ile Thr Leu Glu Glu Asn Lys Pro Thr
    210                 215                 220
Arg Pro Val Ile Val Ser Pro Ala Asn Glu Thr Met Glu Val Asp Leu
225                 230                 235                 240
Gly Ser Gln Ile Gln Leu Ile Cys Asn Val Thr Gly Gln Leu Ser Asp
                245                 250                 255
Ile Ala Tyr Trp Lys Trp Asn Gly Ser Val Ile Asp Glu Asp Asp Pro
            260                 265                 270
Val Leu Gly Glu Asp Tyr Tyr Ser Val Glu Asn Pro Ala Asn Lys Arg
        275                 280                 285
Arg Ser Thr Leu Ile Thr Val Leu Asn Ile Ser Glu Ile Glu Ser Arg
    290                 295                 300
Phe Tyr Lys His Pro Phe Thr Cys Phe Ala Lys Asn Thr His Gly Ile
305                 310                 315                 320
Asp Ala Ala Tyr Ile Gln Leu Ile Tyr Pro Val Thr Asn Phe Gln Lys
                325                 330                 335
His Met Ile Gly Ile Cys Val Thr Leu Thr Val Ile Ile Val Cys Ser
            340                 345                 350
Val Phe Ile Tyr Lys Ile Phe Lys Ile Asp Ile Val Leu Trp Tyr Arg
        355                 360                 365
Asp Ser Cys Tyr Asp Phe Leu Pro Ile Lys Ala Ser Asp Gly Lys Thr
    370                 375                 380
Tyr Asp Ala Tyr Ile Leu Tyr Pro Lys Thr Val Gly Glu Gly Ser Thr
385                 390                 395                 400
Ser Asp Cys Asp Ile Phe Val Phe Lys Val Leu Pro Glu Val Leu Glu
                405                 410                 415
Lys Gln Cys Gly Tyr Lys Leu Phe Ile Tyr Gly Arg Asp Asp Tyr Val
            420                 425                 430
Gly Glu Asp Ile Val Glu Val Ile Asn Glu Asn Val Lys Lys Ser Arg
        435                 440                 445
Arg Leu Ile Ile Ile Leu Val Arg Glu Thr Ser Gly Phe Ser Trp Leu
    450                 455                 460
Gly Gly Ser Ser Glu Glu Gln Ile Ala Met Tyr Asn Ala Leu Val Gln
465                 470                 475                 480
Asp Gly Ile Lys Val Val Leu Leu Glu Leu Glu Lys Ile Gln Asp Tyr
                485                 490                 495
Glu Lys Met Pro Glu Ser Ile Lys Phe Ile Lys Gln Lys His Gly Ala
            500                 505                 510
```

```
Ile Arg Trp Ser Gly Asp Phe Thr Gln Gly Pro Gln Ser Ala Lys Thr
        515                 520                 525
Arg Phe Trp Lys Asn Val Arg Tyr His Met Pro Val Gln Arg Arg Ser
530                 535                 540
Pro Ser Ser Lys His Gln Leu Leu Ser Pro Ala Thr Lys Glu Lys Leu
545                 550                 555                 560
Gln Arg Glu Ala His Val Pro Leu Gly
                565

<210> SEQ ID NO 8
<211> LENGTH: 455
<212> TYPE: PRT
<213> ORGANISM: Homo sapiens

<400> SEQUENCE: 8

Met Gly Leu Ser Thr Val Pro Asp Leu Leu Leu Pro Leu Val Leu Leu
1               5                   10                  15
Glu Leu Leu Val Gly Ile Tyr Pro Ser Gly Val Ile Gly Leu Val Pro
                20                  25                  30
His Leu Gly Asp Arg Glu Lys Arg Asp Ser Val Cys Pro Gln Gly Lys
            35                  40                  45
Tyr Ile His Pro Gln Asn Asn Ser Ile Cys Cys Thr Lys Cys His Lys
        50                  55                  60
Gly Thr Tyr Leu Tyr Asn Asp Cys Pro Gly Pro Gly Gln Asp Thr Asp
65                  70                  75                  80
Cys Arg Glu Cys Glu Ser Gly Ser Phe Thr Ala Ser Glu Asn His Leu
                85                  90                  95
Arg His Cys Leu Ser Cys Ser Lys Cys Arg Lys Glu Met Gly Gln Val
            100                 105                 110
Glu Ile Ser Ser Cys Thr Val Asp Arg Asp Thr Val Cys Gly Cys Arg
        115                 120                 125
Lys Asn Gln Tyr Arg His Tyr Trp Ser Glu Asn Leu Phe Gln Cys Phe
130                 135                 140
Asn Cys Ser Leu Cys Leu Asn Gly Thr Val His Leu Ser Cys Gln Glu
145                 150                 155                 160
Lys Gln Asn Thr Val Cys Thr Cys His Ala Gly Phe Phe Leu Arg Glu
                165                 170                 175
Asn Glu Cys Val Ser Cys Ser Asn Cys Lys Lys Ser Leu Glu Cys Thr
            180                 185                 190
Lys Leu Cys Leu Pro Gln Ile Glu Asn Val Lys Gly Thr Glu Asp Ser
        195                 200                 205
Gly Thr Thr Val Leu Leu Pro Leu Val Ile Phe Phe Gly Leu Cys Leu
210                 215                 220
Leu Ser Leu Leu Phe Ile Gly Leu Met Tyr Arg Tyr Gln Arg Trp Lys
225                 230                 235                 240
Ser Lys Leu Tyr Ser Ile Val Cys Gly Lys Ser Thr Pro Glu Lys Glu
                245                 250                 255
Gly Glu Leu Glu Gly Thr Thr Thr Lys Pro Leu Ala Pro Asn Pro Ser
            260                 265                 270
Phe Ser Pro Thr Pro Gly Phe Thr Pro Thr Leu Gly Phe Ser Pro Val
        275                 280                 285
Pro Ser Ser Thr Phe Thr Ser Ser Ser Thr Tyr Thr Pro Gly Asp Cys
290                 295                 300
Pro Asn Phe Ala Ala Pro Arg Arg Glu Val Ala Pro Pro Tyr Gln Gly
305                 310                 315                 320
```

```
Ala Asp Pro Ile Leu Ala Thr Ala Leu Ala Ser Asp Pro Ile Pro Asn
            325                 330                 335

Pro Leu Gln Lys Trp Glu Asp Ser Ala His Lys Pro Gln Ser Leu Asp
            340                 345                 350

Thr Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
        370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
            435                 440                 445

Pro Ala Pro Ser Leu Leu Arg
        450                 455

<210> SEQ ID NO 9
<211> LENGTH: 461
<212> TYPE: PRT
<213> ORGANISM: Homo sapiens

<400> SEQUENCE: 9

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240
```

```
Phe Leu Leu Pro Met Gly Pro Ser Pro Ala Glu Gly Ser Thr Gly
            245             250             255

Asp Phe Ala Leu Pro Val Gly Leu Ile Val Gly Val Thr Ala Leu Gly
        260             265             270

Leu Leu Ile Ile Gly Val Val Asn Cys Val Ile Met Thr Gln Val Lys
        275             280             285

Lys Lys Pro Leu Cys Leu Gln Arg Glu Ala Lys Val Pro His Leu Pro
        290             295             300

Ala Asp Lys Ala Arg Gly Thr Gln Gly Pro Glu Gln Gln His Leu Leu
305             310             315             320

Ile Thr Ala Pro Ser Ser Ser Ser Ser Leu Glu Ser Ala Ser
            325             330             335

Ala Leu Asp Arg Arg Ala Pro Thr Arg Asn Gln Pro Gln Ala Pro Gly
        340             345             350

Val Glu Ala Ser Gly Ala Gly Glu Ala Arg Ala Ser Thr Gly Ser Ser
            355             360             365

Asp Ser Ser Pro Gly Gly His Gly Thr Gln Val Asn Val Thr Cys Ile
        370             375             380

Val Asn Val Cys Ser Ser Ser Asp His Ser Ser Gln Cys Ser Ser Gln
385             390             395             400

Ala Ser Ser Thr Met Gly Asp Thr Asp Ser Ser Pro Ser Glu Ser Pro
            405             410             415

Lys Asp Glu Gln Val Pro Phe Ser Lys Glu Glu Cys Ala Phe Arg Ser
        420             425             430

Gln Leu Glu Thr Pro Glu Thr Leu Leu Gly Ser Thr Glu Lys Pro
        435             440             445

Leu Pro Leu Gly Val Pro Asp Ala Gly Met Lys Pro Ser
        450             455             460

<210> SEQ ID NO 10
<211> LENGTH: 277
<212> TYPE: PRT
<213> ORGANISM: Homo sapiens

<400> SEQUENCE: 10

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160
```

```
Cys His Pro Trp Thr Ser Cys Glu Thr Lys Asp Leu Val Val Gln
            165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
            195                 200                 205

Leu Leu Val Leu Val Phe Ile Lys Lys Val Ala Lys Lys Pro Thr Asn
            210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
            245                 250                 255

Gly Cys Gln Pro Val Thr Gln Glu Asp Gly Lys Glu Ser Arg Ile Ser
            260                 265                 270

Val Gln Glu Arg Gln
            275

<210> SEQ ID NO 11
<211> LENGTH: 595
<212> TYPE: PRT
<213> ORGANISM: Homo sapiens

<400> SEQUENCE: 11

Met Arg Val Leu Leu Ala Ala Leu Gly Leu Leu Phe Leu Gly Ala Leu
1               5                   10                  15

Arg Ala Phe Pro Gln Asp Arg Pro Phe Glu Asp Thr Cys His Gly Asn
            20                  25                  30

Pro Ser His Tyr Tyr Asp Lys Ala Val Arg Arg Cys Cys Tyr Arg Cys
            35                  40                  45

Pro Met Gly Leu Phe Pro Thr Gln Gln Cys Pro Gln Arg Pro Thr Asp
    50                  55                  60

Cys Arg Lys Gln Cys Glu Pro Asp Tyr Tyr Leu Asp Glu Ala Asp Arg
65                  70                  75                  80

Cys Thr Ala Cys Val Thr Cys Ser Arg Asp Asp Leu Val Glu Lys Thr
            85                  90                  95

Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe Phe His
            115                 120                 125

Ser Val Cys Pro Ala Gly Met Ile Val Lys Phe Pro Gly Thr Ala Gln
            130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
            165                 170                 175

Ala Lys Pro Thr Pro Val Ser Pro Ala Thr Ser Ser Ala Ser Thr Met
            180                 185                 190

Pro Val Arg Gly Gly Thr Arg Leu Ala Gln Glu Ala Ala Ser Lys Leu
            195                 200                 205

Thr Arg Ala Pro Asp Ser Pro Ser Ser Val Gly Arg Pro Ser Ser Asp
            210                 215                 220

Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Glu Ala Gly Arg Cys
            245                 250                 255
```

```
Thr Ala Cys Val Ser Cys Ser Arg Asp Asp Leu Val Glu Lys Thr Pro
            260                 265                 270

Cys Ala Trp Asn Ser Ser Arg Thr Cys Glu Cys Arg Pro Gly Met Ile
                275                 280                 285

Cys Ala Thr Ser Ala Thr Asn Ser Cys Ala Arg Cys Val Pro Tyr Pro
            290                 295                 300

Ile Cys Ala Ala Glu Thr Val Thr Lys Pro Gln Asp Met Ala Glu Lys
305                 310                 315                 320

Asp Thr Thr Phe Glu Ala Pro Pro Leu Gly Thr Gln Pro Asp Cys Asn
                325                 330                 335

Pro Thr Pro Glu Asn Gly Glu Ala Pro Ala Ser Thr Ser Pro Thr Gln
            340                 345                 350

Ser Leu Leu Val Asp Ser Gln Ala Ser Lys Thr Leu Pro Ile Pro Thr
            355                 360                 365

Ser Ala Pro Val Ala Leu Ser Ser Thr Gly Lys Pro Val Leu Asp Ala
            370                 375                 380

Gly Pro Val Leu Phe Trp Val Ile Leu Val Leu Val Val Val Val Gly
385                 390                 395                 400

Ser Ser Ala Phe Leu Leu Cys His Arg Arg Ala Cys Arg Lys Arg Ile
                405                 410                 415

Arg Gln Lys Leu His Leu Cys Tyr Pro Val Gln Thr Ser Gln Pro Lys
            420                 425                 430

Leu Glu Leu Val Asp Ser Arg Pro Arg Arg Ser Ser Thr Gln Leu Arg
            435                 440                 445

Ser Gly Ala Ser Val Thr Glu Pro Val Ala Glu Arg Gly Leu Met
            450                 455                 460

Ser Gln Pro Leu Met Glu Thr Cys His Ser Val Gly Ala Ala Tyr Leu
465                 470                 475                 480

Glu Ser Leu Pro Leu Gln Asp Ala Ser Pro Ala Gly Gly Pro Ser Ser
                485                 490                 495

Pro Arg Asp Leu Pro Glu Pro Arg Val Ser Thr Glu His Thr Asn Asn
            500                 505                 510

Lys Ile Glu Lys Ile Tyr Ile Met Lys Ala Asp Thr Val Ile Val Gly
            515                 520                 525

Thr Val Lys Ala Glu Leu Pro Glu Gly Arg Gly Leu Ala Gly Pro Ala
            530                 535                 540

Glu Pro Glu Leu Glu Glu Leu Glu Ala Asp His Thr Pro His Tyr
545                 550                 555                 560

Pro Glu Gln Glu Thr Glu Pro Pro Leu Gly Ser Cys Ser Asp Val Met
                565                 570                 575

Leu Ser Val Glu Glu Glu Gly Lys Glu Asp Pro Leu Pro Thr Ala Ala
            580                 585                 590

Ser Gly Lys
595

<210> SEQ ID NO 12
<211> LENGTH: 199
<212> TYPE: PRT
<213> ORGANISM: Homo sapiens

<400> SEQUENCE: 12

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30
```

```
Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Phe Lys Val Thr Leu Thr Gly Gly Tyr Leu
            115                 120                 125

His Ile Tyr Glu Ser Gln Leu Cys Cys Gln Leu Lys Phe Trp Leu Pro
        130                 135                 140

Ile Gly Cys Ala Ala Phe Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
        195

<210> SEQ ID NO 13
<211> LENGTH: 220
<212> TYPE: PRT
<213> ORGANISM: Homo sapiens

<400> SEQUENCE: 13

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190
```

```
Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 14
<211> LENGTH: 277
<212> TYPE: PRT
<213> ORGANISM: Homo sapiens

<400> SEQUENCE: 14

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 15
<211> LENGTH: 255
<212> TYPE: PRT
<213> ORGANISM: Homo sapiens
```

-continued

```
<400> SEQUENCE: 15

Met Gly Asn Ser Cys Tyr Asn Ile Val Ala Thr Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 16
<211> LENGTH: 260
<212> TYPE: PRT
<213> ORGANISM: Homo sapiens

<400> SEQUENCE: 16

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
            35                  40                  45

Leu Val Lys Asp Cys Asp Gln His Arg Lys Ala Ala Gln Cys Asp Pro
50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110
```

-continued

Arg Asp Lys Glu Cys Thr Glu Cys Asp Pro Leu Pro Asn Pro Ser Leu
            115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr Arg Ser Asn Lys Gly Glu Ser
210                 215                 220

Pro Val Glu Pro Ala Glu Pro Cys Arg Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
            260

<210> SEQ ID NO 17
<211> LENGTH: 541
<212> TYPE: PRT
<213> ORGANISM: Homo sapiens

<400> SEQUENCE: 17

Met Asn Cys Arg Glu Leu Pro Leu Thr Leu Trp Val Leu Ile Ser Val
1               5                   10                  15

Ser Thr Ala Glu Ser Cys Thr Ser Arg Pro His Ile Thr Val Val Glu
            20                  25                  30

Gly Glu Pro Phe Tyr Leu Lys His Cys Ser Cys Ser Leu Ala His Glu
        35                  40                  45

Ile Glu Thr Thr Thr Lys Ser Trp Tyr Lys Ser Ser Gly Ser Gln Glu
    50                  55                  60

His Val Glu Leu Asn Pro Arg Ser Ser Arg Ile Ala Leu His Asp
65                  70                  75                  80

Cys Val Leu Glu Phe Trp Pro Val Glu Leu Asn Asp Thr Gly Ser Tyr
                85                  90                  95

Phe Phe Gln Met Lys Asn Tyr Thr Gln Lys Trp Lys Leu Asn Val Ile
            100                 105                 110

Arg Arg Asn Lys His Ser Cys Phe Thr Glu Arg Gln Val Thr Ser Lys
        115                 120                 125

Ile Val Glu Val Lys Lys Phe Phe Gln Ile Thr Cys Glu Asn Ser Tyr
    130                 135                 140

Tyr Gln Thr Leu Val Asn Ser Thr Ser Leu Tyr Lys Asn Cys Lys Lys
145                 150                 155                 160

Leu Leu Leu Glu Asn Asn Lys Asn Pro Thr Ile Lys Lys Asn Ala Glu
                165                 170                 175

Phe Glu Asp Gln Gly Tyr Tyr Ser Cys Val His Phe Leu His His Asn
            180                 185                 190

Gly Lys Leu Phe Asn Ile Thr Lys Thr Phe Asn Ile Thr Ile Val Glu
        195                 200                 205

Asp Arg Ser Asn Ile Val Pro Val Leu Leu Gly Pro Lys Leu Asn His
    210                 215                 220

Val Ala Val Glu Leu Gly Lys Asn Val Arg Leu Asn Cys Ser Ala Leu
225                 230                 235                 240

Leu Asn Glu Glu Asp Val Ile Tyr Trp Met Phe Gly Glu Glu Asn Gly
            245                 250                 255

Ser Asp Pro Asn Ile His Glu Glu Lys Glu Met Arg Ile Met Thr Pro
        260                 265                 270

Glu Gly Lys Trp His Ala Ser Lys Val Leu Arg Ile Glu Asn Ile Gly
    275                 280                 285

Glu Ser Asn Leu Asn Val Leu Tyr Asn Cys Thr Val Ala Ser Thr Gly
290                 295                 300

Gly Thr Asp Thr Lys Ser Phe Ile Leu Val Arg Lys Ala Asp Met Ala
305                 310                 315                 320

Asp Ile Pro Gly His Val Phe Thr Arg Gly Met Ile Ile Ala Val Leu
                325                 330                 335

Ile Leu Val Ala Val Val Cys Leu Val Thr Val Cys Val Ile Tyr Arg
            340                 345                 350

Val Asp Leu Val Leu Phe Tyr Arg His Leu Thr Arg Arg Asp Glu Thr
        355                 360                 365

Leu Thr Asp Gly Lys Thr Tyr Asp Ala Phe Val Ser Tyr Leu Lys Glu
    370                 375                 380

Cys Arg Pro Glu Asn Gly Glu Glu His Thr Phe Ala Val Glu Ile Leu
385                 390                 395                 400

Pro Arg Val Leu Glu Lys His Phe Gly Tyr Lys Leu Cys Ile Phe Glu
                405                 410                 415

Arg Asp Val Val Pro Gly Gly Ala Val Val Asp Glu Ile His Ser Leu
            420                 425                 430

Ile Glu Lys Ser Arg Arg Leu Ile Ile Val Leu Ser Lys Ser Tyr Met
        435                 440                 445

Ser Asn Glu Val Arg Tyr Glu Leu Glu Ser Gly Leu His Glu Ala Leu
    450                 455                 460

Val Glu Arg Lys Ile Lys Ile Ile Leu Ile Glu Phe Thr Pro Val Thr
465                 470                 475                 480

Asp Phe Thr Phe Leu Pro Gln Ser Leu Lys Leu Leu Lys Ser His Arg
                485                 490                 495

Val Leu Lys Trp Lys Ala Asp Lys Ser Leu Ser Tyr Asn Ser Arg Phe
            500                 505                 510

Trp Lys Asn Leu Leu Tyr Leu Met Pro Ala Lys Thr Val Lys Pro Gly
        515                 520                 525

Arg Asp Glu Pro Glu Val Leu Pro Val Leu Ser Glu Ser
    530                 535                 540

<210> SEQ ID NO 18
<211> LENGTH: 288
<212> TYPE: PRT
<213> ORGANISM: Homo sapiens

<400> SEQUENCE: 18

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

```
Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Ser Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 19
<211> LENGTH: 223
<212> TYPE: PRT
<213> ORGANISM: Mus musculus

<400> SEQUENCE: 19

Met Ala Cys Leu Gly Arg Arg Tyr Lys Ala Gln Leu Gln Leu Pro
  1               5                  10                  15

Ser Arg Thr Trp Pro Phe Val Ala Leu Thr Leu Leu Phe Ile Pro
                 20                  25                  30

Val Phe Ser Glu Ala Ile Gln Val Thr Gln Pro Ser Val Val Leu Ala
             35                  40                  45

Ser Ser His Gly Val Ala Ser Phe Pro Cys Glu Tyr Ser Pro Ser His
         50                  55                  60

Asn Thr Asp Glu Val Arg Val Thr Val Leu Arg Gln Thr Asn Asp Gln
 65                  70                  75                  80

Met Thr Glu Val Cys Ala Thr Thr Phe Thr Glu Lys Asn Thr Val Gly
                 85                  90                  95

Phe Leu Asp Tyr Pro Phe Cys Ser Gly Thr Phe Asn Glu Ser Arg Val
            100                 105                 110

Asn Leu Thr Ile Gln Gly Leu Arg Ala Val Asp Thr Gly Leu Tyr Leu
        115                 120                 125

Cys Lys Val Glu Leu Met Tyr Pro Pro Tyr Phe Val Gly Met Gly
    130                 135                 140

Asn Gly Thr Gln Ile Tyr Val Ile Asp Pro Glu Pro Cys Pro Asp Ser
145                 150                 155                 160
```

```
Asp Phe Leu Leu Trp Ile Leu Val Ala Val Ser Gly Leu Phe Phe
                165                 170                 175

Tyr Ser Phe Leu Val Ser Ala Val Ser Leu Ser Lys Met Leu Lys Lys
                180                 185                 190

Arg Ser Pro Leu Thr Thr Gly Val Tyr Val Lys Met Pro Pro Thr Glu
                195                 200                 205

Pro Glu Cys Glu Lys Gln Phe Gln Pro Tyr Phe Ile Pro Ile Asn
    210                 215                 220

<210> SEQ ID NO 20
<211> LENGTH: 153
<212> TYPE: PRT
<213> ORGANISM: Homo sapiens

<400> SEQUENCE: 20

Met Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
                20                  25                  30

Ala Gly Tyr Leu Gln Gly Pro Asn Val Asn Leu Glu Glu Lys Ile Asp
            35                  40                  45

Val Val Pro Ile Glu Pro His Ala Leu Phe Leu Gly Ile His Gly Gly
        50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140

Thr Lys Phe Tyr Phe Gln Glu Asp Glu
145                 150

<210> SEQ ID NO 21
<211> LENGTH: 461
<212> TYPE: PRT
<213> ORGANISM: Rattus norvegicus

<400> SEQUENCE: 21

Met Gly Leu Pro Ile Val Pro Gly Leu Leu Leu Ser Leu Val Leu Leu
1               5                   10                  15

Ala Leu Leu Met Gly Ile His Pro Ser Gly Val Thr Gly Leu Val Pro
                20                  25                  30

Ser Leu Gly Asp Arg Glu Lys Arg Asp Asn Leu Cys Pro Gln Gly Lys
            35                  40                  45

Tyr Ala His Pro Lys Asn Asn Ser Ile Cys Cys Thr Lys Cys His Lys
        50                  55                  60

Gly Thr Tyr Leu Val Ser Asp Cys Pro Ser Pro Gly Gln Glu Thr Val
65                  70                  75                  80

Cys Glu Val Cys Asp Lys Gly Thr Phe Thr Ala Ser Gln Asn His Val
                85                  90                  95

Arg Gln Cys Leu Ser Cys Lys Thr Cys Arg Lys Glu Met Phe Gln Val
            100                 105                 110
```

```
Glu Ile Ser Pro Cys Lys Ala Asp Met Asp Thr Val Cys Gly Cys Lys
            115                 120                 125
Lys Asn Gln Phe Gln Arg Tyr Leu Ser Glu Thr His Phe Gln Cys Val
        130                 135                 140
Asp Cys Ser Pro Cys Phe Asn Gly Thr Val Thr Ile Pro Cys Lys Glu
145                 150                 155                 160
Lys Gln Asn Thr Val Cys Asn Cys His Ala Gly Phe Phe Leu Ser Gly
                165                 170                 175
Asn Glu Cys Thr Pro Cys Ser His Cys Lys Lys Asn Gln Glu Cys Met
            180                 185                 190
Lys Leu Cys Leu Pro Pro Val Ala Asn Val Thr Asn Pro Gln Asp Ser
        195                 200                 205
Gly Thr Ala Val Leu Leu Pro Leu Val Ile Phe Leu Gly Leu Cys Leu
210                 215                 220
Leu Phe Phe Ile Cys Ile Ser Leu Leu Cys Arg Tyr Pro Gln Trp Arg
225                 230                 235                 240
Pro Arg Val Tyr Ser Ile Ile Cys Arg Asp Ser Ala Pro Val Lys Glu
                245                 250                 255
Val Glu Gly Glu Gly Ile Val Thr Lys Pro Leu Thr Pro Ala Ser Ile
            260                 265                 270
Pro Ala Phe Ser Pro Asn Pro Gly Phe Asn Pro Thr Leu Gly Phe Ser
        275                 280                 285
Thr Thr Pro Arg Phe Ser His Pro Val Ser Ser Thr Pro Ile Ser Pro
290                 295                 300
Val Phe Gly Pro Ser Asn Trp His Asn Phe Val Pro Pro Val Arg Glu
305                 310                 315                 320
Val Val Pro Thr Gln Gly Ala Asp Pro Leu Leu Tyr Gly Ser Leu Asn
                325                 330                 335
Pro Val Pro Ile Pro Ala Pro Val Arg Lys Trp Glu Asp Val Val Ala
            340                 345                 350
Ala Gln Pro Gln Arg Leu Asp Thr Ala Asp Pro Ala Met Leu Tyr Ala
        355                 360                 365
Val Val Asp Gly Val Pro Pro Thr Arg Trp Lys Glu Phe Met Arg Leu
370                 375                 380
Leu Gly Leu Ser Glu His Glu Ile Glu Arg Leu Glu Leu Gln Asn Gly
385                 390                 395                 400
Arg Cys Leu Arg Glu Ala His Tyr Ser Met Leu Glu Ala Trp Arg Arg
                405                 410                 415
Arg Thr Pro Arg His Glu Ala Thr Leu Asp Val Val Gly Arg Val Leu
            420                 425                 430
Cys Asp Met Asn Leu Arg Gly Cys Leu Glu Asn Ile Arg Glu Thr Leu
        435                 440                 445
Glu Ser Pro Ala His Ser Ser Thr Thr His Leu Pro Arg
450                 455                 460

<210> SEQ ID NO 22
<211> LENGTH: 235
<212> TYPE: PRT
<213> ORGANISM: Artificial Sequence
<220> FEATURE:
<223> OTHER INFORMATION: Fc3A C8S amino acid sequence
```

-continued

<400> SEQUENCE: 22

Ala Ala Ala Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asn Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Lys
225                 230                 235

<210> SEQ ID NO 23
<211> LENGTH: 19
<212> TYPE: DNA
<213> ORGANISM: Artificial Sequence
<220> FEATURE:
<223> OTHER INFORMATION: Primer

<400> SEQUENCE: 23
ccacgaagac cctgaggtc                                                19

<210> SEQ ID NO 24
<211> LENGTH: 28
<212> TYPE: DNA
<213> ORGANISM: Artificial Sequence
<220> FEATURE:
<223> OTHER INFORMATION: Primer

<400> SEQUENCE: 24
gggtaaaatg cgaccgtccg gccgtaag                                      28

<210> SEQ ID NO 25
<211> LENGTH: 28
<212> TYPE: DNA
<213> ORGANISM: Artificial Sequence
<220> FEATURE:
<223> OTHER INFORMATION: Primer

```
<400> SEQUENCE: 25
ggacggtcgc attttacccg ggctgagc                                           28

<210> SEQ ID NO 26
<211> LENGTH: 19
<212> TYPE: DNA
<213> ORGANISM: Artificial Sequence
<220> FEATURE:
<223> OTHER INFORMATION: Primer

<400> SEQUENCE: 26
ctggttgttg cgcaggtag                                                     19

<210> SEQ ID NO 27
<211> LENGTH: 293
<212> TYPE: PRT
<213> ORGANISM: Homo sapiens

<400> SEQUENCE: 27
```

Met Ser Gly Leu Gly Arg Ser Arg Arg Gly Gly Arg Ser Arg Val Asp
1               5                   10                  15

Gln Glu Glu Arg Phe Pro Gln Gly Leu Trp Thr Gly Val Ala Met Arg
                20                  25                  30

Ser Cys Pro Glu Glu Gln Tyr Trp Asp Pro Leu Leu Gly Thr Cys Met
            35                  40                  45

Ser Cys Lys Thr Ile Cys Asn His Gln Ser Gln Arg Thr Cys Ala Ala
        50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
    130                 135                 140

Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
                165                 170                 175

Cys Phe Leu Val Ala Val Ala Cys Phe Leu Lys Lys Arg Gly Asp Pro
            180                 185                 190

Cys Ser Cys Gln Pro Arg Ser Arg Pro Arg Gln Ser Pro Ala Lys Ser
        195                 200                 205

Ser Gln Asp His Ala Met Glu Ala Gly Ser Pro Val Ser Thr Ser Pro
    210                 215                 220

Glu Pro Val Glu Thr Cys Ser Phe Cys Phe Pro Glu Cys Arg Ala Pro
225                 230                 235                 240

Thr Gln Glu Ser Ala Val Thr Pro Gly Thr Pro Asp Pro Thr Cys Ala
                245                 250                 255

Gly Arg Trp Gly Cys His Thr Arg Thr Thr Val Leu Gln Pro Cys Pro
            260                 265                 270

His Ile Pro Asp Ser Gly Leu Gly Ile Val Cys Val Pro Ala Gln Glu
        275                 280                 285

Gly Gly Pro Gly Ala
    290

```
<210> SEQ ID NO 28
<211> LENGTH: 22
<212> TYPE: DNA
<213> ORGANISM: Artificial Sequence
<220> FEATURE:
<223> OTHER INFORMATION: Oligonucleotide linker

<400> SEQUENCE: 28
cgcgagatct tgcgcaagat ct                                              22
```